US008518956B2

(12) United States Patent
Tollefson

(10) Patent No.: US 8,518,956 B2
(45) Date of Patent: Aug. 27, 2013

(54) 1-(1-(2-ETHOXYETHYL)-3-ETHYL-7-(4-METHYLPYRIDIN-2-YLAMINO)-1H-PYRAZOLO[4,3-D]PYRIMIDIN-5-YL)PIPERIDINE-4-CARBOXYLIC ACID AND SALTS THEREOF

(75) Inventor: Michael B. Tollefson, Dardenne Prairie, MO (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 219 days.

(21) Appl. No.: 12/948,387

(22) Filed: Nov. 17, 2010

(65) Prior Publication Data

US 2011/0059993 A1   Mar. 10, 2011

Related U.S. Application Data

(63) Continuation of application No. 11/558,306, filed on Nov. 9, 2006, now abandoned.

(60) Provisional application No. 60/735,320, filed on Nov. 10, 2005.

(51) Int. Cl.
| | |
|---|---|
| *C07D 487/04* | (2006.01) |
| *A61K 31/519* | (2006.01) |
| *A61P 15/10* | (2006.01) |
| *A61P 9/12* | (2006.01) |

(52) U.S. Cl.
USPC ........................................ 514/262.1; 544/262

(58) Field of Classification Search
USPC ..................................... 544/262; 514/262.1
See application file for complete search history.

(56) References Cited

U.S. PATENT DOCUMENTS

| 6,207,829 B1 | 3/2001 | Dunn et al. ................... 544/262 |
| 2005/0043325 A1 | 2/2005 | Bell et al. | |

FOREIGN PATENT DOCUMENTS

| EP | 1348707 | 1/2003 |
| WO | WO9801428 | 1/1998 |
| WO | WO9954333 | 10/1999 |
| WO | WO0024745 | 5/2000 |
| WO | WO0118004 | 3/2001 |
| WO | WO0183472 | 11/2001 |
| WO | WO0200660 | 1/2002 |
| WO | WO0216348 | 2/2002 |
| WO | WO2004096810 | 11/2004 |
| WO | WO2004103407 | 12/2004 |
| WO | WO2005046698 | 5/2005 |
| WO | WO2005049616 | 6/2005 |
| WO | WO2005049617 | 6/2005 |
| WO | WO2005097799 | 10/2005 |
| WO | WO2006014325 | 2/2006 |
| WO | WO2006046135 | 5/2006 |

OTHER PUBLICATIONS

Stahl, P. H. and Wermuth, C. G. (Eds.) *Handbook of Pharmaceutical Salts: Properties, Selection, and Use*, Wiley-VCH, 2002, table of contents (TOC).
Hoover, J.E., Remington's Pharmaceutical Sciences, Mack Publishing Co., Easton, Pennsylvania, 1975, TOC.
Liberman, et al., Eds., Pharmaceutical Dosage Forms, Marcel Decker, New York, New York, 1980, TOC.
Kibbe, et al., Eds., Handbook of Pharmaceutical Excipients (3rd Ed.), American Pharmaceutical Association, Washington, 1999, TOC.
Compendium of Organic Synthetic Methods, vol. I-VI, Wiley-Interscience, TOC, 1971.
Thompson, WJ, et al., *Purification and Characterization of High-Affinity Cyclic Adenosine Monophosphate Phosphodiesterase from Dog Kidney*, Biochemistry 18(23), 5228-5237, 1979.
Ballard, SA, et al., *Effects of Sildenafil on the Relaxation of Human Corpus Cavernosum Tissue in Vitro and on the Activities of Cyclic Nucleotide Phosphodiesterase Isozymes*, J. Urology 159(6), 2164-2171, 1998.
De Lean, A., Munson, P.J., and Rodbard, A, *Simultaneous Analysis of Families of Sigmoidal Curves, Application to Bioassay, Radioligand Assay, and Physiological Dose-Response Curves*, Am. J. Physiol., 235(2): E97-E102, 1978.
Ames, B.N., Durston, W.E., Yamasaki, E, and Lee, F.D., *Carcinogens are Mutagens: A Simple Test System Combining Liver Homogenates for Activation and Bacteria for Detection*, Proc. Nat. Acad. Sci., 70(8), 2281-2285, 1973.
The Merck Index 13th edition, copyright 2006,2009, Monograph No. 08489.

*Primary Examiner* — Susanna Moore
(74) *Attorney, Agent, or Firm* — James T. Wasicak

(57) ABSTRACT

The present invention comprises 1-(1-(2-ethoxyethyl)-3-ethyl-7-(4-methylpyridin-2-ylamino)-1H-pyrazolo[4,3-d]pyrimidin-5-yl)piperidine-4-carboxylic acid and its salts. The invention further comprises pharmaceutical compositions, methods of treatment, and synthetic methods relating to 1-(1-(2-ethoxyethyl)-3-ethyl-7-(4-methylpyridin-2-ylamino)-1H-pyrazolo[4,3-d]pyrimidin-5-yl)piperidine-4-carboxylic acid and its salts.

8 Claims, 2 Drawing Sheets

1-(1-(2-ETHOXYETHYL)-3-ETHYL-7-(4-METHYLPYRIDIN-2-YLAMINO)-1H-PYRAZOLO[4,3-D]PYRIMIDIN-5-YL) PIPERIDINE-4-CARBOXYLIC ACID AND SALTS THEREOF

This application is a continuation of U.S. application Ser. No. 11/558,306 filed Nov. 09, 2006 now abandoned, which claims the benefit of priority from U.S. Provisional Patent Application No. 60/735,320, filed Nov. 10, 2005, each of which are herein incorporated by reference for any reason.

FIELD OF THE INVENTION

The present invention relates generally to 1-(1-(2-ethoxyethyl)-3-ethyl-7-(4-methylpyridin-2-ylamino)-1H-pyrazolo[4,3-d]pyrimidin-5-yl)piperidine-4-carboxylic acid and its salts. The present invention further relates to pharmaceutical compositions comprising this compound or its salts, methods of treatment employing this compound or its salts, and methods of preparing this compound or its salts. In general, the compound and its salts inhibit the cyclic guanylate monophosphate-specific phosphodiesterase type 5 ("PDE5") enzyme.

BACKGROUND OF THE INVENTION

Hypertension is a condition associated with, among other physiological problems, an increased risk of stroke, myocardial infarction, atrial fibrillation, heart failure, peripheral vascular disease and renal impairment. Despite the numerous drugs available in various pharmacological categories to treat hypertension and related physiological problems, not all patients respond to such drugs as effectively or as safely as desired. Additional therapeutic agents for the treatment of hypertension and/or related conditions are still needed.

One class of therapeutic agents reported in the literature as useful for the treatment of hypertension are inhibitors of the PDE5 enzyme ("PDE5 inhibitors"). In general, vascular endothelial cells secrete nitric oxide which acts on vascular smooth muscle cells and leads to the activation of guanylate cyclase and the accumulation of cyclic guanosine monophosphate ("cGMP"). The accumulation of cGMP causes the muscles to relax and the blood vessels to dilate, leading to a reduction in blood pressure. The cGMP is inactivated by hydrolysis to guanosine 5'-monophosphate ("GMP") by cGMP-specific phosphodiesterases. One cGMP-phosphodiesterase involved in the inactivation of cGMP is the PDE5 enzyme. Inhibitors of the PDE5 enzyme decrease the rate of cGMP hydrolysis. This reduction in cGMP hydrolysis potentiates the actions of nitric oxide leading to a lowering of blood pressure.

Compounds that are PDE5 inhibitors have been reported in the literature. For example, WO2005049616 reports one class of pyrazolo[4,3-d]pyrimidinyl compounds. WO2005049617 reports another class of pyrazolo[4,3-d]pyrimidinyl compounds. WO2004096810 reports another class of pyrazolo[4,3-d]pyrimidinyl compounds. EP 1348707 reports another class of pyrazolo[4,3-d]pyrimidinyl compounds.

The identification of additional compounds that are PDE5 inhibitors is desirable. Such compounds can be used to treat subjects suffering from or susceptible to hypertension and/or related physiological problems and further expand the range of treatment options available for such subjects.

SUMMARY OF THE INVENTION

In one embodiment, the invention comprises 1-(1-(2-ethoxyethyl)-3-ethyl-7-(4-methylpyridin-2-ylamino)-1H-pyrazolo[4,3-d]pyrimidin-5-yl)piperidine-4-carboxylic acid and its pharmaceutically acceptable salts.

In another embodiment, the invention comprises a pharmaceutical composition comprising 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof, and a pharmaceutically-acceptable carrier.

In another embodiment, the invention comprises a pharmaceutical composition comprising 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof, one or more additional therapeutic agents, and a pharmaceutically acceptable carrier.

In another embodiment, the invention comprises methods for treating a condition in a subject by administering to a subject a therapeutically effective amount of 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof. Conditions that can be treated in accordance with the present invention include cardiovascular conditions, metabolic conditions, central nervous system conditions, pulmonary conditions, sexual dysfunction, pain, and renal dysfunction.

In another embodiment, the invention comprises methods for treating a condition in a subject by administering to a subject a therapeutically effective amount of 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof, one or more additional therapeutic agents, and a pharmaceutically acceptable carrier. Conditions that can be treated in accordance with the present invention include cardiovascular conditions, metabolic conditions, central nervous system conditions, pulmonary conditions, sexual dysfunction, pain, and renal dysfunction.

In another embodiment, the invention comprises use of 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof, for the manufacture of a medicament for the treatment of a condition in a subject. Such conditions include cardiovascular conditions, metabolic conditions, central nervous system conditions, pulmonary conditions, sexual dysfunction, pain, and renal dysfunction.

In another embodiment, the invention comprises methods for making 1-(1-(2-ethoxyethyl)-3-ethyl-7-(4-methylpyridin-2-ylamino)-1H-pyrazolo[4,3-d]pyrimidin-5-yl)piperidine-4-carboxylic acid, or a pharmaceutically acceptable salt thereof.

DETAILED DESCRIPTION OF THE INVENTION

Figure 1:
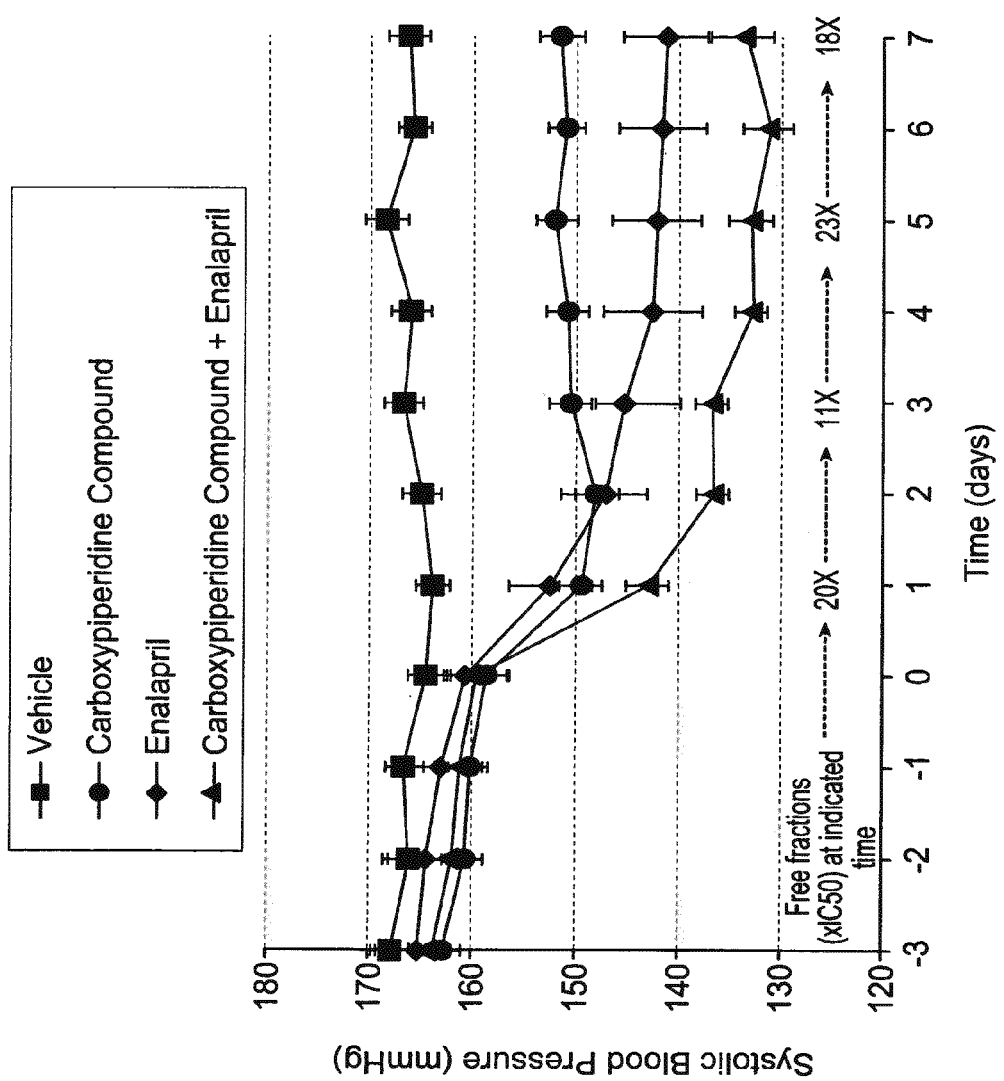
FIG. 1 shows a graph illustrating the effect on blood pressure of repeated oral administration of 1-(1-(2-ethoxyethyl)-3-ethyl-7-(4-methylpyridin-2-ylamino)-1H-pyrazolo[4,3-d]pyrimidin-5-yl)piperidine-4-carboxylic acid (1 mg/kg daily oral dose), alone and in combination with enalapril, in a conscious spontaneous hypertensive rat model.

This detailed description of embodiments is intended only to acquaint others skilled in the art with Applicants' inventions, its principles, and its practical application so that others skilled in the art may adapt and apply the inventions in their numerous forms, as they may be best suited to the requirements of a particular use. These inventions, therefore, are not limited to the embodiments described in this specification, and may be variously modified.

A. Abbreviations and Definitions

As used in reference to $^1$H NMR, the symbol "δ" refers to a $^1$H NMR chemical shift.

As used in reference to $^1$H NMR, the abbreviation "br" refers to a broad $^1$H NMR signal.

As used in reference to $^1$H NMR, the abbreviation "d" refers to a doublet $^1$H NMR peak.

As used in reference to $^1$H NMR, the abbreviation "m" refers to a multiplet $^1$H NMR peak.

As used in reference to $^1$H NMR, the abbreviation "q" refers to a quartet $^1$H NMR peak.

As used in reference to $^1$H NMR, the abbreviation "s" refers to a singlet $^1$H NMR peak.

As used in reference to $^1$H NMR, the abbreviation "t" refers to a triplet $^1$H NMR peak.

The abbreviation "BSA" refers to bovine serum albumin.

The abbreviation "CDI" refers to carbodiimide.

The abbreviation "DMSO" refers to dimethylsulfoxide.

The abbreviation "DBAD" refers to dibenzylazodicarboxylate.

The abbreviation "EDTA" refers to ethylenediaminetetraacetic acid.

The abbreviation "HEPES" refers to 4-(2-hydroxyethyl)-1-piperazineethanesulfonic acid.

The abbreviation "HRMS" refers to High Resolution Mass Spectroscopy (electrospray ionisation positive scan).

The abbreviation "iPrOAc" refers to isopropyl acetate.

The abbreviation "LCMS" refers to Liquid Chromatography Mass Spectroscopy.

The abbreviation "m/z" refers to a Mass spectrum peak.

The abbreviation "NaN(TMS)$_2$" refers to sodium hexamethyldisilazide.

The abbreviation "pfu" refers to plaque-forming units.

The abbreviation "Pt/C" refers to platinum on carbon.

The abbreviation "PMSF" refers to phenylmethylsulfonyl fluoride.

The abbreviation "SPA" refers to scintillation proximity assay.

The abbreviation "THF" refers to tetrahydrofuran.

The abbreviation "Tris-HCl" refers to Tris(hydroxymethyl)aminomethane hydrochloride.

The term "cGMP-mediated condition" refers to any condition mediated by cGMP, whether through direct regulation by cGMP, or through indirect regulation by cGMP as a component of a signalling pathway.

The term "PDE5-mediated condition" refers to any condition mediated by the PDE5 enzyme.

The term "hypertensive subject" refers to a subject having hypertension, suffering from the effects of hypertension or susceptible to a hypertensive condition if not treated to prevent or control such hypertension.

The term "pharmaceutically acceptable carrier" refers to a carrier that is compatible with the other ingredients of the composition and is not deleterious to the subject. Such carriers may be a pharmaceutically acceptable material, composition or vehicle, such as a liquid or solid filler, diluent, excipient, solvent or encapsulating material, involved in carrying or transporting a chemical agent. The preferred composition depends on the method of administration.

The term "therapeutically effective amount" refers to that amount of drug or pharmaceutical agent that will elicit the biological or medical response of a tissue, system or animal that is being sought by a researcher or clinician.

The term "treatment" (and corresponding terms "treat" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to either preventing the onset of a preclinically evident condition altogether or preventing the onset of a preclinical evident stage of a condition in a subject. The term "restorative treatment" refers to treatment that halts the progression of, reduces the pathologic manifestations of, or entirely eliminates a condition in a subject.

B. Carboxypiperidine Compound

In one embodiment, the present invention comprises the compound having the structure:

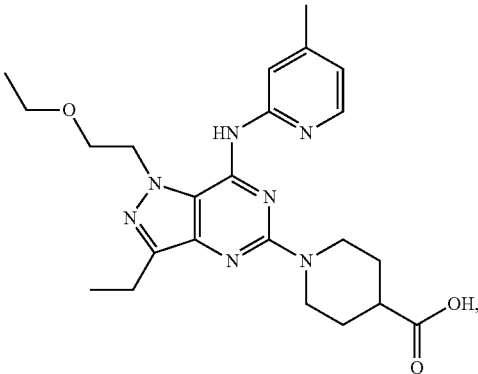 [SMILES: CCOCCn1nc(CC)c2nc(N3CCC(C(=O)O)CC3)nc(Nc3cc(C)ccn3)c21]

and the salts (particularly the pharmaceutically-acceptable salts) of the compound. The corresponding name of this compound is 1-(1-(2-ethoxyethyl)-3-ethyl-7-(4-methylpyridin-2-ylamino)-1H-pyrazolo[4,3-d]pyrimidin-5-yl)piperidine-4-carboxylic acid. Unless otherwise stated, this compound, all tautomeric forms of the compound, and the pharmaceutically-acceptable salts of the compound and its tautomeric forms are collectively referred to in this application as the "Carboxypiperidine Compound". The Carboxypiperidine Compound is useful, for example, as an inhibitor of the PDE5 enzyme.

In one embodiment, the present invention is directed to the free acid form of the Carboxypiperidine Compound.

In another embodiment, the present invention is directed to the pharmaceutically acceptable salts of the Carboxypiperidine Compound.

WO2004096810 reports a genus of compounds that generically embraces the Carboxypiperidine Compound. Although WO2004096810 provides examples of specific compounds within the genus, it does not disclose the Carboxypiperidine Compound itself. The Carboxypiperidine Compound, however, possesses at least one or more different properties relative to the specific compounds described in WO2004096810. These properties include, for example, efficacy (e.g, greater in vitro, ex vivo, and/or in vivo potency), safety (e.g., greater selectivity and/or lower toxicity), pharmacokinetic properties (e.g., $C_{max}$ longer half-life and/or lower clearance), and manufacturing properties (e.g., ease of synthesis and/or availability of starting materials).

C. Salts

As noted above, the Carboxypiperidine Compound may be in either the free acid form or in a salt form. Different salt forms of the Carboxypiperidine Compound may have different physical properties relative to each other. Accordingly, selection of the specific salt form of the Carboxypiperidine Compound potentially can impact, for example, compound stability (such as over a range of temperatures and/or humidities), compound solubility, and other compound physical properties that can affect a drug product. In addition, salts of the Carboxypiperidine Compound generally will have greater aqueous solubility than the corresponding free acid form.

Where the salt of the Carboxypiperidine Compound is administered to a human or animal subject (as opposed to, for example, use for in vitro testing), the salt preferably is a pharmaceutically acceptable salt. The term "pharmaceutically acceptable salt" refers to a salt that is generally considered suitable for human consumption (particularly a non-toxic salt). Pharmaceutically acceptable salts include base addition salts and acid addition salts of the corresponding free acid. These salts typically may be prepared by conventional means from the free acid of the Carboxypiperidine Compound.

Illustrative base addition salts of the Carboxypiperidine Compound include metallic salts and organic salts. Metallic salts include alkali metal (group Ia) salts (such as lithium, sodium and potassium salts), alkaline earth metal (group IIa) salts (such as calcium and magnesium salts), and other physiological acceptable metal salts (such as aluminum and zinc salts). Organic salts include salts made from secondary, tertiary and quaternary amines (such as tromethamine, diethylamine, triethylamine, ethanolamine, diethanolamine, triethanolamine, ethylenediamine, N,N'-dibenzylethylenediamine, meglumine (N-methylglucamine), procaine, chloroprocaine, and choline) and salts made from cationic amino acids (such as arginine, lysine and histidine).

Examples of suitable acid addition salts include, hydrochloride, hydrobromide, hydrofluoride, hydroiodide, borate, fluoroborate, phosphate, hydrogen phosphate, dihydrogen phosphate, glycerophosphate, hexafluorophosphate, metaphosphate, nitrate, bicarbonate, carbonate, bisulphate, sulfate, dodecylsulfate, sulfonate, methanesulfonate, ethanesulfonate, benzenesulfonate, toluenesulfonate, trifluoromethanesulfonate, toluenesulfonate, 2-hydroxyethanesulfonate, cyclohexylaminosulfonate, 2-naphthalesulfonate, camphorsulfonate, acetate, adipate, anthranilate, aspartate, ascorbate, algenate, trifluoroacetate, phenylacetate, benzoate, p-hydroxybenzoate, besylate, butyrate, β-hydroxybutyrate, camphorate, camsyate, citrate, embonate, edisylate, esylate, formate, fumarate, gluconate, digluconate, glycolate, glucamate, glucuronate, gluceptate, heptanoate, glycoheptanoate, hexanoate, hibenzate, isethionate, isethionate, lactate, lactobionate, malate, maleate, mandelate, mesylate, nicotinate, orotate, oxalate, palm itate, pamoate, panthothenate, pectinate, picrate, pivalate, propionate, cyclopentanepropionate, 3-phenylpropionate, pyruvate, saccharate, salicylate, stearate, succinate, sulfanilate, tartrate, galactarate, tosylate, uronate, galacturonate, thiocyanate, and undecanoate.

For a review on suitable salts, see "Handbook of Pharmaceutical Salts: Properties, Selection, and Use" by Stahl and Wermuth (Wiley-VCH, Weinheim, Germany, 2002).

D. Tautomers

As used in this application, the term Carboxypiperidine Compound (as well as the corresponding structure) is intended to embrace all tautomeric isomers of 1-(1-(2-ethoxyethyl)-3-ethyl-7-(4-methylpyridin-2-ylamino)-1H-pyrazolo[4,3-d]pyrimidin-5-yl)piperidine-4-carboxylic acid. Representative tautomeric isomers of the Carboxypiperidine Compound are shown below:

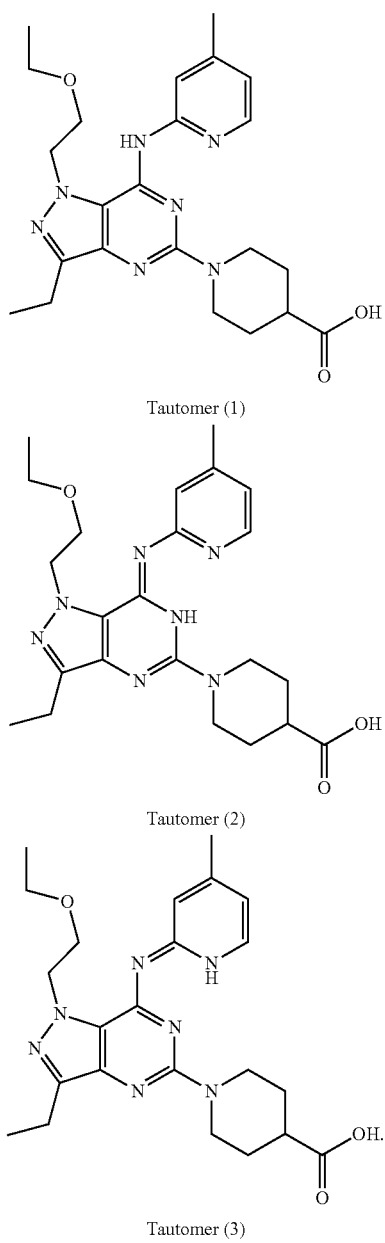

Tautomer (1)

Tautomer (2)

Tautomer (3)

E. Methods of Treatment

The present invention further comprises methods for treating a condition in a subject having or susceptible to having such a condition by administering to the subject a therapeutically-effective amount of the Carboxypiperidine Compound. In one embodiment, the treatment is preventative treatment. In another embodiment, the treatment is palliative treatment. In still another embodiment, the treatment is restorative treatment.

In another embodiment, the condition is a PDE5-mediated condition.

In another embodiment, the condition is a cGMP-mediated condition. A condition in which, for instance, insufficient cGMP is a major component, and whose production or action is modulated in response to the PDE5 enzyme, would therefore be considered a disorder mediated by cGMP.

In another embodiment, the condition is selected from the group consisting of cardiovascular conditions, metabolic conditions, central nervous system conditions, pulmonary conditions, sexual dysfunction, pain and renal dysfunction.

In another embodiment, the condition is a cardiovascular condition selected from the group consisting of hypertension (including essential hypertension, pulmonary hypertension, pulmonary arterial hypertension, secondary hypertension, isolated systolic hypertension, hypertension associated with diabetes, hypertension associated with atherosclerosis, and renovascular hypertension); complications associated with hypertension (including vascular organ damage, congestive heart failure, angina, stroke, glaucoma and impaired renal function); valvular insufficiency; stable, unstable and variant (Prinzmetal) angina; peripheral vascular disease; myocardial infarct; stroke (including stroke recovery); thromboembolic disease; restenosis; arteriosclerosis; atherosclerosis; angiostenosis after bypass; angioplasty (including percutaneous transluminal angioplasty and percutaneous transluminal coronary angioplasty); hyperlipidemia; hypoxic vasoconstriction; vasculitis (including Kawasaki's syndrome); heart failure (including congestive heart failure, decompensated heart failure, systolic heart failure, diastolic heart failure, left ventricular heart failure, right ventricular heart failure, and left ventricular hypertrophy); Raynaud's phenomenon; preeclampsia; pregnancy-induced high blood pressure; cardiomyopathy; and arterial occlusive disorders.

In another embodiment, the condition is hypertension.

In another embodiment, the condition is pulmonary hypertension.

In another embodiment, the condition is pulmonary arterial hypertension.

In another embodiment, the condition is heart failure.

In another embodiment, the condition is diastolic heart failure.

In another embodiment, the condition is systolic heart failure.

In another embodiment, the condition is angina.

In another embodiment, the condition is thrombosis.

In another embodiment, the condition is stroke (including stroke recovery).

In another embodiment, the condition is a condition associated with endothelial dysfunction (including conditions selected from the group consisting of atherosclerotic lesions, myocardial ischaemia, peripheral ischaemia, valvular insufficiency, pulmonary arterial hypertension, angina, clots, vascular complications after vascular bypass, vascular dilation, vascular repermeabilisation, and heart transplantation).

In another embodiment, the condition is a metabolic condition selected from the group consisting of Syndrome X; diabetes (including type I and type II diabetes); insulin resistance; syndromes of insulin resistance (including insulin receptor disorders, Rabson-Mendenhall syndrome, leprechaunism, Kobberling-Dunnigan syndrome, Seip syndrome, Lawrence syndrome, Cushing syndrome, acromegaly, pheochomocytoma, glucagonoma, primary aldosteronism, somatostatinoma, Lipoatrophic diabetes, β-cell toxin induced diabetes, Grave's disease, Hashimoto's thyroiditis and idiopathic Addison's disease); impaired glucose tolerance; diabetic complications (including diabetic gangrene, diabetic arthropathy, diabetic nephropathy, diabetic glomerulosclerosis, diabetic deramatopathy, diabetic neuropathy, peripheral diabetic neuropathy, diabetic cataract, and diabetic retinopathy); hyperglycemia; and obesity.

In another embodiment, the condition is insulin resistance.

In another embodiment, the condition is nephropathy.

In another embodiment, the condition is a central nervous system condition selected from the group consisting of vascular dementia; craniocerebral trauma; cerebral infarct; cerebrovascular accident, dementia; concentration disorders; Alzheimer's disease; Parkinson's disease; amyolateral sclerosis; Huntington's disease; multiple sclerosis; Creutzfeld-Jacob disease; anxiety; depression; sleep disorders; and migraine.

In another embodiment, the condition is Alzheimer's disease.

In another embodiment, the condition is Parkinson's disease.

In another embodiment, the condition is amyolateral sclerosis.

In another embodiment, the condition is a concentration disorder.

In another embodiment, the condition is a pulmonary condition selected from the group consisting of asthma; acute respiratory distress; cystic fibrosis; chronic obstructive pulmonary disease; bronchitis; and chronic reversible pulmonary obstruction.

In another embodiment, the condition is pain. In another embodiment, the condition is acute pain. Examples of acute pain include acute pain associated with injury or surgery. In another embodiment, the condition is chronic pain. Examples of chronic pain include neuropathic pain (including postherpetic neuralgia and pain associated with peripheral, cancer or diabetic neuropathy), carpal tunnel syndrome, back pain (including pain associated with herniated or ruptured intervertabral discs or abnormalities of the lumber facet joints, sacroiliac joints, paraspinal muscles or the posterior longitudinal ligament), headache, cancer pain (including tumour related pain such as bone pain, headache, facial pain or visceral pain) or pain associated with cancer therapy (including postchemotherapy syndrome, chronic postsurgical pain syndrome, post radiation syndrome, pain associated with immunotherapy, or pain associated with hormonal therapy), arthritic pain (including osteoarthritis and rheumatoid arthritis pain), chronic post-surgical pain, post herpetic neuralgia, trigeminal neuralgia, HIV neuropathy, phantom limb pain, central post-stroke pain and pain associated with chronic alcoholism, hypothyroidism, uremia, multiple sclerosis, spinal cord injury, Parkinson's disease, epilepsy and vitamin deficiency. In another embodiment, the condition is nociceptive pain (including pain from central nervous system trauma, strains/sprains, burns, myocardial infarction and acute pancreatitis, post-operative pain (pain following any type of surgical procedure), posttraumatic pain, renal colic, cancer pain and back pain). In another embodiment, the condition is pain associated with inflammation (including arthritic pain (such as osteoarthritis and rheumatoid disease pain), ankylosing spondylitis, visceral pain (including inflammatory bowel disease, functional bowel disorder, gastro-esophageal reflux, dyspepsia, irritable bowel syndrome, functional abdominal pain syndrome, Crohn's disease, ileitis, ulcerative colitis, dysmenorrheal, cystitis, pancreatitis and pelvic pain). In another embodiment, the condition is pain resulting from musculo-skeletal disorders (including myalgia, fibromyalgia, spondylitis, seronegative (non-rheumatoid) arthropathies, non-articular rheumatism, dystrophinopathy, glycogenolysis, polymyositis and pyomyositis). In another embodiment, the condition is selected from the group consisting of heart and vascular pain (including pain caused by angina, myocardical infarction, mitral stenosis, pericarditis, Raynaud's phenomenon, scleredoma and skeletal muscle ischemia).

In another embodiment, the condition is selected from the group consisting of head pain (including migraine such as migraine with aura and migraine without aura), cluster headache, tension-type headache mixed headache and headache associated with vascular disorders; orofacial pain, including dental pain, otic pain, burning mouth syndrome and temporomandibular myofascial pain).

In another embodiment, the condition is sexual dysfunction (including sexual dysfunction selected from the group consisting of impotence (organic or psychic); male erectile dysfunction; clitoral dysfunction; sexual dysfunction after spinal cord injury; female sexual arousal disorder; female sexual orgasmic dysfunction; female sexual pain disorder; and female hypoactive sexual desire disorder).

In another embodiment, the condition is male erectile dysfunction.

In another embodiment, the condition is renal dysfunction (including renal dysfunction selected from the group consisting of acute renal failure, chronic renal failure; nephropathy (such as diabetic nephropathy); tubulointerstitial disorders; glomerulopathy; and nephritis. In another embodiment, the condition is a cancer condition selected from the group consisting of cancerous cachexia; tumor metastasis and neoplasia.

In another embodiment, the condition is osteoporosis.

In another embodiment, the condition is a gastrointestinal condition selected from the group consisting of nutcracker oesophagus; anal fissure; disorders of gut motility; irritable bowel syndrome and haemorrhoids. In another embodiment, the condition is a urologic condition selected from the group consisting of bladder outlet obstruction; incontinence and benign prostatic hyperplasia.

In another embodiment, the condition is a skin condition, selected from psoriasis; urticaria and skin necrosis.

In another embodiment, the condition is an ophthalmic condition selected from retinal disease; macular degeneration and glaucoma.

In another embodiment, the condition is nitrate intolerance.

In another embodiment, the condition is baldness.

In another embodiment, the condition is a gynecologic condition selected from the group consisting of dysmenorrhoea (primary and secondary); infertility and premature labor. In another embodiment, the condition is secondary dysmenorrhoea.

In another embodiment, the present invention further comprises methods for inducing weight loss or maintenance of weight loss in a subject by administering to the subject a therapeutically-effective amount of the Carboxypiperidine Compound.

F. Subjects

The Carboxypiperidine Compound (including the corresponding methods of treatment and pharmaceutical compositions) are suitable for use with, for example, mammalian subjects such as humans, other primates (e.g., monkeys, chimpanzees), companion animals (e.g., dogs, cats, horses), farm animals (e.g., goats, sheep, pigs, cattle), laboratory animals (e.g., mice, rats), and wild and zoo animals (e.g., wolves, bears, deer). In one embodiment, the subject is a mammalian subject. In another embodiment, the subject is a human.

G. Hypothesized Mechanism

Without being held to a particular theory, it is hypothesized that the Carboxypiperidine Compound is an inhibitor of the PDE5 enzyme. It is further hypothesized that the Carboxypiperidine Compound inhibits the action of the PDE5 enzyme leading to an increase in intracellular cGMP levels. This increase in intracellular cGMP levels reduces intracellular calcium signaling, which in turn results in vascular smooth muscle relaxation and a reduction in blood pressure.

H. Administration and Dosing

The Carboxypiperidine Compound is generally administered in a therapeutically effective amount. In one embodiment, the Carboxypiperidine Compound is administered in a PDE5 enzyme inhibiting amount. The Carboxypiperidine Compound can be administered by any suitable route in the form of a pharmaceutical composition adapted to such a route, and in a dose effective for the treatment intended. Therapeutically effective doses of the Carboxypiperidine Compound required to prevent or arrest the progress of, or to treat the medical condition, are readily ascertained by one of ordinary skill in the art using preclinical and clinical approaches familiar to the medicinal arts.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary based on the specific situation. Dosage levels from about 0.001 mg to about 100 mg of Carboxypiperidine Compound per kilogram of body weight per day are useful in the treatment of the above-indicated conditions. In one embodiment, the total daily dose of the Carboxypiperidine Compound (administered in single or divided doses) is typically from about 0.001 mg/kg to about 20 mg/kg (i.e., mg compound/kg body weight). In another embodiment, the total daily dose of the Carboxypiperidine Compound is from about 0.005 mg/kg to about 10 mg/kg. In another embodiment, the total daily dose is from about 0.005 mg/kg to about 5 mg/kg. In another embodiment, the total daily dose is from about 0.01 mg/kg to about 1 mg/kg. These dosages are based on an average human subject having a weight of about 65 kg to about 75 kg. A physician will readily be able to determine doses for subjects whose weight falls outside of this range, such as infants. The administration of the Carboxypiperidine Compound can be repeated a plurality of times in a day (typically no greater than 4 times) to achieve the desired daily dose.

For convenience the Carboxypiperidine Compound can be administered in a unit dosage form. If desired, multiple doses per day of the unit dosage form can be used to increase the total daily dose. The unit dosage form, for example, may be a tablet or capsule containing about 0.01, 0.05, 0.1, 0.5, 1, 5, 10, 15, 20, 25, 30, 35, 40, 45, 50, 55, 60, 65, 70, 75, 80, 85, 90, 95, 100, 125, 150, 175, 200, 250 or 500 mg of the Carboxypiperidine Compound. In one embodiment, the unit dosage form contains from about 0.01 mg to about 500 mg of the Carboxypiperidine Compound. In another embodiment, the unit dosage form contains from about 0.05 mg to about 250 mg of the Carboxypiperidine Compound. In another embodiment, the unit dosage form contains from about 0.1 mg to about 100 mg of the Carboxypiperidine Compound. In another embodiment, the unit dosage form contains from about 0.5 mg to about 50 mg of the Carboxypiperidine Compound.

I. Use in the Preparation of a Medicament

In another embodiment, the present invention comprises the Carboxypiperidine Compound for use as a medicament (such as a unit dosage tablet or unit dosage capsule).

The present invention further comprises the use of the Carboxypiperidine Compound for the manufacture of a medicament (such as a unit dosage tablet or unit dosage capsule) to treat one or more of the conditions previously identified in the above sections discussing methods of treatment. In one embodiment, the condition is hypertension.

J. Pharmaceutical Compositions

For the treatment of the conditions referred to above, the Carboxypiperidine Compound can be administered as the free acid compound per se. In another embodiment, the Carboxypiperidine Compound can be administered as one or more pharmaceutically acceptable salts of the free acid compound per se. In another embodiment, the Carboxypiperidine Compound can be administered as a mixture of the free acid compound per se and one or more pharmaceutically acceptable salts of the free acid compound per se.

The present invention further comprises pharmaceutical compositions comprising the Carboxypiperidine Compound. In one embodiment, the pharmaceutical composition comprises the Carboxypiperidine Compound in the free acid form. In another embodiment, the pharmaceutical composition comprises one or more pharmaceutically acceptable salts of the Carboxypiperidine Compound. In another embodiment, the pharmaceutical composition comprises a mixture of the Carboxypiperidine Compound in the free acid form and one or more pharmaceutically acceptable salts of the Carboxypiperidine Compound. In one embodiment, the pharmaceutical composition comprises the Carboxypiperidine Compound and at least one pharmaceutically-acceptable carrier. The carrier can be a solid, a liquid, or both, and may be formulated with the Carboxypiperidine Compound as a unit dosage form, for example, a tablet, which can contain from 0.05% to 95% by weight of the Carboxypiperidine Compound. Other pharmacologically active substances can also be present.

The Carboxypiperidine Compound may be administered by any suitable route, preferably in the form of a pharmaceutical composition adapted to such a route, and in a dose effective for the treatment intended. The Carboxypiperidine Compound and corresponding compositions, for example, may be administered orally, rectally, parenterally, or topically.

Oral administration of a solid dosage form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the Carboxypiperidine Compound is ordinarily combined with one or more adjuvants. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dosage form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Formulations suitable for topical administration to the eye include, for example, eye drops wherein the compound of this invention is dissolved or suspended in suitable carrier. For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant.

In another embodiment, the present invention comprises a rectal dosage form. Such rectal dose form may be in the form of, for example, a suppository.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., Handbook of Pharmaceutical Excipients ($3^{rd}$ Ed.), American Pharmaceutical Association, Washington, 1999.

K. Combinations and Combination Therapy

The Carboxypiperidine Compound also can be administered in combination with other therapeutic agents to treat the various conditions previously discussed above. The Carboxypiperidine Compound and the other therapeutic agent(s) may be may be administered simultaneously (either in the same dosage form or in separate dosage forms) or sequentially. Accordingly, in one embodiment, the present invention comprises methods for treating a condition in a subject having or susceptible to having such a condition by administering to the subject a therapeutically-effective amount of the Carboxypiperidine Compound and one or more additional therapeutic agents. In another embodiment, the present invention comprises a pharmaceutical composition comprising the Carboxypiperidine Compound, one or more additional therapeutic agents, and a pharmaceutically acceptable carrier.

In one embodiment, the Carboxypiperidine Compound may be administered with aspirin.

In another embodiment, the Carboxypiperidine Compound may be co-administered with one or more diuretics. Examples of suitable diuretics include hydroclorothiazide (such as MICROZIDE™ and ORETIC™), hydroflumethiazide (such as SALURON™), bemetanide (such as BUMEX™), torsemide (such as DEMADEX™), metolazone (such as ZAROXOLYN™), chlorothiazide (such as DIURIL™, ESIDRIX™ and HYDRODIURIL™), triamterene (such as DYRENIUM™), ethacrynic acid (such as EDECRIN™), chlorthalidone (such as HYGROTON™), furosemide (such as LASIX™), indapamide (such as LOZOL™), and amiloride (such as MIDAMOR™ and MODURETIC™).

In another embodiment, the Carboxypiperidine Compound may be co-administered with one or more angiotensin converting enzyme inhibitors. Examples of suitable angiotensin converting enzyme inhibitors include quinapril (such as ACCUPRIL™), perindopril (such as ACEON™), captopril (such as CAPOTEN™), enalapril (such as VASOTEC™), ENALAPRILAT™, ramipril (such as ALTACE™), cilazapril, delapril, fosenopril (such as MONOPRIL™), zofenopril, indolapril, benazepril (such as LOTENSIN™), lisinopril (such as PRINIVIL™ and ZESTRIL™), spirapril, trandolapril (such as MAVIK™), perindep, pentopril, moexipril (such as UNIVASC™), fasidotril, S-allymercaptocaptopril, and pivopril.

In another embodiment, the Carboxypiperidine Compound may be co-administered with one or more angiotensin II receptor blockers. Examples of suitable angiotensin II receptor blockers include candesartan (such as ATACAND™), eprosartan (such as TEVETEN™), irbesartan (such as AVEPRO™), losartan (such as COZAAR™), olmesartan, olmesartan medoxomil (such as BENICAR™), tasosartan, telmisartan (such as MICARDIS™), valsartan (such as DIOVAN™), zolasartan, FI-6828K, RNH-6270, UR-7198, Way-126227, KRH-594, TAK-536, BRA-657, and TA-606.

In another embodiment, the Carboxypiperidine Compound may be co-administered with one or more calcium channel blockers. Examples of suitable calcium channel blockers include nifedipine (such as ADALAT™, ADALAT CC™ and PROCARDIA™), verapamil (such as CALAN™, COVERA-HS™, ISOPTIN SR™ and VERELAN™), diltiazem (such as CARDIZEM™ CARDIZEM CD™, CARDIZEM LA™, CARDIZEM SR™, DILACOR™, TIAMATE™ and TIAZAC™), isradipine (such as DYNACIRC™ and DYNACIRC CR™), amiodipine (such as NORVASC™), felodipine (such as PLENDIL™), nisoldipine (such as SULAR™), bepridil (such as VASCOR™), vatanidipine, clevidipine, lercanidipine, dilitiazem, and NNC-55-0396.

In another embodiment, the Carboxypiperidine Compound may be co-administered with one or more beta blockers. Examples of suitable beta blockers include timolol (such as BLOCARDEN™), carteolol (such as CARTROL™), carvedilol (such as COREG™), nadolol (such as CORGARD™), propranolol (such as INNOPRAN XL™), betaxolol (such as KERLONE™), penbutolol (such as LEVATOL™), metoprolol (such as LOPRESSOR™ and TOPROL-XL™), atenolol (such as TENORMIN™), pindolol (such as VISKEN™), and bisoprolol.

In another embodiment, the Carboxypiperidine Compound may be co-administered with one or more alpha blockers. Examples of suitable alpha blockers include prazosin, doxazosin (such as CARDURA™), phenoxybenzamine (such as DIBENZYLINE™), terazosin (such as HYTRIN™), CDRI-93/478 and CR-2991.

In another embodiment, the Carboxypiperidine Compound may be co-administered with one or more alpha-beta blockers. An example of a suitable alpha-beta blocker is labetalol (such as NORMODYNE™ or TRANDATE™).

In another embodiment, the Carboxypiperidine Compound may be co-administered with one or more aldosterone receptor antagonists. Examples of suitable aldosterone receptor antagonists include eplerenone (such as INSPRA™) and spironolactone (such as ALDACTONE™).

In another embodiment, the Carboxypiperidine Compound may be co-administered with one or more renin inhibitors. Examples of suitable renin inhibitors include aliskiren (SPP 100), SPP-500/600 and YS-004-39.

In another embodiment, the Carboxypiperidine Compound may be co-administered with one or more central antiadrenergics. Examples of suitable central antiadrenergics includes methyldopa (such as ALDOMET™), clonidine (such as CATAPRES™ or CATAPRES-TTS™), guanfacine (such as TENEX™), and guanabenz (such as WYTENSIN™).

In another embodiment, the Carboxypiperidine Compound may be co-administered with one or more glycosides/inotropic agents. An example of a suitable glycoside/inotropic agent is digoxin (such as LANOXIN™).

In another embodiment, the Carboxypiperidine Compound may be co-administered with one or more human B-type natriuretic peptides. An example of a suitable human B-type natriuretic peptide is nesiritide (such as NATRECOR™).

In another embodiment, the Carboxypiperidine Compound may be co-administered with one or more organic nitrates or nitric oxide donors. "Nitric oxide donor" refers to a compound that donates, releases and/or directly or indirectly transfers a nitrogen monoxide species, and/or stimulate the endogenous production of nitric oxide or endothelium-derived relaxing factor (EDRF) in vivo and/or elevate endogenous levels of nitric oxide or EDRF in vivo. It also includes compounds that are substrates for nitric oxide synthase. Examples of suitable nitric oxide donors include S-nitrosothiols, nitrites, nitrates, N-oxo-N-nitrosamines. SPM 3672, SPM 5185, SPM 5186 and analogues thereof, sodium nitroprusside, nitroglycerin, isosorbide dinitrate, isosorbide mononitrate, molsidomine, SIN-1 and substrates of the various isozymes of nitric oxide synthase.

In another embodiment, the Carboxypiperidine Compound may be co-administered with one or more bradykinin agonists.

In another embodiment, the Carboxypiperidine Compound may be co-administered with one or more soluble guanylate cyclase activators. An example of a suitable soluble guanylate cyclase activator is BAY-41-8543.

In another embodiment, the Carboxypiperidine Compound may be co-administered with one or more neutral endopeptidase inhibitors. Examples of suitable neutral endopeptidase inhibitors include omapatrilat, fasidotril, mixanpril, sampatrilat, Z13752A,

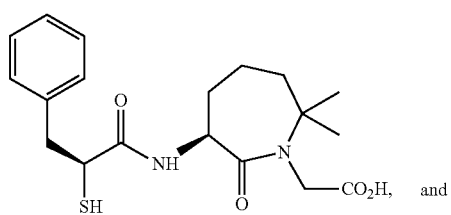

BMS-189921

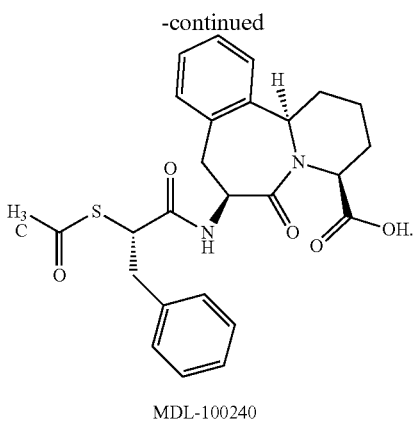

MDL-100240

In another embodiment, the Carboxypiperidine Compound may be co-administered with one or more endothelian antagonists. Examples of suitable endothelin antagonists include ambrisentan, darusentan, J-104132, SPP-301, TBC-3711, YM-62899, YM-91746 and BMS-193884.

In another embodiment, the Carboxypiperidine Compound may be co-administered with one or more 3-hydroxy-3-methylglutaryl coenzyme A reductase inhibitors. Examples of suitable 3-hydroxy-3-methylglutaryl coenzyme A reductase inhibitors include fluvastatin (such as LESCOL™), atorvastatin (such as LIPITOR™), lovastatin (such as ALTOCOR™ or MEVACOR™), pravastatin (such as PRAVACHOL™), rosuvastatin (such as CRESTOR™), and simvastatin (such as ZOCOR™).

In another embodiment, the Carboxypiperidine Compound may be co-administered with niacin or one or more nicotinic acid derivatives. Examples of suitable niacin or nicotinic acid derivatives include NIACOR™, NIASPAN™, NICOLAR™, and SLO-NIACIN™.

In another embodiment, the Carboxypiperidine Compound may be co-administered with one or more fibric acid derivatives. Examples of suitable fibric acid derivatives include clofibrate (such as ATROMID-S™), gemfibrozil (such as LOPID™), and fenofibrate (such as TRICOR™).

In another embodiment, the Carboxypiperidine Compound may be co-administered with one or more bile acid sequestants. Examples of suitable bile acid sequestants include colestipol (such as COLESTID™), cholestyramine (such as LOCHOLEST™, PREVALITE™, QUESTRAN™, and QUESTRAN LIGHT™), colesevelam (such as WELCHOL™).

In another embodiment, the Carboxypiperidine Compound may be co-administered with one or more cholesterol absorption inhibitors. An example of a suitable cholesterol absorption inhibitor is ezetimibe (such as ZETIA™).

In another embodiment, the Carboxypiperidine Compound may be co-administered with one or more cholesteryl ester transport protein inhibitors. An example of a suitable cholesteryl ester transport protein inhibitor is torcetrapib.

In another embodiment, the Carboxypiperidine Compound may be co-administered with one or more apical sodium-dependent bile acid cotransporter inhibitors. Examples of suitable apical sodium-dependent bile acid cotransporter inhibitors include SD-5613, AZD7806 and 264W94.

In another embodiment, the Carboxypiperidine Compound may be co-administered with one or more alpha glucosidase inhibitors. Examples of suitable alpha glucosidase inhibitors include miglitol (such as GLYSET™) and acarbose (such as PRECOSE™).

In another embodiment, the Carboxypiperidine Compound may be co-administered with one or more biguanides. Examples of suitable biguanides include rosiglitazone (such as AVANDAMET™) and metformin (such as GLUCOPHAGE™ and GLUCOPHAGE XR™).

In another embodiment, the Carboxypiperidine Compound may be co-administered with one or more insulins. Examples of suitable insulins include HUMALOG™, HUMALOG 50/50™, HUMALOG 75/25™, HUMULIN 50/50™, HUMALIN 75/25™, HUMALIN L™, HUMALIN N™, HUMALIN R™, HUMALIN R-U500™, HUMALIN U™, ILETIN II LENTE™, ILETIN II NPH™, ILETIN II REGULAR™, LANTUS™, NOVOLIN 70/30™, NOVILIN N™, NOVILIN R™, NOVOLOG™, VELOSULIN BR™, and EXUBERA™.

In another embodiment, the Carboxypiperidine Compound may be co-administered with one or more meglitnides. Examples of suitable meglitnides include repaglinide (such as PRANDIN™) and nateglinide (such as STARLIX™).

In another embodiment, the Carboxypiperidine Compound may be co-administered with one or more sulfonylureas. Examples of suitable sulfonylureas include glimepiride (such as AMARYL™), glyburide (such as DIABETA™, GLYNASE PRESTAB™ or MICRONASE™), and glipizide (such as GLUCOTROL™ and GLUCOTROL XL™).

In another embodiment, the Carboxypiperidine Compound may be co-administered with one or more thiazolidinediones. Examples of suitable thiazolidinediones include pioglitazone (such as ACTOS™) and rosiglitazone (such as AVANDIA™).

In another embodiment, the Carboxypiperidine Compound may be co-administered with one or more alpha-2-delta ligands. Examples of suitable alpha-2-delta ligands include gabapentin, pregabalin (such as LYRICA™), [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)-(3-amino-methyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid), (2S,4S)-4-(3-Chlorophenoxy)praline, and (2S,4S)-4-(3-Fluorobenzyl)praline.

L. Kits

The present invention further comprises kits that are suitable for use in performing the methods of treatment described above. In one embodiment, the kit comprises a first dosage form comprising the Carboxypiperidine Compound and a container for the first dosage form. In another embodiment, the kit comprises a first dosage form comprising the Carboxypiperidine Compound and a second dosage form comprising a second therapeutic agent.

In another embodiment, the kit comprises a first dosage form comprising the Carboxypiperidine Compound and a second dosage form comprising an angiotensin converting enzyme inhibitor.

In another embodiment, the kit comprises a first dosage form comprising the Carboxypiperidine Compound and a second dosage form comprising an angiotensin II receptor antagonist.

In another embodiment, the kit comprises a first dosage form comprising the Carboxypiperidine Compound and a second dosage form comprising an aldosterone receptor antagonist.

In another embodiment, the kit comprises a first dosage form comprising the Carboxypiperidine Compound and a second dosage form comprising a nitric oxide donor.

M. Compound Synthesis

The Carboxypiperidine Compound may be prepared using the methods illustrated in the synthetic schemes and the experimental procedures described below. The general synthetic schemes are presented for purposes of illustration and are not intended to be limiting. The starting materials used to prepare the Carboxypiperidine Compound are commercially available or may be prepared by routine methods well known to those of ordinary skill in the art (such as those methods disclosed in standard reference books such as the COMPENDIUM OF ORGANIC SYNTHETIC METHODS, Vol. I-VI (published by Wiley-Interscience)).

Scheme 1
Scheme 1 outlines a general procedure for the preparation of the free acid of the Carboxypiperidine Compound.

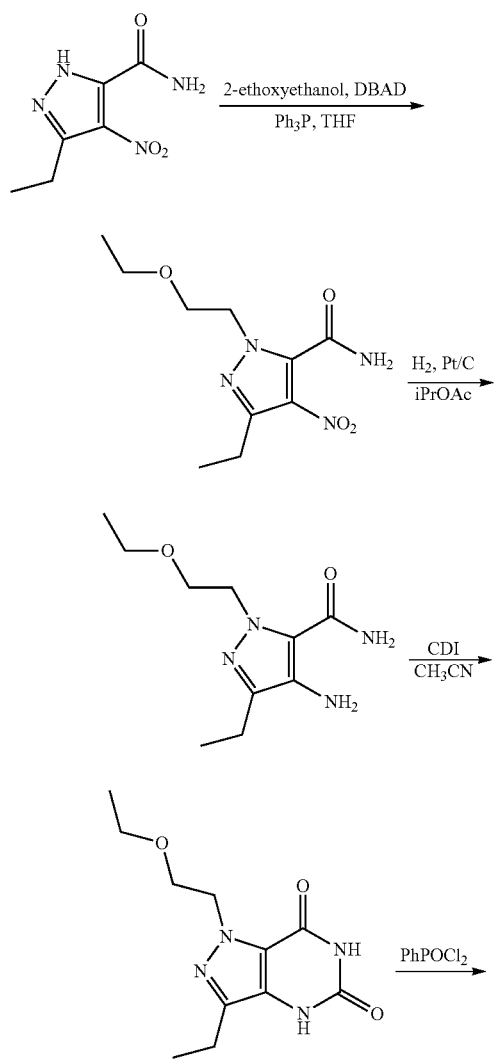

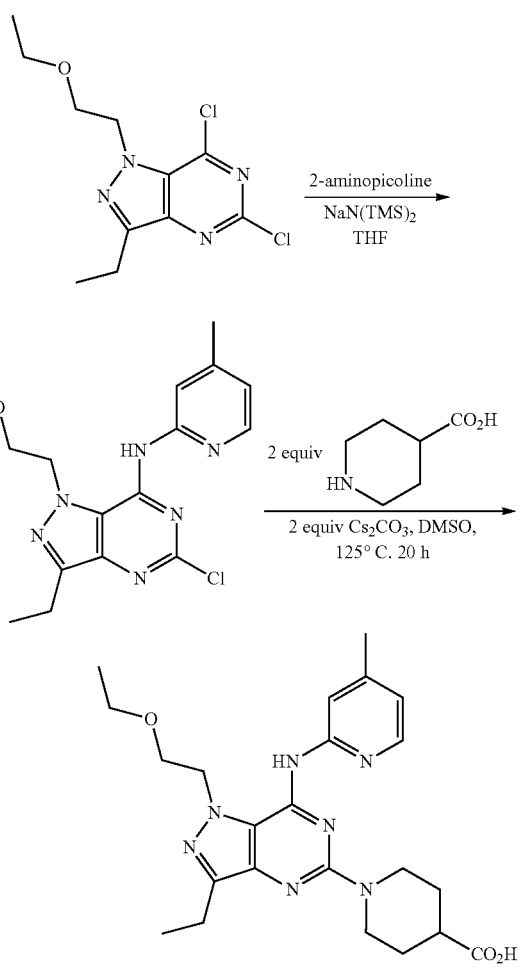

Scheme 2
Scheme 2 outlines an alternative general procedure for the preparation of the free acid of the Carboxypiperidine Compound.

19
-continued

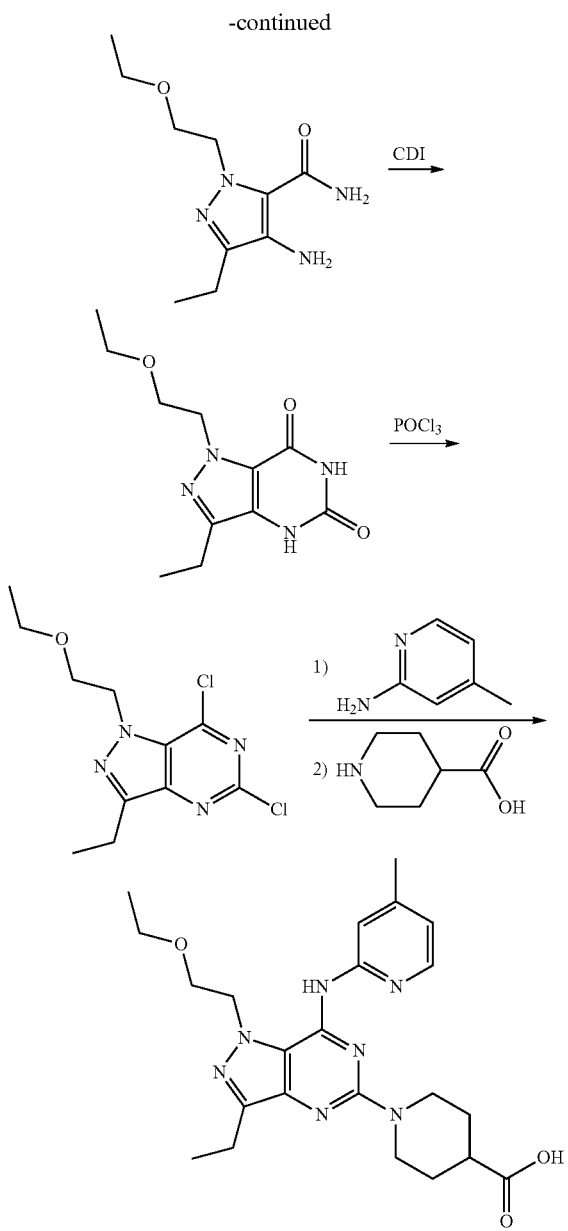

The following examples illustrate the synthesis of the free acid of the Carboxypiperidine Compound:

EXAMPLE 1

20

1-(1-(2-ethoxyethyl)-3-ethyl-7-(4-methylpyridin-2-ylamino)-1H-pyrazolo[4,3-d]pyrimidin-5-yl)piperidine-4-carboxylic acid Step 1: Preparation of 1-(2-ethoxyethyl)-3-ethyl-4-nitro-1H-pyrazole-5-carboxamide

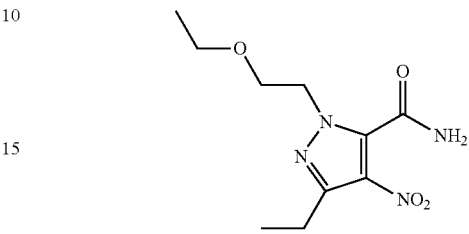

A 1 L flask was charged with 3-ethyl-4-nitropyrazole-5-carboxamide (prepared as described in EP 1176142 at page 18) (15.0 g, 81 mmol), triphenylphosphine (25.6 g, 97.8 mmol), and tetrahydrofuran (120 mL). The resulting mixture was cooled by placing the flask in a 0° C. bath and 2-ethoxyethanol (9.5 ml, 98 mmol) was added to the flask. A solution of di-tert-butyl azodicarboxylate (22.5 g, 97.8 mmol) in tetrahydrofuran (90 mL) was then added to the flask over a period of 2.5 hours. The mixture was stirred with cooling for an additional hour and then warmed to room temperature and stirred for one additional hour. The mixture was again cooled to 0° C., treated with 6M hydrochloric acid (40 ml), and heated to 40° C. for one hour. The mixture was partially concentrated and extracted between ethyl acetate and water. The aqueous layer was back-extracted with ethyl acetate. The combined organic layers were washed with water, washed with brine, dried over magnesium sulfate, filtered and then concentrated. The resulting viscous oil was treated with 2-propanol and this mixture was then concentrated. The resulting material was treated with 2-propanol and heated. Upon cooling, the resulting crystals were filtered, rinsed with cold 2-propanol, and dried to afford 16.5 g of the title compound.

Step 2: Preparation of 4-amino-1-(2-ethoxyethyl)-3-ethyl-1H-pyrazole-5-carboxamide

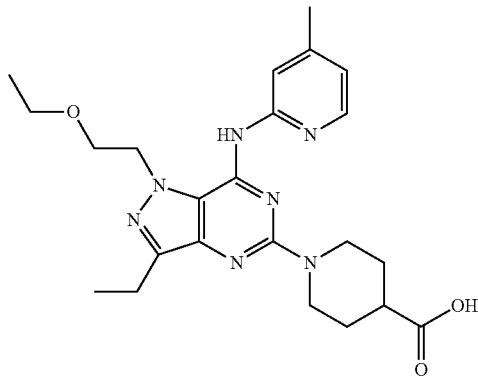 [SMILES: CCOCCn1nc(CC)c2nc(N3CCC(C(=O)O)CC3)nc(Nc3cc(C)ccn3)c21]

1-(2-ethoxyethyl)-3-ethyl-4-nitro-1H-pyrazole-5-carboxamide from step 1 (15.0 g, 58 mmol), 5% Platinum-on-carbon (0.75 g), and isopropyl acetate (150 mL) were combined and the mixture was stirred under 80 psi of hydrogen for about 50 hours. The mixture was then filtered through celite, the celite was rinsed with acetonitrile, and the filtrate was concentrated. The material eventually crystallized to give 13.7 g as a hydrate of the title compound.

Step 3: 1-(2-ethoxyethyl)-3-ethyl-1H-pyrazolo[4,3-d]pyrimidine-5,7(4H,6H)-dione

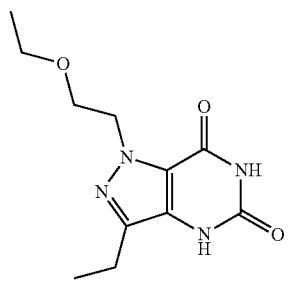 [SMILES: CCOCCn1nc(CC)c2[nH]c(=O)[nH]c(=O)c21]

A mixture of carbonyldiimidazole (12.3 g, 76.1 mmol) in acetonitrile (123 mL) was warmed to 50° C. The 4-amino-1-(2-ethoxyethyl)-3-ethyl-1H-pyrazole-5-carboxamide prepared in step 3 (13.2 g, 58 mmol) was added to the mixture over a period of one hour and the temperature of the mixture was increased to 75° C. during the addition. The mixture was then cooled and stirred overnight. The mixture was cooled in an ice bath and filtered. The filter cake was rinsed with water and dried to provide 12.8 g of the title compound.

Step 4: Preparation of 5,7-dichloro-1-(2-ethoxyethyl)-3-ethyl-1H-pyrazolo[4,3-d]pyrimidine

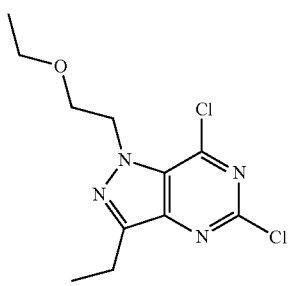 [SMILES: CCOCCn1nc(CC)c2nc(Cl)nc(Cl)c21]

A mixture of 1-(2-ethoxyethyl)-3-ethyl-1H-pyrazolo[4,3-d]pyrimidine-5,7(4H,6H)-dione from step 3 (25.2 g, 100 mmol) was treated with $PhPOCl_2$ (195 g, 1000 mmol) and heated, under N2, with stirring at 135° C. for 20 h. The mixture was cooled and then heated at 140° C. for an additional 20 h. The mixture was cooled and slowly added to an ice (600 g)/water (200 mL) mixture. This was stirred for 3 h and the resulting solid was collected by filtration and rinsed with water (2×100 mL). The solid was suspended in ethyl acetate (300 mL). Water (200 mL) was added and the pH adjusted to 1-2. Then 10% $NaHCO_3$ (125 mL) was added (resulting in pH ~7) and the layers were separated. The organic layer was successively washed with water (400 mL) and saturated sodium chloride solution (150 mL). The organic solution was then dried, and concentrated to provide 23 g of the title compound.

Step 5: Preparation of N-[5-chloro-1-(2-ethoxyethyl)-3-ethyl-1H-pyrazolo[4,3-d]pyrimidin-7-yl]-4-methylpyridin-2-ylamine

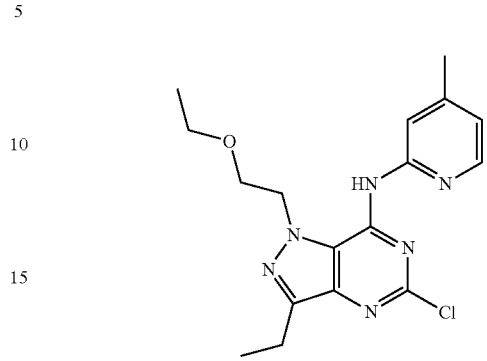

A mixture of 2-amino-4-picoline (4.32 g, 40 mmol) and 5,7-dichloro-1-(2-ethoxyethyl)-3-ethyl-1H-pyrazolo[4,3-d]pyrimidine from step 4 (5.78 g, 20 mmol) was treated with THF (25 mL) and cooled to 0° C. The mixture was stirred and treated with 1 M $LiN(TMS)_2$ in THF (40 mL, 40 mmol) at a rate such that the temperature was kept below 5° C. The mixture was stirred for 30 min and was then treated with 10% citric acid solution until pH 6-7 was achieved. The mixture was partially concentrated under reduced pressure. The mixture was then stirred at 5° C. for 1 h. The resulting solid was collected by suction filtration and washed with water (40 mL). The solid was dried in a vacuum oven at a temperature less than 60° C. to afford 7.0 g of the title compound.

Step 6: Preparation of 1-(1-(2-ethoxyethyl)-3-ethyl-7-(4-methylpyridin-2-ylamino)-1H-pyrazolo[4,3-d]pyrimidin-5-yl)piperidine-4-carboxylic acid

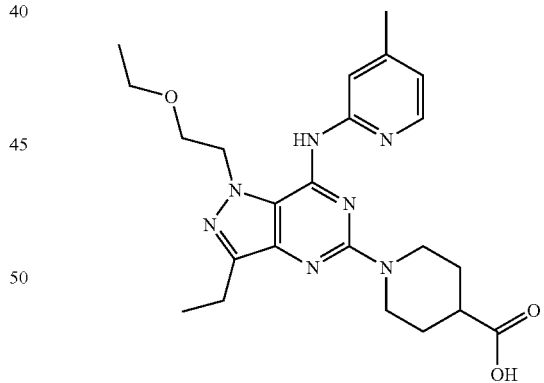

A mixture of N-[5-chloro-1-(2-ethoxyethyl)-3-ethyl-1H-pyrazolo[4,3-d]pyrimidin-7-yl]-4-methylpyridin-2-ylamine from step 5 (5.42 g, 166 mmol), isonipecotic acid (85.9 g, 665 mmol), cesium carbonate (162 g, 498 mmol), and DMSO (55 mL) was heated, with stirring, at 125° C. After 20 h, the mixture was cooled to 20° C. and water (165 mL) was added. The mixture was stirred for 15 min and was then treated with ethyl acetate (55 mL). The layers were separated and the aqueous was treated with another portion of ethyl acetate (55 mL). The layers were separated again and the aqueous layer was taken to pH ~5 using 6 M HCl. After stirring for 1 hour, the resulting solid was filtered, washed with water (20 mL)

and dried in vacuuo, to give 5.5 g of the title compound. $^1$H NMR (400 MHz, DMSO-$d_6$): δ 1.10 (t, 3 H), 1.30 (t, 3 H), 1.49-1.60 (m, 2 H), 1.84-1.95 (m, 2 H), 2.32-2.36 (m, 3 H), 2.52-2.57 (m, 1 H), 2.78 (q, 2 H), 2.99-3.08 (m, 2 H), 3.52 (q, 2 H), 3.78 (t, 2 H), 4.45-4.53 (m, 2 H), 4.56-4.64 (m, 2 H), 6.91 (d, 1 H), 8.05 (s, 1 H), 8.18 (d, 1 H), 9.63 (s, 1 H), 12.18 (s, 1 H). LCMS m/z 454.

Alternatively, a mixture of N-[5-chloro-1-(2-ethoxyethyl)-3-ethyl-1H-pyrazolo[4,3-d]pyrimidin-7-yl]-4-methylpyridin-2-ylamine from step 5 can be combined with isonipecotic acid (between 1 to 10 equivalents) and a base and heated between 100-125° C. in a solvent until the reaction is complete. Suitable bases include cesium carbonate, sodium carbonate and potassium carbonate. Suitable solvents include DMSO and N,N-dimethylformamide. Upon cooling, water can be added and the basic solution extracted (between 1 to 3 times) with an organic solvent such as ethyl acetate. The remaining basic layer is acidified to pH 5 with HCl. The mixture is stirred for approximately 1 hour. The solid is filtered off, washed with water, and dried in vaccuo to provide the title compound.

EXAMPLE 2

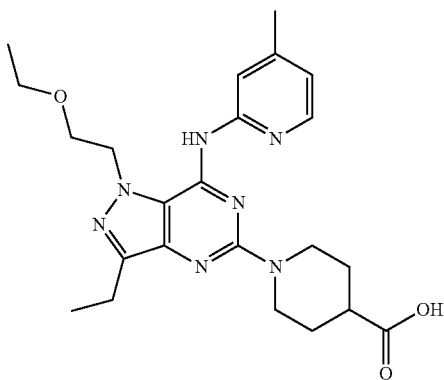 [SMILES: CCOCCn1nc(CC)c2nc(N3CCC(C(=O)O)CC3)nc(Nc3cc(C)ccn3)c21]

1-(1-(2-ethoxyethyl)-3-ethyl-7-(4-methylpyridin-2-ylamino)-1H-pyrazolo[4,3-d]pyrimidin-5-yl)piperidine-4-carboxylic acid Step 1: Preparation of 1-(2-ethoxyethyl)-3-ethyl-4-nitro-1H-pyrazole-5-carboxamide

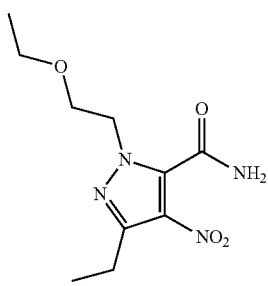 [SMILES: CCOCCn1nc(CC)c([N+](=O)[O-])c1C(N)=O]

1-(2-ethoxyethyl)-3-ethyl-4-nitro-1H-pyrazole-5-carboxamide was prepared according to step 1, Example 1

Step 2: Preparation of 4-amino-1-(2-ethoxyethyl)-3-ethyl-1H-pyrazole-5-carboxamide

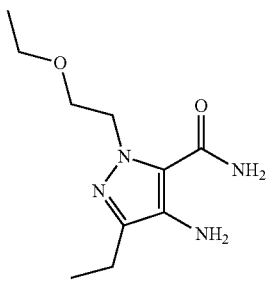

A mixture of 1-(2-ethoxyethyl)-3-ethyl-4-nitro-1H-pyrazole-5-carboxamide from step 1 (5.70 g, 22 mmol) and palladium hydroxide (1.0 g) in ethanol (110 mL) was treated with ammonium formate (7.01 g, 111 mmol) in four unequal portions at about 10 minute intervals. The resulting mixture was heated under reflux for two hours and then cooled. The mixture was filtered through celite and concentrated. The resulting residue was purified by column chromatography on silica gel using a mixture of ethyl acetate and hexane as the eluent to provide 2.45 g of the title compound. $^1$H NMR (400 MHz, CDCl$_3$): δ 1.17 (t, 3 H), 1.21-1.32 (m, 3 H), 2.60 (q, 2 H), 3.53 (q, 2 H), 3.79-3.95 (m, 2 H), 4.38-4.52 (m, 2 H). MS (ESI) m/z 227.

Step 3: 1-(2-ethoxyethyl)-3-ethyl-1H-pyrazolo[4,3-d]pyrimidine-5,7(4H,6H)-dione

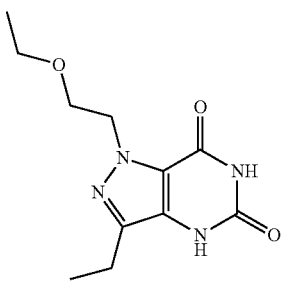 [SMILES: CCOCCn1nc(CC)c2[nH]c(=O)[nH]c(=O)c21]

A mixture of 4-amino-1-(2-ethoxyethyl)-3-ethyl-1H-pyrazole-5-carboxamide from step 2 (2.44 g, 10.8 mmol) in N,N-dimethylformamide (40 mL) was treated with carbonyldiimidazole (1.92 g, 11.9 mmol) and heated at 80° C. overnight. The mixture was concentrated in vacuuo and the residue was purified by column chromatography on silica gel using a mixture of ethyl acetate and hexane as the eluent to provide 1.04 g of the title compound. MS (ESI) m/z 253.

Step 4: Preparation of 5,7-dichloro-1-(2-ethoxyethyl)-3-ethyl-1H-pyrazolo[4,3-d]pyrimidine

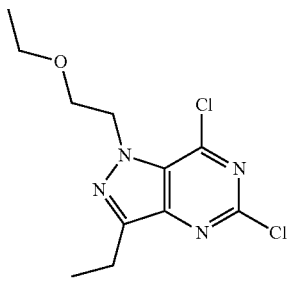 [SMILES: CCOCCn1nc(CC)c2nc(Cl)nc(Cl)c21]

A mixture of the 1-(2-ethoxyethyl)-3-ethyl-1H-pyrazolo[4,3-d]pyrimidine-5,7(4H,6H)-dione prepared in step 3 (7.2 g) and phosphorus oxychloride (200 mL) with one drop of N,N-dimethylformamide was heated at reflux overnight. The mixture was cooled and the phosphorus oxychloride was evaporated under reduced pressure. Ice was added to the resulting residue and then the mixture was extracted with chloroform. The organic layers were dried over magnesium sulfate, filtered, and evaporated to provide 2.09 g of 5,7-dichloro-1-(2-ethoxyethyl)-3-ethyl-1H-pyrazolo[4,3-d]pyrimidine as an oil which solidified upon standing. LCMS m/z 289.

Step 5: Preparation of 1-(1-(2-ethoxyethyl)-3-ethyl-7-(4-methylpyridin-2-ylamino)-1H-pyrazolo[4,3-d]pyrimidin-5-yl)piperidine-4-carboxylic acid

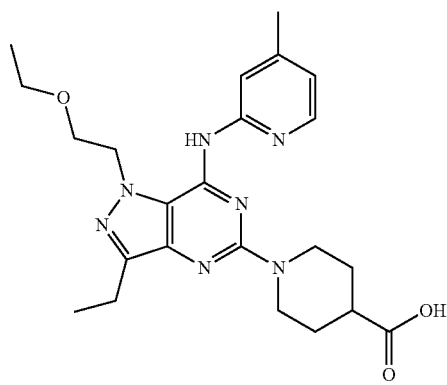 [SMILES: CCOCCn1nc(CC)c2nc(N3CCC(C(=O)O)CC3)nc(Nc3cc(C)ccn3)c21]

The 5,7-dichloro-1-(2-ethoxyethyl)-3-ethyl-1H-pyrazolo[4,3-d]pyrimidine prepared in step 4 (1 mmol), 2-amino-4-picoline (2 mmol), N,N-diisopropylethylamine (3 mmol), and N-methylpyrrolidone (1 mL) were added to each of two reaction vessels. Each vessel was irradiated in a CEM Discover microwave for 15 minutes at 150° C. Isonipecotic acid (3 mmol) was added to each reaction vessel and the resulting mixture irradiated for 15 minutes at 180° C. The contents of the two reaction vessels were combined. Water and ethyl acetate was added to the mixture and the mixture was shaken. Hydrochloric acid (1M) was added to the mixture and the mixture was shaken again. The layers were separated. The organic layer was washed with water, hydrochloric acid (1M) was added, and the layers were separated. The organic layer was dried over magnesium sulfate, filtered, and evaporated. The pH of the aqueous layer was raised to about six by adding saturated sodium carbonate and the aqueous layer was then extracted with ethyl acetate. The organic layer was dried over magnesium sulfate, filtered, added to the above organic residue and evaporated. The solution was purified by RP-HPLC on a Varian Dynamax C-18 column (250×41.4 mm) with a gradient of 10-95% acetonitrile/water (hydrochloric acid) over 15 minutes in two batches. Fractions were combined and evaporated to afford 0.26 g of the title compound. $^1$H NMR (400 MHz, DMSO-$d_6$): $\delta$ 1.10 (t, 3 H), 1.30 (t, 3 H), 1.49-1.60 (m, 2 H), 1.84-1.95 (m, 2 H), 2.32-2.36 (m, 3 H), 2.52-2.57 (m, 1 H), 2.78 (q, 2 H), 2.99-3.08 (m, 2 H), 3.52 (q, 2 H), 3.78 (t, 2 H), 4.45-4.53 (m, 2 H), 4.56-4.64 (m, 2 H), 6.91 (d, 1 H), 8.05 (s, 1 H), 8.18 (d, 1 H), 9.63 (s, 1 H), 12.18 (s, 1 H). LCMS m/z 454.

Protocols

N. Potency and Selectivity Assays

Method 1: Human Platelet PDE5 Enzyme Inhibition Scintillation Proximity Assay

An in vitro assay can be used to evaluate the inhibition of PDE5 enzyme activity by a test compound. As described more specifically below, this assay measures the PDE5 $IC_{50}$ value for the test compound (i.e., the concentration of the test compound required to inhibit by 50% the PDE5 enzyme-catalyzed hydrolysis of cGMP to GMP relative to the activity of uninhibited controls).

The PDE5 enzyme for use in the assay can be obtained from human platelets by appropriate modification of the method of Thompson, W J et al.; Biochemistry 18(23), 5228-5237, 1979, as described by Ballard S A et al.; J. Urology 159(6), 2164-2171, 1998. The PDE5 enzyme isolated from human platelets can be used to catalyze the hydrolysis of [$^3$H]cGMP (Amersham Biosciences) to 5' nucleotide [$^3$H] GMP. The [$^3$H]GMP binds to yttrium silicate SPA beads (Amersham Biosciences) and is detected by scintillation counting. More specifically, the effect of the test compound at different concentrations can be evaluated in the assay by contacting the compound with a fixed amount of PDE5 enzyme in the presence of substrate (cGMP or cAMP in a 3:1 ratio unlabelled to [$^3$H]-labeled). Scintillation counting can be used as described above to determine relative PDE5 enzyme activity. The inhibition of PDE5 enzyme activity is then calculated relative to total PDE5 enzyme activity of uninhibited controls.

PDE5 $IC_{50}$ Assay: 96-well microtiter plate format

Reagents

Buffer A: 20 mM Tris-HCl, 5 mM $MgCl_2$, pH 7.4

Buffer B: 2 mg/ml BSA in Buffer A (enzyme buffer)

cGMP substrate: Final concentration of 500 nM in assay

The amount of $^3$H-labeled substrate added depends upon the specific activity of [$^3$H]cGMP, and the cGMP substrate is diluted with a 10 mM stock of cold cGMP in Buffer A for a final substrate concentration of 500 nM in the assay.

PDE enzyme: Prepared in Buffer B. The dilution factor is determined by enzyme activity.

SPA beads: 20 mg/ml suspension prepared in dH2O.

| Positive Control | Negative Control | Standard/Test compound |
|---|---|---|
| 2 μl 100% DMSO | 2 μl 100% DMSO | 2 μl Standard/Test compound |
| 25 μl Buffer A | 25 μl Buffer A | 25 μl Buffer A |
| 25 μl Enzyme | 25 μl Buffer B | 25 μl Enzyme |
| 50 μl Substrate | 50 μl Substrate | 50 μl Substrate |
| 50 μl SPA to stop | 50 μl SPA to stop | 50 μl SPA to stop |

Stocks of standard and test compounds are prepared at 5 mM in 100% DMSO. The compound is serially diluted in a dilution plate using a 10-point ½ log dilution format. 2 µl of the compound dilution is added in duplicate to the wells of the assay plate. 2 µl of 100% DMSO are added to designated control wells. 25 µl of Buffer A are added to all wells. 25 µl of Buffer B are added to the negative control wells. 25 µl of enzyme are added to the remaining wells. 50 µl of substrate are added to each well. Plates are sealed and incubated for 60 minutes on a plate shaker at 30 C. 50 pl of SPA beads are added to stop the reaction. The plates are again sealed and shaken for 15 minutes to allow the beads to bind the GMP product. The beads are allowed to settle for 30 minutes and then read on a NXT TopCount scintillation counter. Data are analyzed with a curve fitting application for plate-based screening. Percent inhibition in this assay is calculated as follows:

Inhibition (%)=[(mean maximum−compound value/ (mean maximum−mean minimum)]×100.

The $IC_{50}$ value is determined from sigmoid dose-response curves of enzyme activity versus compound concentration.

The Carboxypiperidine Compound was tested in accordance with Method 1. The corresponding PDE5 $IC_{50}$ values measured are reported in Table A.

TABLE A

| RUN NO. | METHOD 1: PDE5 $IC_{50}$ (nM) |
|---|---|
| 1 | 0.050 |
| 2 | 0.044 |
| AVERAGE: | 0.047 |

Compounds previously disclosed in examples from WO2004096810 were tested in accordance with Method 1. The corresponding PDE5 $IC_{50}$ values measured are reported in Table B.

TABLE B

| WO2004096810 EXAMPLE NO. | STRUCTURE | METHOD 1: PDE5 $IC_{50}$ (nM) |
|---|---|---|
| 1 | 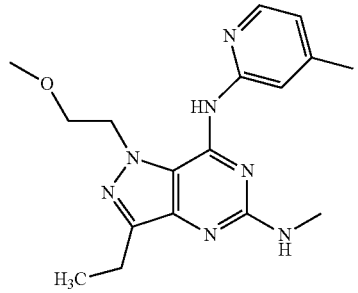 | 16.2 |
| 2 | 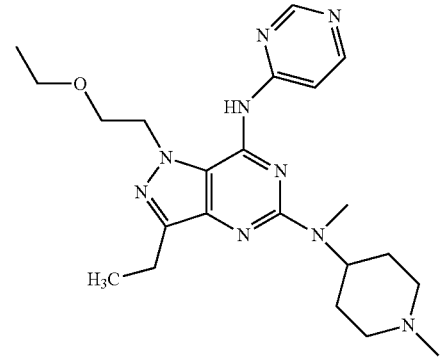 [SMILES: CCOCCn1nc(CC)c2nc(N(C)C3CCN(C)CC3)nc(Nc3ccncn3)c21] | 0.48 |
| 3 | 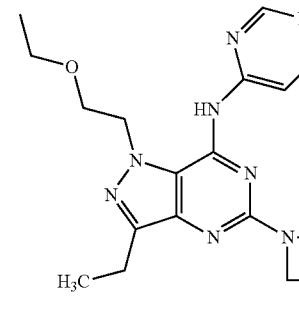 | 43.8 |

TABLE B-continued

| WO2004096810 EXAMPLE NO. | STRUCTURE | METHOD 1: PDE5 IC$_{50}$ (nM) |
|---|---|---|
| 4 | 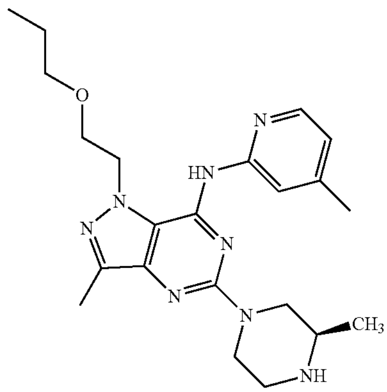 [SMILES: CCCOCCn1nc(C)c2nc(N3CCN[C@H](C)C3)nc(Nc3cc(C)ccn3)c21] | 8.84 |
| 7 | 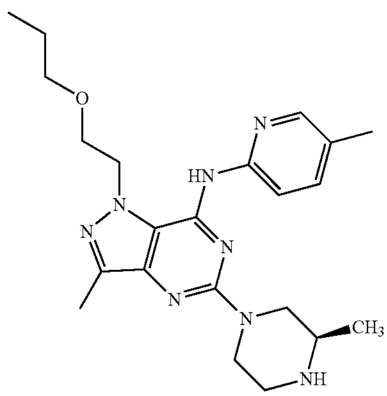 [SMILES: CCCOCCn1nc(C)c2nc(N3CCN[C@H](C)C3)nc(Nc3ccc(C)cn3)c21] | 6.03 |
| 8 | 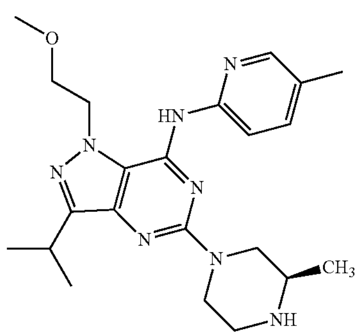 [SMILES: COCCn1nc(C(C)C)c2nc(N3CCN[C@H](C)C3)nc(Nc3ccc(C)cn3)c21] | 6.95 |
| 9 | 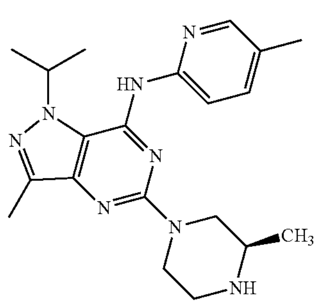 | 508 |

TABLE B-continued

| WO2004096810 EXAMPLE NO. | STRUCTURE | METHOD 1: PDE5 IC$_{50}$ (nM) |
|---|---|---|
| 11 | 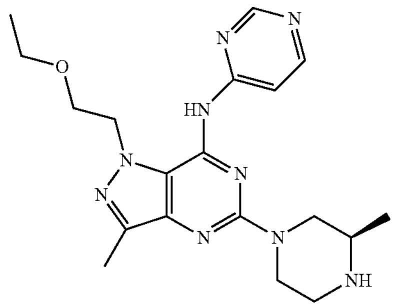 [SMILES: CCOCCn1nc(C)c2nc(N3CCN[C@H](C)C3)nc(Nc3ccncn3)c21] | 0.29 |
| 12 | 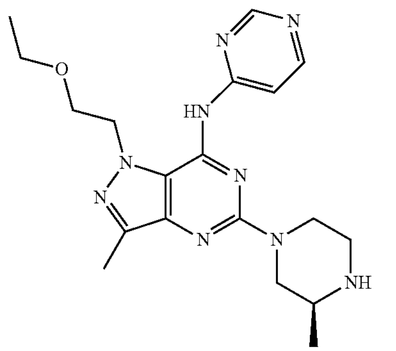 [SMILES: CCOCCn1nc(C)c2nc(N3CCN[C@@H](C)C3)nc(Nc3ccncn3)c21] | 1.74 |
| 13 | 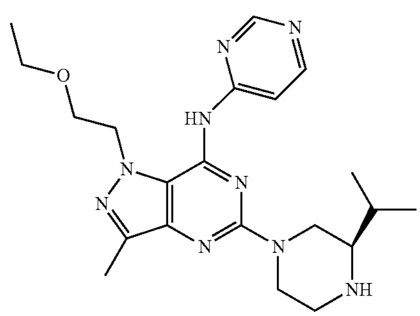 [SMILES: CCOCCn1nc(C)c2nc(N3CCN[C@H](C(C)C)C3)nc(Nc3ccncn3)c21] | 19.1 |
| 14 | 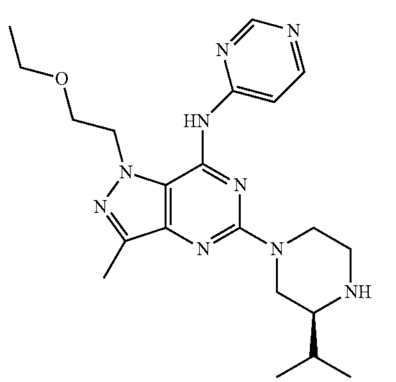 [SMILES: CCOCCn1nc(C)c2nc(N3CCN[C@@H](C(C)C)C3)nc(Nc3ccncn3)c21] | 42.1 |

TABLE B-continued

| WO2004096810 EXAMPLE NO. | STRUCTURE | METHOD 1: PDE5 IC$_{50}$ (nM) |
| --- | --- | --- |
| 15 | 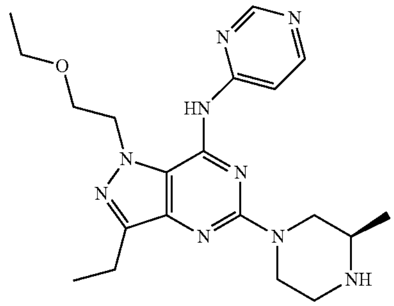 [SMILES: CCOCCn1nc(CC)c2nc(N3CCN[C@H](C)C3)nc(Nc3ccncn3)c21] | 0.09 |
| 16 | 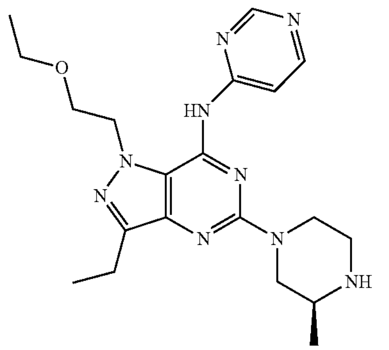 [SMILES: CCOCCn1nc(CC)c2nc(N3CCN[C@@H](C)C3)nc(Nc3ccncn3)c21] | 0.98 |
| 17 | 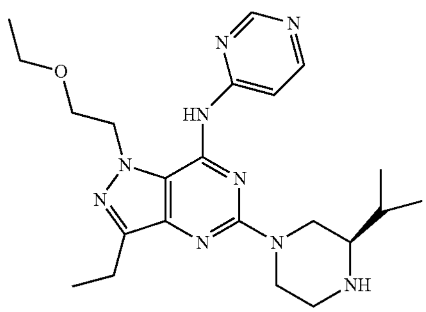 [SMILES: CCOCCn1nc(CC)c2nc(N3CCN[C@H](C(C)C)C3)nc(Nc3ccncn3)c21] | 22.4 |
| 18 | 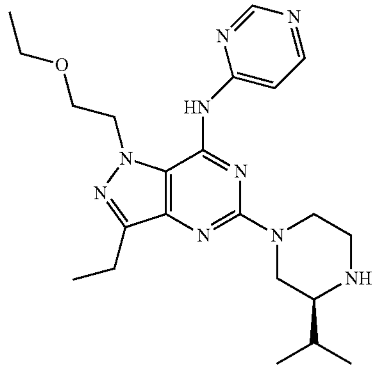 [SMILES: CCOCCn1nc(CC)c2nc(N3CCN[C@@H](C(C)C)C3)nc(Nc3ccncn3)c21] | 25.8 |

TABLE B-continued

| WO2004096810 EXAMPLE NO. | STRUCTURE | METHOD 1: PDE5 IC$_{50}$ (nM) |
|---|---|---|
| 19 | 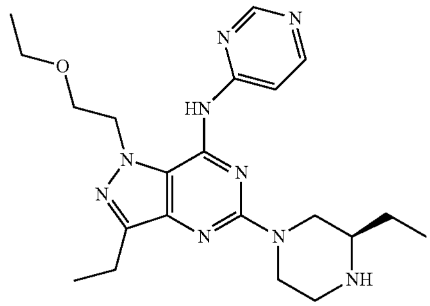 [SMILES: CCOCCn1nc(CC)c2nc(N3CCN[C@H](CC)C3)nc(Nc3ccncn3)c21] | 0.49 |
| 21 | 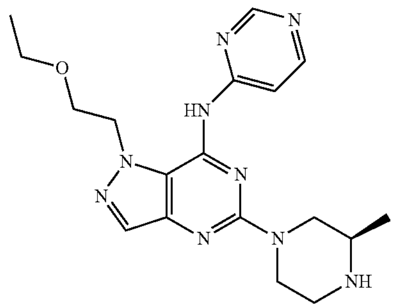 [SMILES: CCOCCn1ncc2nc(N3CCN[C@H](C)C3)nc(Nc3ccncn3)c21] | 2.04 |
| 23 | 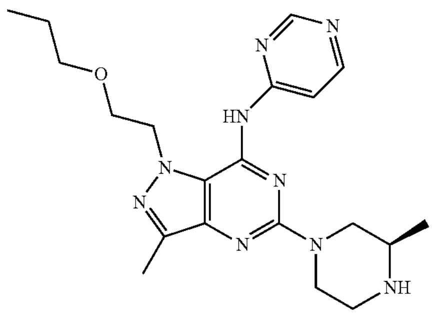 [SMILES: CCCOCCn1nc(C)c2nc(N3CCN[C@H](C)C3)nc(Nc3ccncn3)c21] | 0.39 |
| 24 | 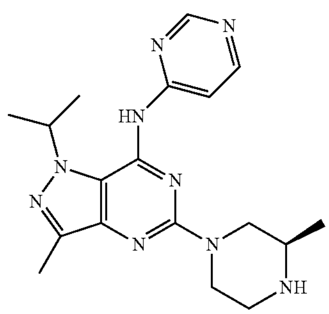 [SMILES: Cc1nn(C(C)C)c2c(Nc3ccncn3)nc(N3CCN[C@H](C)C3)nc12] | 37.7 |
| 26 | 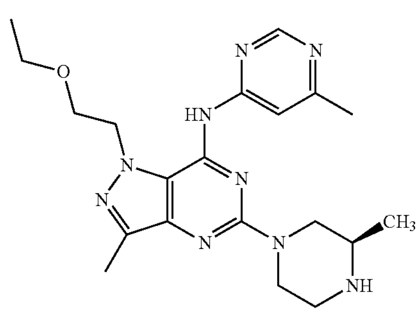 [SMILES: CCOCCn1nc(C)c2nc(N3CCN[C@H](C)C3)nc(Nc3cc(C)ncn3)c21] | 1.83 |

TABLE B-continued

| WO2004096810 EXAMPLE NO. | STRUCTURE | METHOD 1: PDE5 IC$_{50}$ (nM) |
|---|---|---|
| 28 | 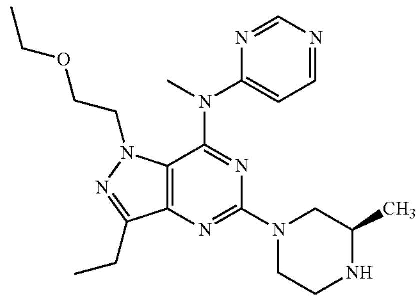 [SMILES: CCOCCn1nc(CC)c2nc(N3CCN[C@H](C)C3)nc(N(C)c3ccncn3)c21] | 47.9 |
| 34 | 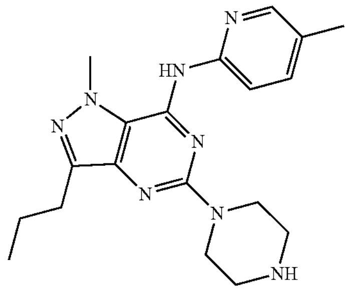 [SMILES: CCCc1nn(C)c2c(Nc3ccc(C)cn3)nc(N3CCNCC3)nc12] | 50.2 |
| 35 | 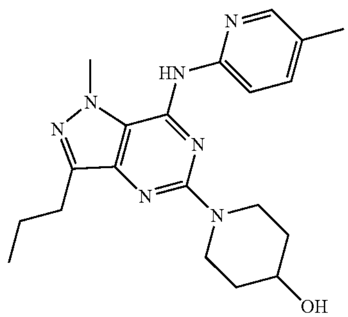 [SMILES: CCCc1nn(C)c2c(Nc3ccc(C)cn3)nc(N3CCC(O)CC3)nc12] | 737 |
| 36 | 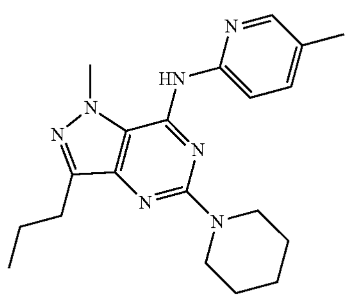 [SMILES: CCCc1nn(C)c2c(Nc3ccc(C)cn3)nc(N3CCCCC3)nc12] | 1450 |
| 37 | 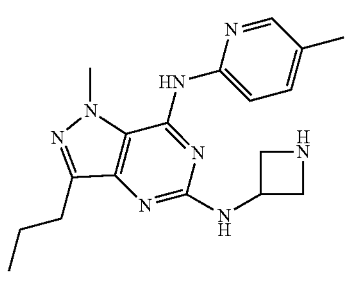 [SMILES: CCCc1nn(C)c2c(Nc3ccc(C)cn3)nc(NC3CNC3)nc12] | >10,000 |

TABLE B-continued
| WO2004096810 EXAMPLE NO. | STRUCTURE | METHOD 1: PDE5 IC$_{50}$ (nM) |
|---|---|---|
| 38 | 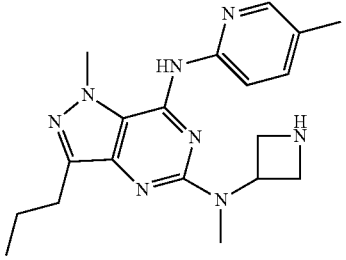 [SMILES: CCCc1nn(C)c2c(Nc3ccc(C)cn3)nc(N(C)C3CNC3)nc12] | >10,000 |
| 39 | 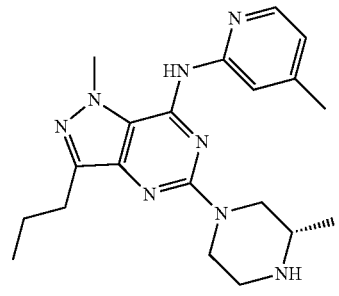 [SMILES: CCCc1nn(C)c2c(Nc3cc(C)ccn3)nc(N3CCN[C@@H](C)C3)nc12] | 456 |
| 40 | 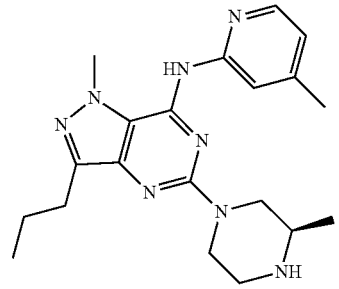 [SMILES: CCCc1nn(C)c2c(Nc3cc(C)ccn3)nc(N3CCN[C@H](C)C3)nc12] | 334 |
| 71 | 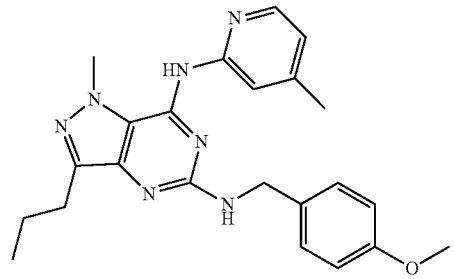 [SMILES: CCCc1nn(C)c2c(Nc3cc(C)ccn3)nc(NCc3ccc(OC)cc3)nc12] | 152 |
| 72 | 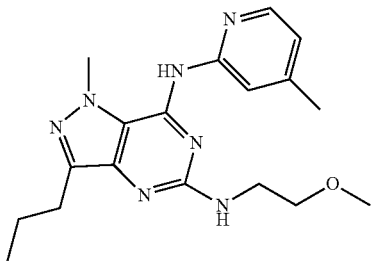 [SMILES: CCCc1nn(C)c2c(Nc3cc(C)ccn3)nc(NCCOC)nc12] | 177 |

TABLE B-continued

| WO2004096810 EXAMPLE NO. | STRUCTURE | METHOD 1: PDE5 IC$_{50}$ (nM) |
|---|---|---|
| 77 | 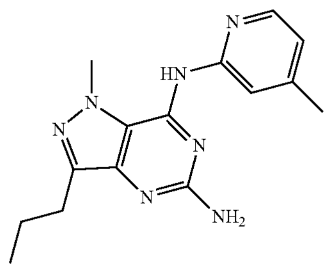 [SMILES: CCCc1nn(C)c2c(Nc3cc(C)ccn3)nc(N)nc12] | >10,000 |
| 80 | 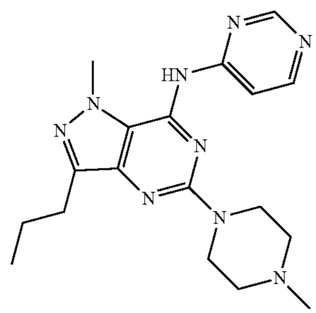 [SMILES: CCCc1nn(C)c2c(Nc3ccncn3)nc(N3CCN(C)CC3)nc12] | 1940 |
| 81 | 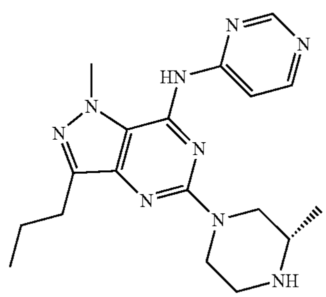 [SMILES: CCCc1nn(C)c2c(Nc3ccncn3)nc(N3CCN[C@@H](C)C3)nc12] | 118 |
| 83 | 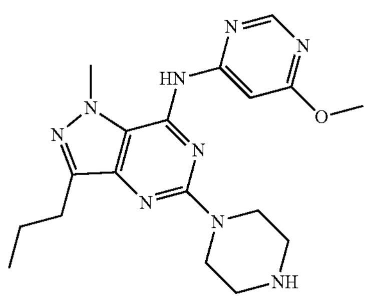 [SMILES: CCCc1nn(C)c2c(Nc3cc(OC)ncn3)nc(N3CCNCC3)nc12] | 134 |
| 84 | 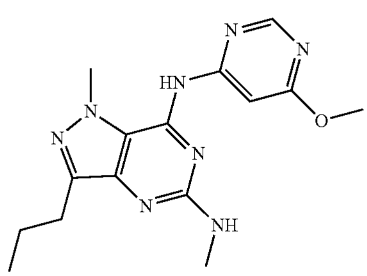 [SMILES: CCCc1nn(C)c2c(Nc3cc(OC)ncn3)nc(NC)nc12] | 247 |

TABLE B-continued

| WO2004096810 EXAMPLE NO. | STRUCTURE | METHOD 1: PDE5 IC$_{50}$ (nM) |
|---|---|---|
| 88 | 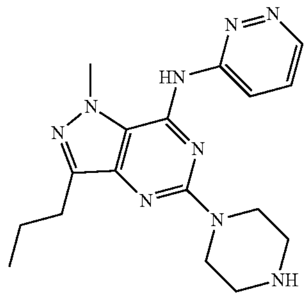 [SMILES: CCCc1nn(C)c2c(Nc3cccnn3)nc(N3CCNCC3)nc12] | >100 |
| 90 | 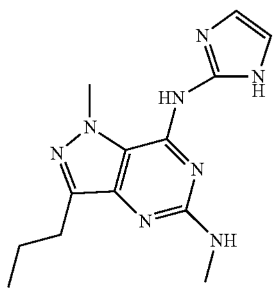 [SMILES: CCCc1nn(C)c2c(Nc3ncc[nH]3)nc(NC)nc12] | 1550 |
| 91 | 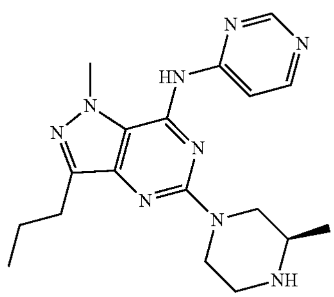 [SMILES: CCCc1nn(C)c2c(Nc3ccncn3)nc(N3CCN[C@H](C)C3)nc12] | 22.6 |
| 92 | 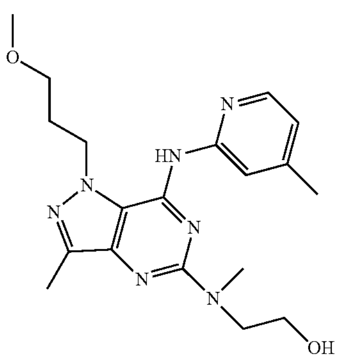 [SMILES: COCCCn1nc(C)c2nc(N(C)CCO)nc(Nc3cc(C)ccn3)c21] | 26.5 |
| 93 | 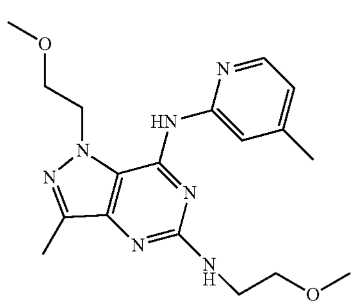 | 31.1 |

TABLE B-continued

| WO2004096810 EXAMPLE NO. | STRUCTURE | METHOD 1: PDE5 IC$_{50}$ (nM) |
|---|---|---|
| 94 | 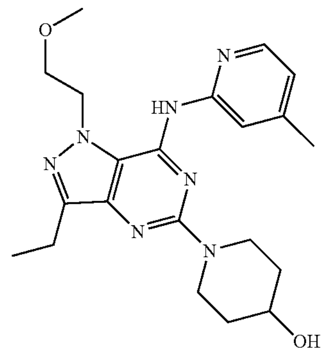 [SMILES: CCc1nn(CCOC)c2c(Nc3cc(C)ccn3)nc(N3CCC(O)CC3)nc12] | 43.2 |
| 95 | 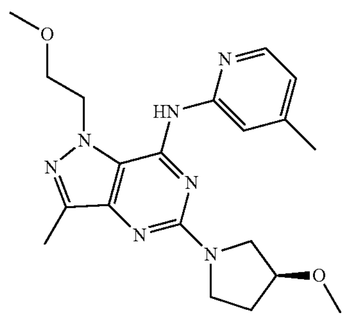 | 76.0 |
| 96 | 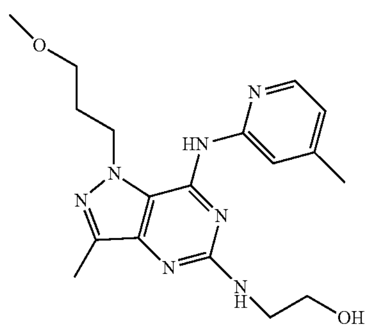 | 87.9 |
| 98 | 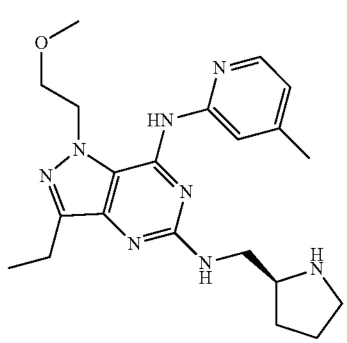 [SMILES: CCc1nn(CCOC)c2c(Nc3cc(C)ccn3)nc(NC[C@@H]3CCCN3)nc12] | 231 |

TABLE B-continued

| WO2004096810 EXAMPLE NO. | STRUCTURE | METHOD 1: PDE5 IC$_{50}$ (nM) |
|---|---|---|
| 99 | 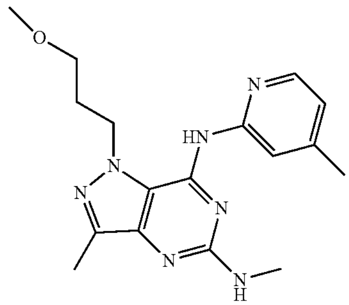 | 239 |
| 100 | 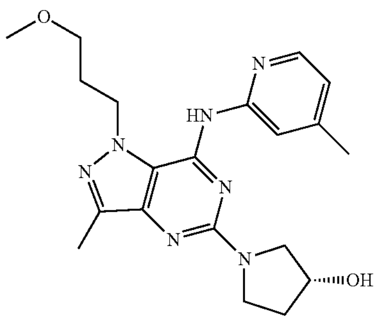 [SMILES: COCCCn1nc(C)c2nc(N3CC[C@@H](O)C3)nc(Nc3cc(C)ccn3)c21] | 67.2 |
| 103 | 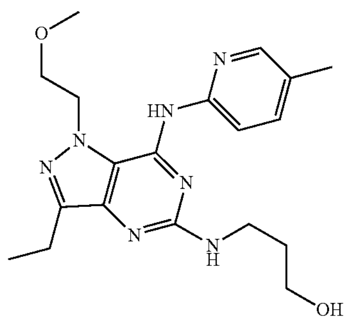 [SMILES: CCc1nn(CCOC)c2c(Nc3ccc(C)cn3)nc(NCCCO)nc12] | 76.6 |
| 108 | 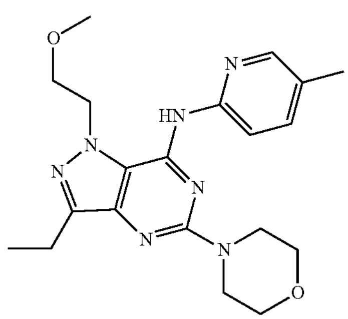 [SMILES: CCc1nn(CCOC)c2c(Nc3ccc(C)cn3)nc(N3CCOCC3)nc12] | 778 |
| 109 | 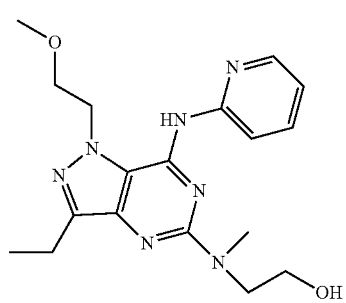 [SMILES: CCc1nn(CCOC)c2c(Nc3ccccn3)nc(N(C)CCO)nc12] | 27.3 |

TABLE B-continued
| WO2004096810 EXAMPLE NO. | STRUCTURE | METHOD 1: PDE5 IC$_{50}$ (nM) |
|---|---|---|
| 110 | 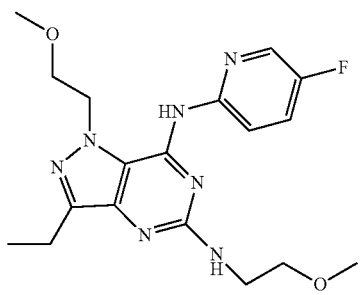 [SMILES: CCc1nn(CCOC)c2c(Nc3ccc(F)cn3)nc(NCCOC)nc12] | 513 |
| 113 | 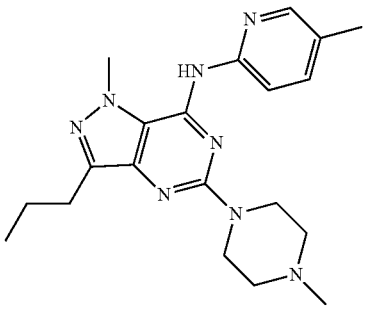 [SMILES: CCCc1nn(C)c2c(Nc3ccc(C)cn3)nc(N3CCN(C)CC3)nc12] | 1250 |
| 114 | 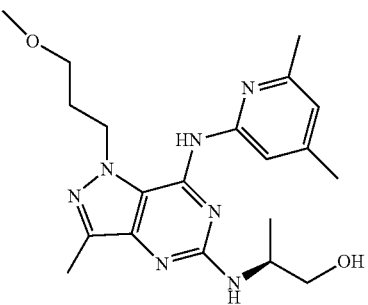 [SMILES: COCCCn1nc(C)c2nc(N[C@@H](C)CO)nc(Nc3cc(C)cc(C)n3)c21] | 60.6 |
| 115 | 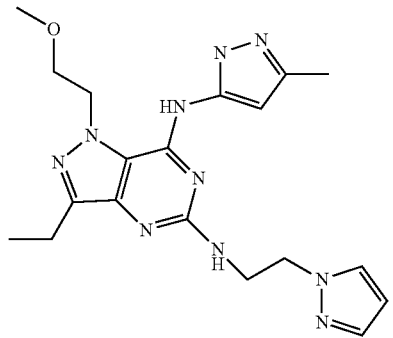 [SMILES: CCc1nn(CCOC)c2c(Nc3cc(C)n[nH]3)nc(NCCn3cccn3)nc12] | 220 |

TABLE B-continued

| WO2004096810 EXAMPLE NO. | STRUCTURE | METHOD 1: PDE5 IC$_{50}$ (nM) |
|---|---|---|
| 116 | 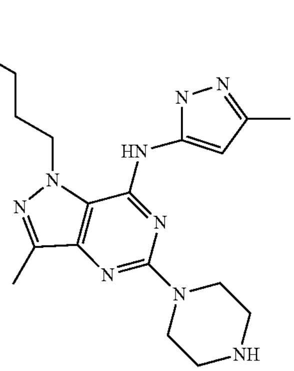 | 1760 |
| 123 | 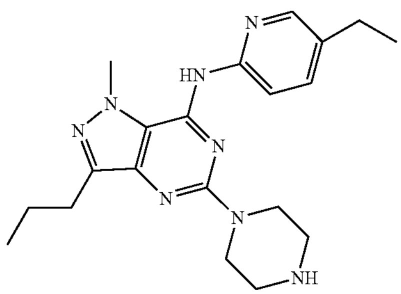 [SMILES: CCCc1nn(C)c2c(Nc3ccc(CC)cn3)nc(N3CCNCC3)nc12] | 248 |
| 124 | 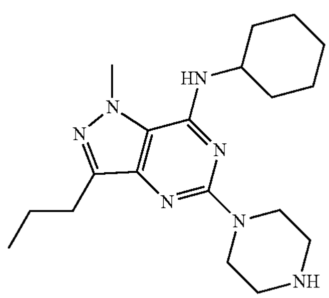 [SMILES: CCCc1nn(C)c2c(NC3CCCCC3)nc(N3CCNCC3)nc12] | 78.2 |
| 125 | 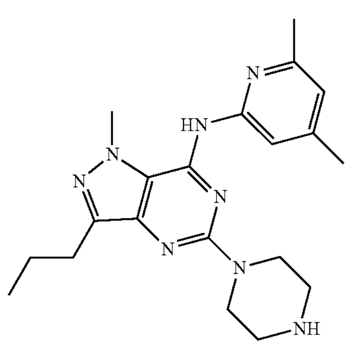 [SMILES: CCCc1nn(C)c2c(Nc3cc(C)cc(C)n3)nc(N3CCNCC3)nc12] | 182 |

TABLE B-continued
| WO2004096810 EXAMPLE NO. | STRUCTURE | METHOD 1: PDE5 IC$_{50}$ (nM) |
| --- | --- | --- |
| 126 | 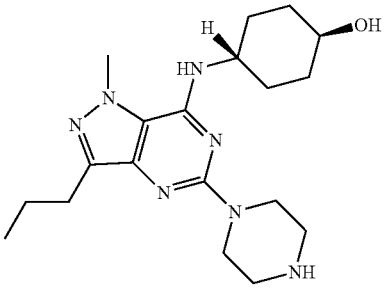 [SMILES: CCCc1nn(C)c2c(N[C@H]3CC[C@H](O)CC3)nc(N3CCNCC3)nc12] | 2230 |
| 127 | 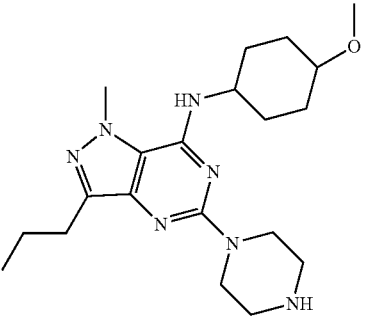 [SMILES: CCCc1nn(C)c2c(NC3CCC(OC)CC3)nc(N3CCNCC3)nc12] | 7580 |
| 128 | 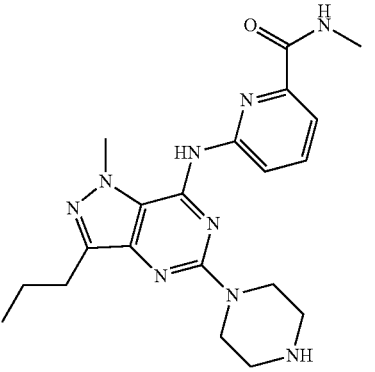 [SMILES: CCCc1nn(C)c2c(Nc3cccc(C(=O)NC)n3)nc(N3CCNCC3)nc12] | 1390 |
| 129 | 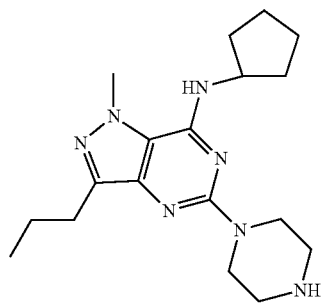 [SMILES: CCCc1nn(C)c2c(NC3CCCC3)nc(N3CCNCC3)nc12] | 139 |
| 130 | 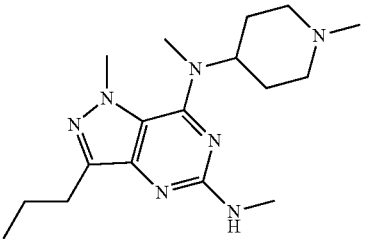 [SMILES: CCCc1nn(C)c2c(N(C)C3CCN(C)CC3)nc(NC)nc12] | >10,000 |

TABLE B-continued

| WO2004096810 EXAMPLE NO. | STRUCTURE | METHOD 1: PDE5 IC$_{50}$ (nM) |
|---|---|---|
| 133 | 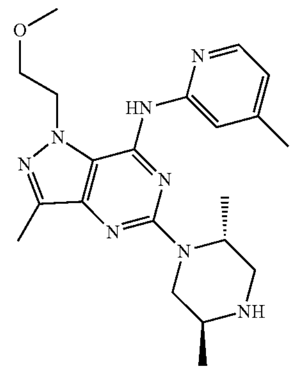 | 4.45 |
| 134 | 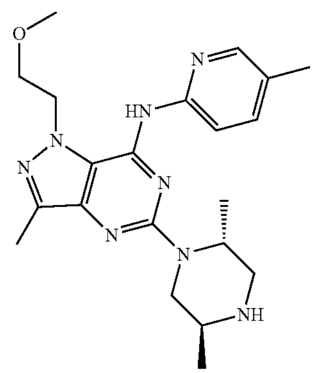 | 6.57 |
| 135 | 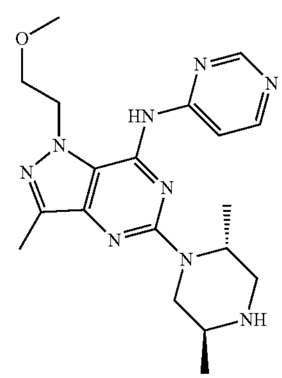 [SMILES: COCCn1nc(C)c2nc(N3C[C@H](C)NC[C@H]3C)nc(Nc3ccncn3)c21] | 0.92 |
| 136 | 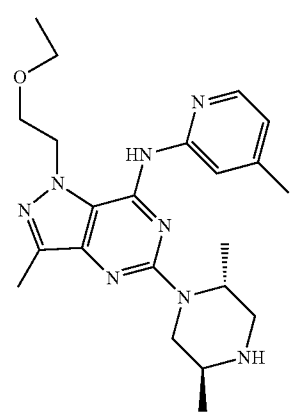 | 1.09 |

TABLE B-continued

| WO2004096810 EXAMPLE NO. | STRUCTURE | METHOD 1: PDE5 IC$_{50}$ (nM) |
| --- | --- | --- |
| 137 | 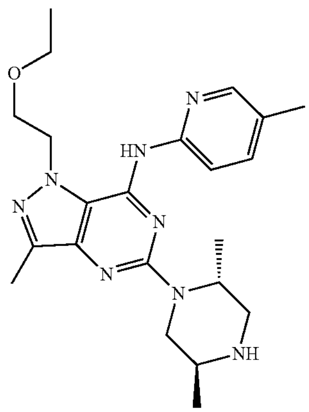 | 1.43 |
| 138 | 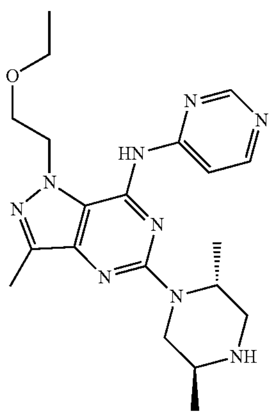 [SMILES: CCOCCn1nc(C)c2nc(N3C[C@H](C)NC[C@H]3C)nc(Nc3ccncn3)c21] | 0.33 |
| 139 | 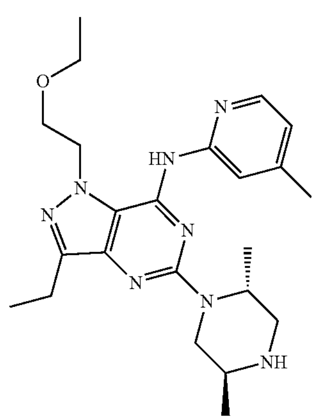 [SMILES: CCOCCn1nc(CC)c2nc(N3C[C@H](C)NC[C@H]3C)nc(Nc3cc(C)ccn3)c21] | 0.55 |

TABLE B-continued

| WO2004096810 EXAMPLE NO. | STRUCTURE | METHOD 1: PDE5 IC$_{50}$ (nM) |
|---|---|---|
| 140 | 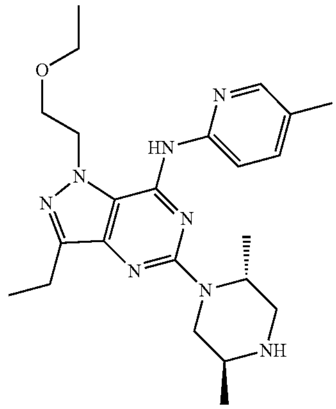 [SMILES: CCOCCn1nc(CC)c2nc(N3C[C@H](C)NC[C@H]3C)nc(Nc3ccc(C)cn3)c21] | 1.95 |
| 141 | 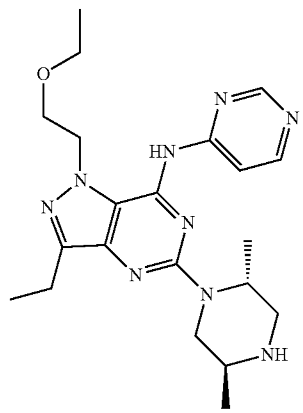 [SMILES: CCOCCn1nc(CC)c2nc(N3C[C@H](C)NC[C@H]3C)nc(Nc3ccncn3)c21] | 0.15 |
| 142 | 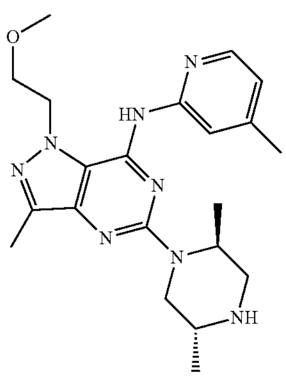 | 22.7 |
| 143 | 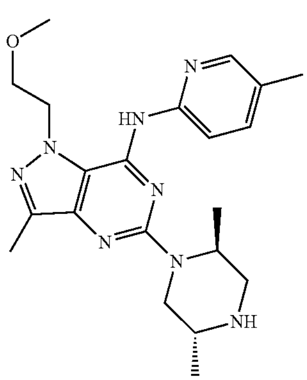 | 81.2 |

TABLE B-continued
| WO2004096810 EXAMPLE NO. | STRUCTURE | METHOD 1: PDE5 IC$_{50}$ (nM) |
|---|---|---|
| 144 | 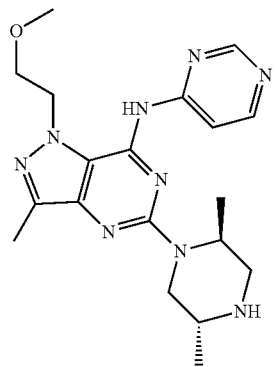 [SMILES: COCCn1nc(C)c2nc(N3C[C@@H](C)NC[C@@H]3C)nc(Nc3ccncn3)c21] | 5.34 |
| 145 | 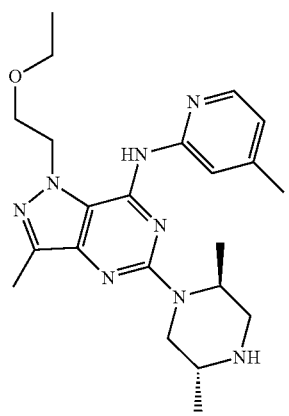 | 7.15 |
| 146 | 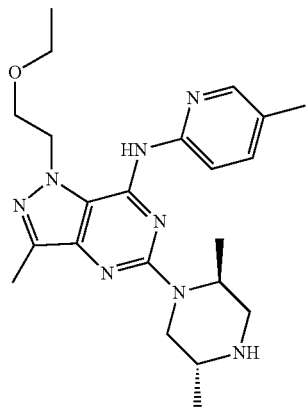 | 32.1 |

TABLE B-continued

| WO2004096810 EXAMPLE NO. | STRUCTURE | METHOD 1: PDE5 IC$_{50}$ (nM) |
|---|---|---|
| 147 | 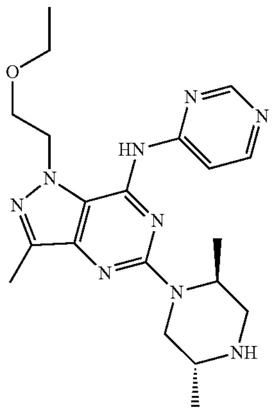 [SMILES: CCOCCn1nc(C)c2nc(N3C[C@@H](C)NC[C@@H]3C)nc(Nc3ccncn3)c21] | 2.46 |
| 148 | 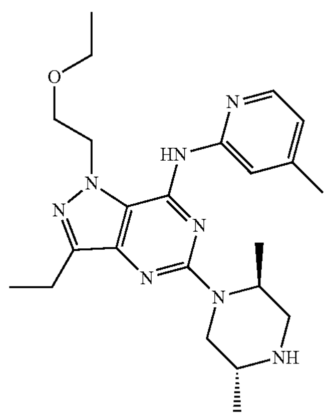 [SMILES: CCOCCn1nc(CC)c2nc(N3C[C@@H](C)NC[C@@H]3C)nc(Nc3cc(C)ccn3)c21] | 4.39 |
| 149 | 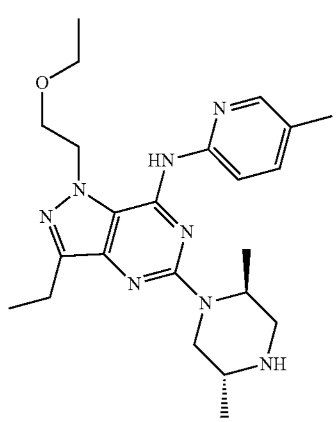 [SMILES: CCOCCn1nc(CC)c2nc(N3C[C@@H](C)NC[C@@H]3C)nc(Nc3ccc(C)cn3)c21] | 34.8 |

TABLE B-continued

| WO2004096810 EXAMPLE NO. | STRUCTURE | METHOD 1: PDE5 IC$_{50}$ (nM) |
| --- | --- | --- |
| 150 | 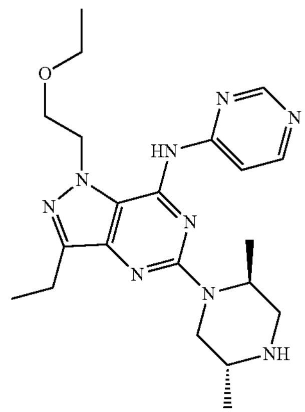 [SMILES: CCOCCn1nc(CC)c2nc(N3C[C@@H](C)NC[C@@H]3C)nc(Nc3ccncn3)c21] | 1.83 |
| 151 | 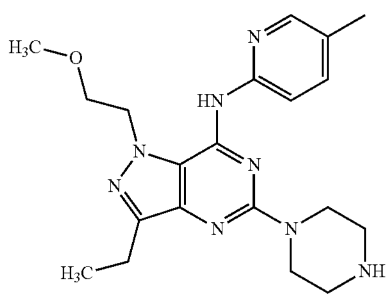 [SMILES: CCc1nn(CCOC)c2c(Nc3ccc(C)cn3)nc(N3CCNCC3)nc12] | 22.0 |
| 152 | 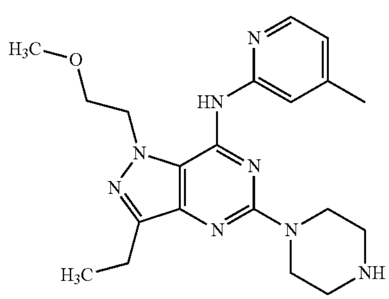 | 12.1 |
| 153 | 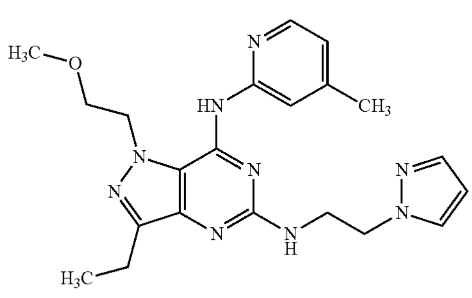 [SMILES: CCc1nn(CCOC)c2c(Nc3cc(C)ccn3)nc(NCCn3cccn3)nc12] | 19.5 |

TABLE B-continued
| WO2004096810 EXAMPLE NO. | STRUCTURE | METHOD 1: PDE5 IC$_{50}$ (nM) |
|---|---|---|
| 154 | 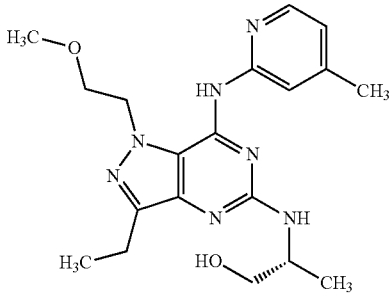 | 12.6 |
| 155 | 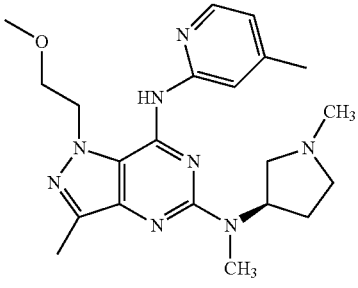 [SMILES: COCCn1nc(C)c2nc(N(C)[C@@H]3CCN(C)C3)nc(Nc3cc(C)ccn3)c21] | 13.4 |
| 156 | 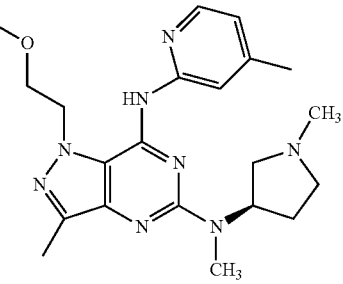 | 1.80 |
| 157 | 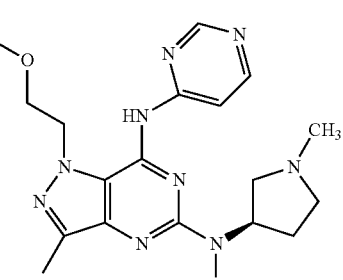 | 16.7 |
| 158 | 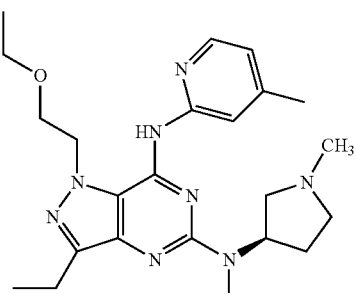 | 0.71 |

TABLE B-continued

| WO2004096810 EXAMPLE NO. | STRUCTURE | METHOD 1: PDE5 IC$_{50}$ (nM) |
|---|---|---|
| 159 | 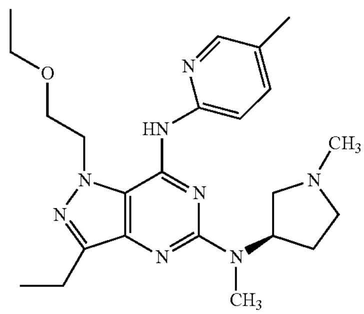 [SMILES: CCOCCn1nc(CC)c2nc(N(C)[C@@H]3CCN(C)C3)nc(Nc3ccc(C)cn3)c21] | 16.3 |
| 160 | 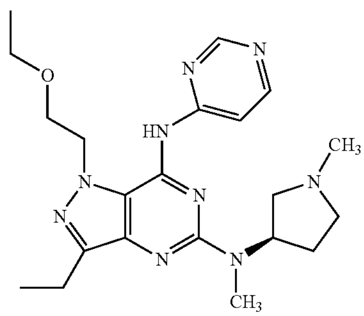 [SMILES: CCOCCn1nc(CC)c2nc(N(C)[C@@H]3CCN(C)C3)nc(Nc3ccncn3)c21] | 7.22 |
| 161 | 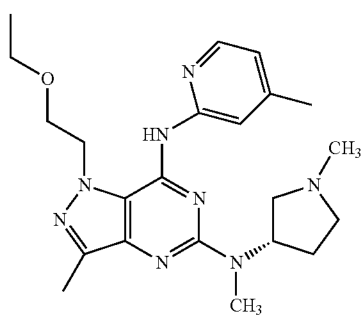 [SMILES: CCOCCn1nc(C)c2nc(N(C)[C@H]3CCN(C)C3)nc(Nc3cc(C)ccn3)c21] | 0.50 |
| 162 | 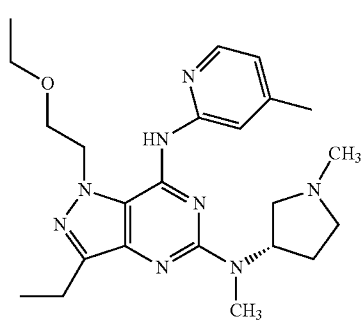 [SMILES: CCOCCn1nc(CC)c2nc(N(C)[C@H]3CCN(C)C3)nc(Nc3cc(C)ccn3)c21] | 0.24 |

TABLE B-continued
| WO2004096810 EXAMPLE NO. | STRUCTURE | METHOD 1: PDE5 IC$_{50}$ (nM) |
|---|---|---|
| 164 | 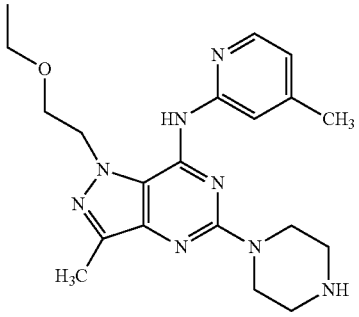 [SMILES: CCOCCn1nc(C)c2nc(N3CCNCC3)nc(Nc3cc(C)ccn3)c21] | 3.46 |
| 165 | 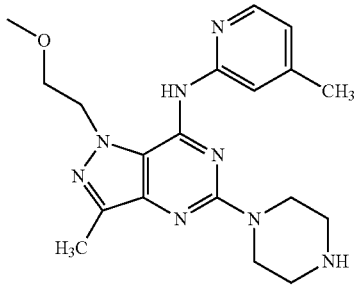 [SMILES: COCCn1nc(C)c2nc(N3CCNCC3)nc(Nc3cc(C)ccn3)c21] | 10.5 |
| 166 | 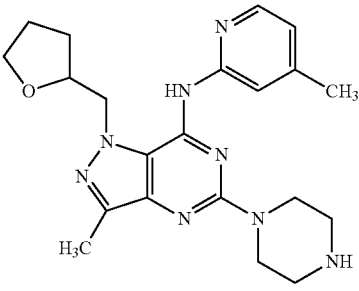 [SMILES: Cc1ccnc(Nc2nc(N3CCNCC3)nc3c(C)nn(CC4CCCO4)c23)c1] | 11.5 |
| 167 | 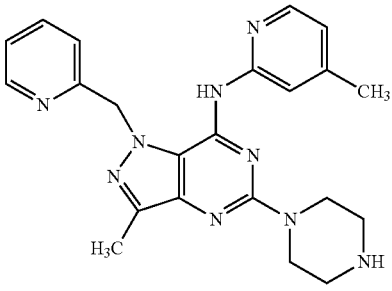 [SMILES: Cc1ccnc(Nc2nc(N3CCNCC3)nc3c(C)nn(Cc4ccccn4)c23)c1] | 2.95 |
| 168 | 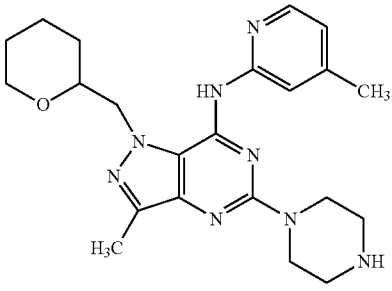 [SMILES: Cc1ccnc(Nc2nc(N3CCNCC3)nc3c(C)nn(CC4CCCCO4)c23)c1] | 0.81 |

TABLE B-continued

| WO2004096810 EXAMPLE NO. | STRUCTURE | METHOD 1: PDE5 IC$_{50}$ (nM) |
|---|---|---|
| 170 | 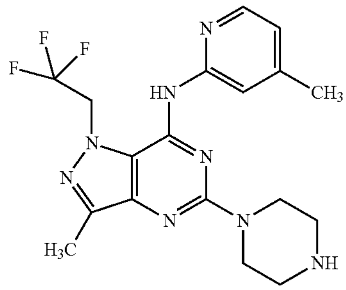 [SMILES: Cc1ccnc(Nc2nc(N3CCNCC3)nc3c(C)nn(CC(F)(F)F)c23)c1] | 2100 |
| 173 | 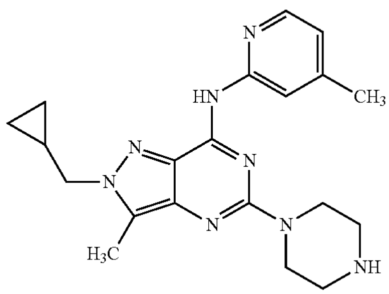 [SMILES: Cc1ccnc(Nc2nc(N3CCNCC3)nc3c(C)n(CC4CC4)nc23)c1] | 396 |
| 174 | 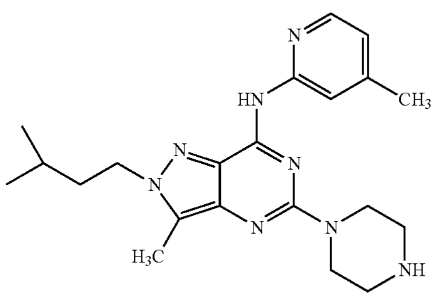 [SMILES: Cc1ccnc(Nc2nc(N3CCNCC3)nc3c(C)n(CCC(C)C)nc23)c1] | 432 |
| 176 | 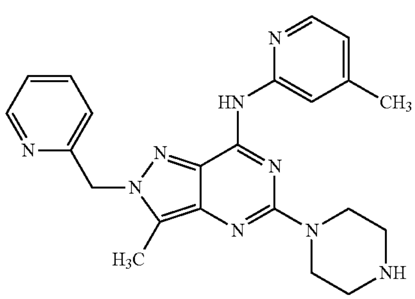 [SMILES: Cc1ccnc(Nc2nc(N3CCNCC3)nc3c(C)n(Cc4ccccn4)nc23)c1] | 274 |
| 177 | 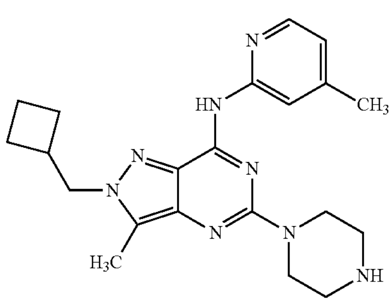 [SMILES: Cc1ccnc(Nc2nc(N3CCNCC3)nc3c(C)n(CC4CCC4)nc23)c1] | 535 |

TABLE B-continued

| WO2004096810 EXAMPLE NO. | STRUCTURE | METHOD 1: PDE5 IC$_{50}$ (nM) |
|---|---|---|
| 179 | 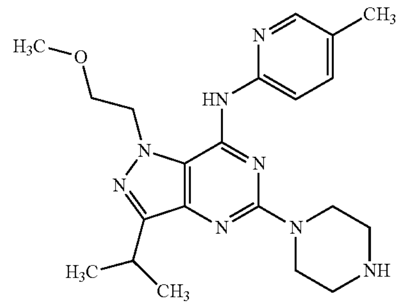 | 18.3 |
| 180 | 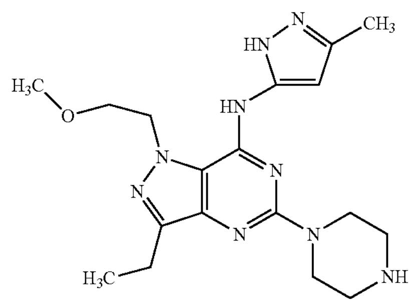 [SMILES: CCc1nn(CCOC)c2c(Nc3cc(C)n[nH]3)nc(N3CCNCC3)nc12] | 341 |
| 181 | 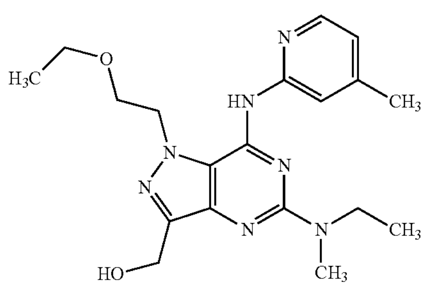 [SMILES: CCOCCn1nc(CO)c2nc(N(C)CC)nc(Nc3cc(C)ccn3)c21] | 0.39 |
| 182 | 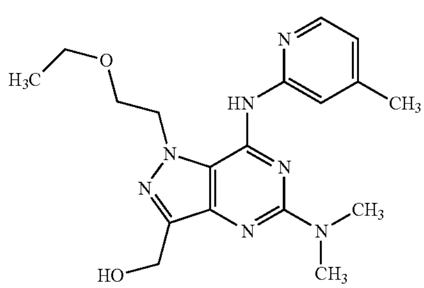 [SMILES: CCOCCn1nc(CO)c2nc(N(C)C)nc(Nc3cc(C)ccn3)c21] | 4.03 |
| 185 | 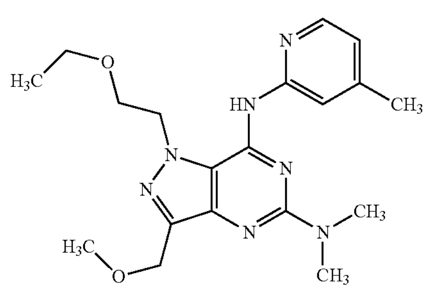 [SMILES: CCOCCn1nc(COC)c2nc(N(C)C)nc(Nc3cc(C)ccn3)c21] | 1.30 |

TABLE B-continued

| WO2004096810 EXAMPLE NO. | STRUCTURE | METHOD 1: PDE5 IC$_{50}$ (nM) |
|---|---|---|
| 188 | 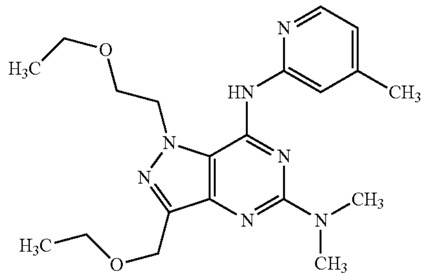 [SMILES: CCOCCn1nc(COCC)c2nc(N(C)C)nc(Nc3cc(C)ccn3)c21] | 0.47 |
| 191 | 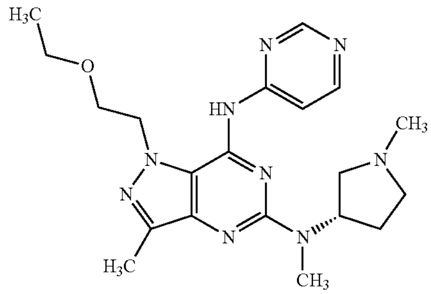 [SMILES: CCOCCn1nc(C)c2nc(N(C)[C@H]3CCN(C)C3)nc(Nc3ccncn3)c21] | 0.24 |
| 192 | 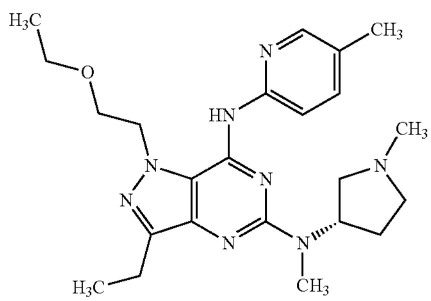 [SMILES: CCOCCn1nc(CC)c2nc(N(C)[C@H]3CCN(C)C3)nc(Nc3ccc(C)cn3)c21] | 3.06 |
| 193 | 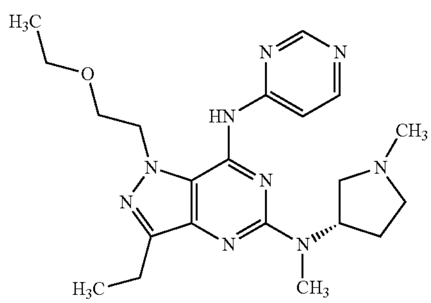 [SMILES: CCOCCn1nc(CC)c2nc(N(C)[C@H]3CCN(C)C3)nc(Nc3ccncn3)c21] | 1.01 |
| 194 | 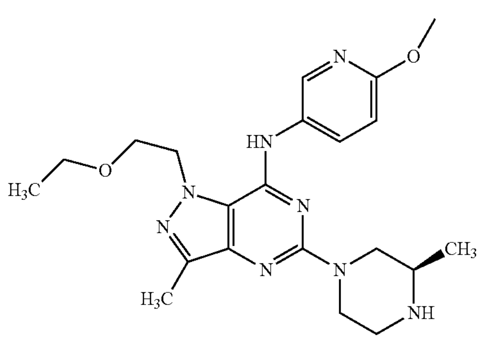 [SMILES: CCOCCn1nc(C)c2nc(N3CCN[C@H](C)C3)nc(Nc3ccc(OC)nc3)c21] | 0.56 |

TABLE B-continued
| WO2004096810 EXAMPLE NO. | STRUCTURE | METHOD 1: PDE5 IC$_{50}$ (nM) |
|---|---|---|
| 195 | 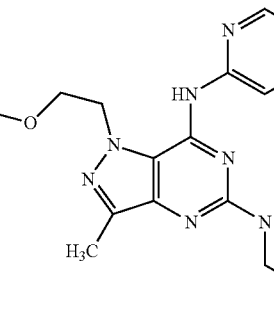 | 0.96 |
| 196 | 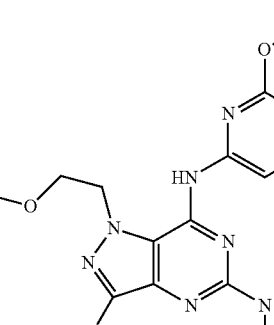 | 0.56 |
| 197 | 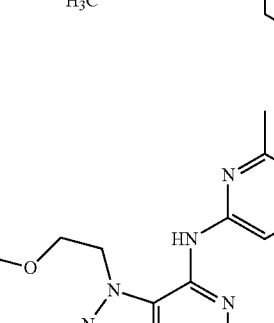 | 1.76 |
| 198 | 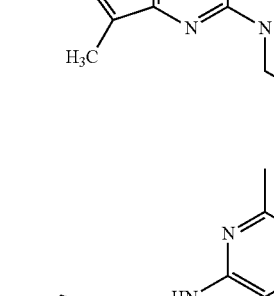 | 10.0 |

TABLE B-continued

| WO2004096810 EXAMPLE NO. | STRUCTURE | METHOD 1: PDE5 IC$_{50}$ (nM) |
|---|---|---|
| 199 | 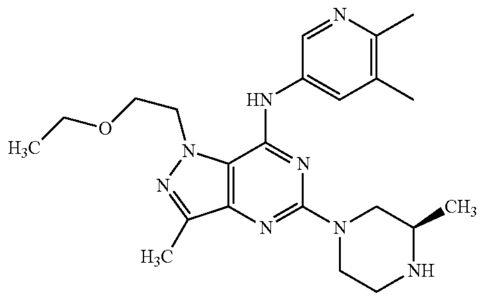 [SMILES: CCOCCn1nc(C)c2nc(N3CCN[C@H](C)C3)nc(Nc3cnc(C)c(C)c3)c21] | 3.13 |
| 200 | 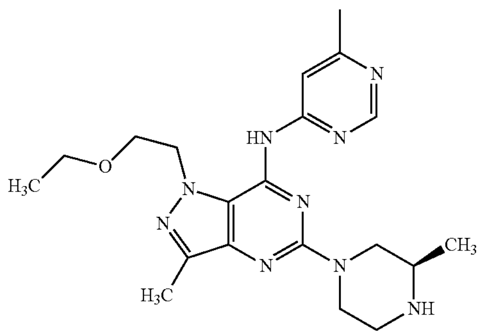 [SMILES: CCOCCn1nc(C)c2nc(N3CCN[C@H](C)C3)nc(Nc3cc(C)ncn3)c21] | 4.70 |
| 201 | 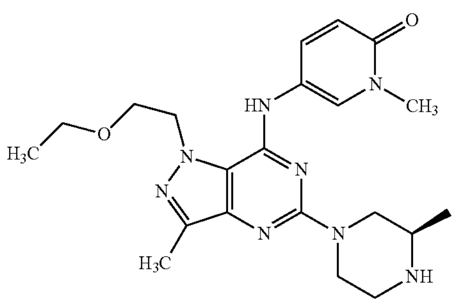 [SMILES: CCOCCn1nc(C)c2nc(N3CCN[C@H](C)C3)nc(Nc3ccc(=O)n(C)c3)c21] | 25.9 |
| 202 | 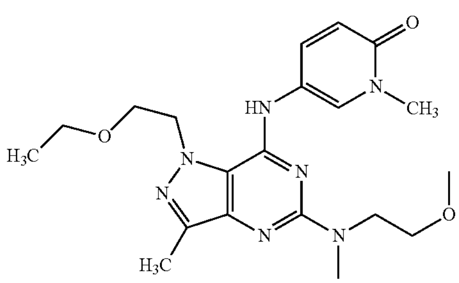 [SMILES: CCOCCn1nc(C)c2nc(N(C)CCOC)nc(Nc3ccc(=O)n(C)c3)c21] | 5.46 |
| 203 | 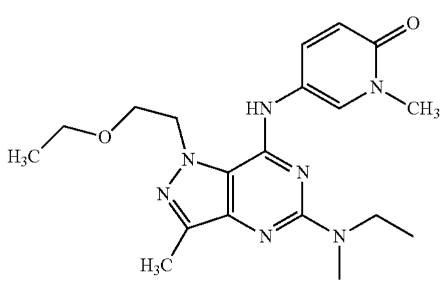 [SMILES: CCOCCn1nc(C)c2nc(N(C)CC)nc(Nc3ccc(=O)n(C)c3)c21] | 0.63 |

TABLE B-continued

| WO2004096810 EXAMPLE NO. | STRUCTURE | METHOD 1: PDE5 IC$_{50}$ (nM) |
|---|---|---|
| 204 | 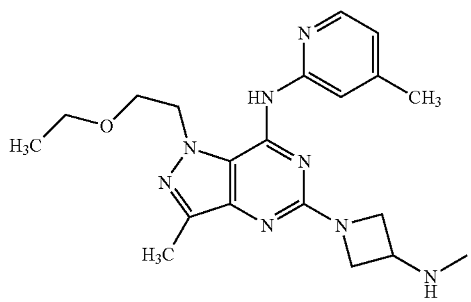 [SMILES: CCOCCn1nc(C)c2nc(N3CC(NC)C3)nc(Nc3cc(C)ccn3)c21] | 24.1 |
| 205 | 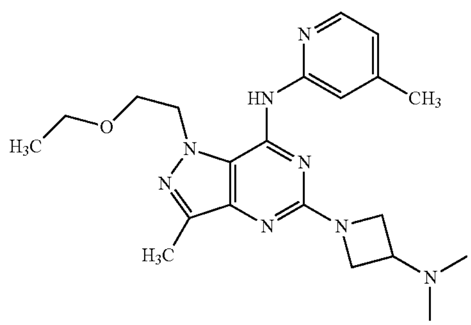 [SMILES: CCOCCn1nc(C)c2nc(N3CC(N(C)C)C3)nc(Nc3cc(C)ccn3)c21] | 6.24 |
| 206 | 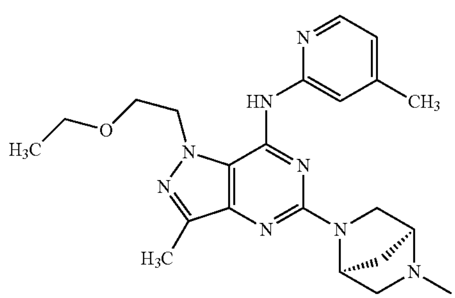 [SMILES: CCOCCn1nc(C)c2nc(N3C[C@@H]4C[C@H]3CN4C)nc(Nc3cc(C)ccn3)c21] | 6.09 |
| 207 | 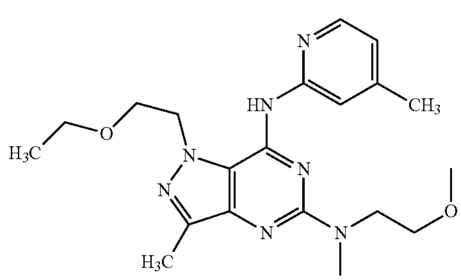 [SMILES: CCOCCn1nc(C)c2nc(N(C)CCOC)nc(Nc3cc(C)ccn3)c21] | 1.55 |
| 208 | 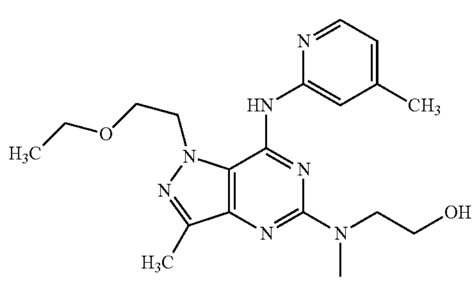 [SMILES: CCOCCn1nc(C)c2nc(N(C)CCO)nc(Nc3cc(C)ccn3)c21] | 0.71 |

TABLE B-continued
| WO2004096810 EXAMPLE NO. | STRUCTURE | METHOD 1: PDE5 IC$_{50}$ (nM) |
|---|---|---|
| 210 | 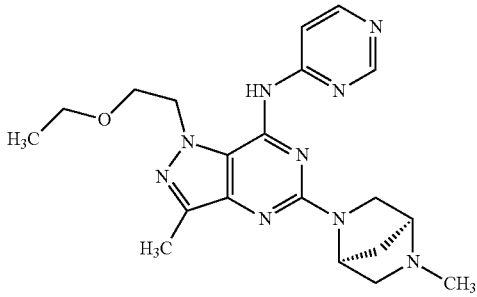 [SMILES: CCOCCn1nc(C)c2nc(N3C[C@@H]4C[C@H]3CN4C)nc(Nc3ccncn3)c21] | 82.7 |
| 211 | 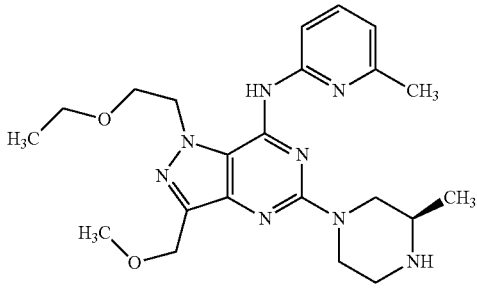 [SMILES: CCOCCn1nc(COC)c2nc(N3CCN[C@H](C)C3)nc(Nc3cccc(C)n3)c21] | 1.57 |
| 212 | 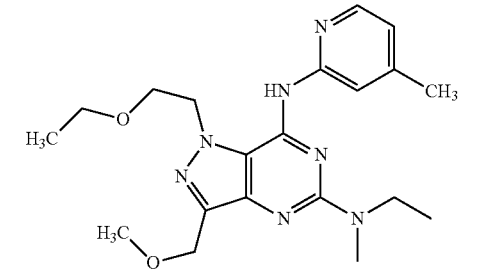 [SMILES: CCOCCn1nc(COC)c2nc(N(C)CC)nc(Nc3cc(C)ccn3)c21] | 0.13 |
| 213 | 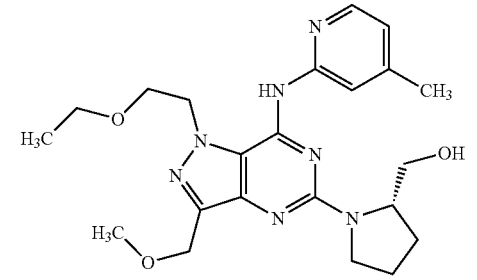 [SMILES: CCOCCn1nc(COC)c2nc(N3CCC[C@H]3CO)nc(Nc3cc(C)ccn3)c21] | 0.42 |
| 214 | 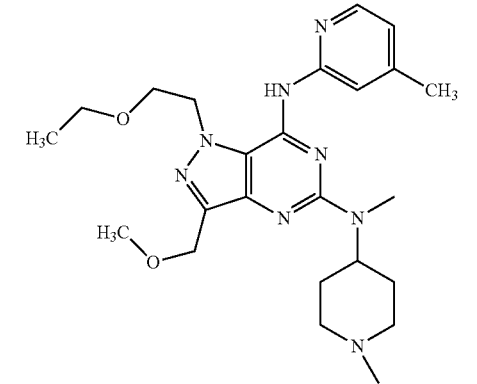 [SMILES: CCOCCn1nc(COC)c2nc(N(C)C3CCN(C)CC3)nc(Nc3cc(C)ccn3)c21] | 0.37 |

TABLE B-continued

| WO2004096810 EXAMPLE NO. | STRUCTURE | METHOD 1: PDE5 IC$_{50}$ (nM) |
|---|---|---|
| 215 | 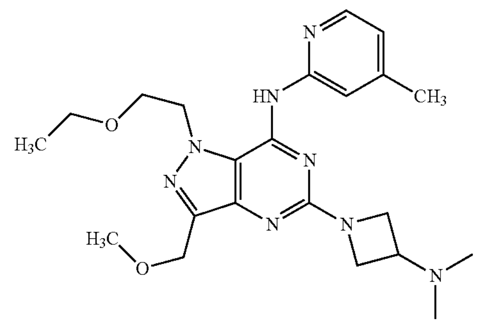 [SMILES: CCOCCn1nc(COC)c2nc(N3CC(N(C)C)C3)nc(Nc3cc(C)ccn3)c21] | 5.30 |
| 216 | 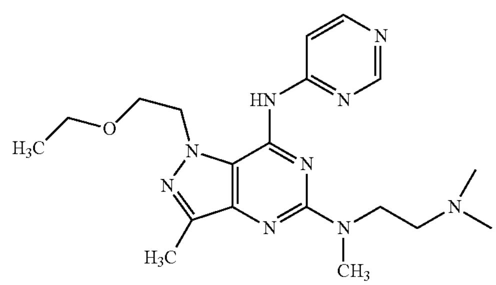 [SMILES: CCOCCn1nc(C)c2nc(N(C)CCN(C)C)nc(Nc3ccncn3)c21] | 60.9 |
| 217 | 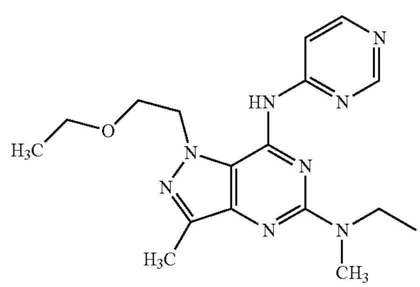 [SMILES: CCOCCn1nc(C)c2nc(N(C)CC)nc(Nc3ccncn3)c21] | 2.55 |
| 218 | 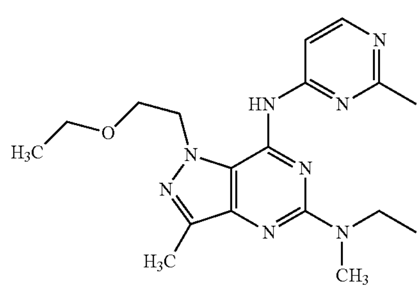 [SMILES: CCOCCn1nc(C)c2nc(N(C)CC)nc(Nc3ccnc(C)n3)c21] | 11.5 |
| 219 | 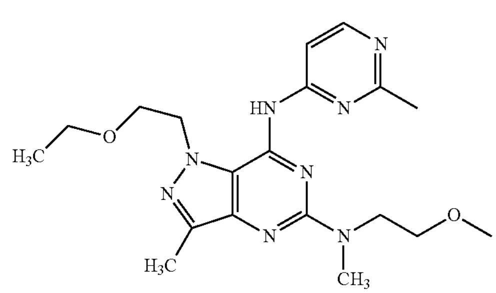 [SMILES: CCOCCn1nc(C)c2nc(N(C)CCOC)nc(Nc3ccnc(C)n3)c21] | 41.0 |

TABLE B-continued

| WO2004096810 EXAMPLE NO. | STRUCTURE | METHOD 1: PDE5 IC$_{50}$ (nM) |
|---|---|---|
| 220 | 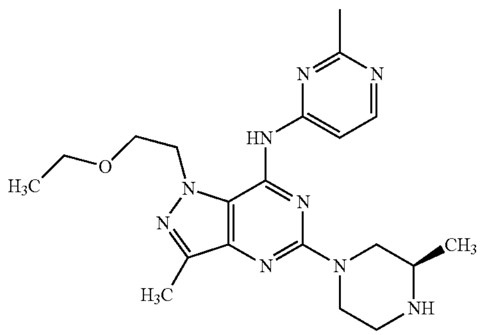 [SMILES: CCOCCn1nc(C)c2nc(N3CCN[C@H](C)C3)nc(Nc3ccnc(C)n3)c21] | 3.60 |
| 221 | 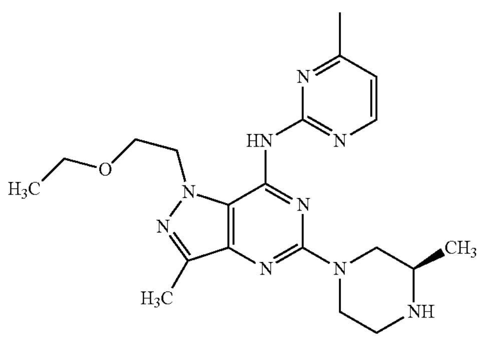 [SMILES: CCOCCn1nc(C)c2nc(N3CCN[C@H](C)C3)nc(Nc3nccc(C)n3)c21] | 35.4 |
| 222 | 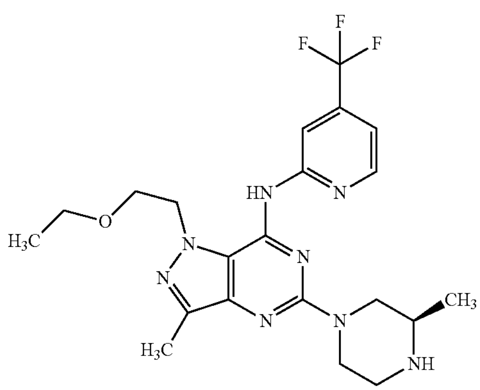 [SMILES: CCOCCn1nc(C)c2nc(N3CCN[C@H](C)C3)nc(Nc3cc(C(F)(F)F)ccn3)c21] | 10.1 |
| 225 | 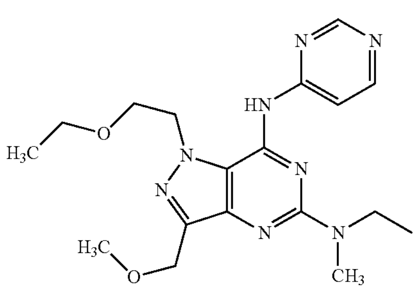 [SMILES: CCOCCn1nc(COC)c2nc(N(C)CC)nc(Nc3ccncn3)c21] | 1.33 |

TABLE B-continued

| WO2004096810 EXAMPLE NO. | STRUCTURE | METHOD 1: PDE5 IC$_{50}$ (nM) |
|---|---|---|
| 226 | 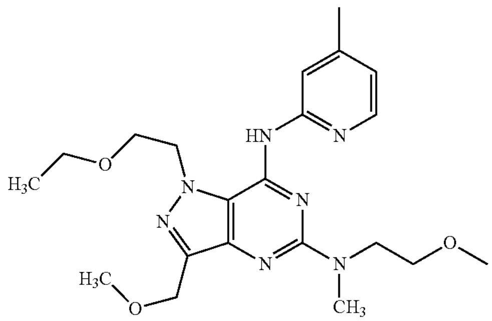 [SMILES: CCOCCn1nc(COC)c2nc(N(C)CCOC)nc(Nc3cc(C)ccn3)c21] | 0.83 |
| 227 | 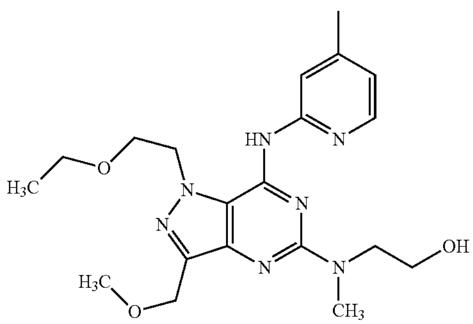 [SMILES: CCOCCn1nc(COC)c2nc(N(C)CCO)nc(Nc3cc(C)ccn3)c21] | 0.35 |
| 228 | 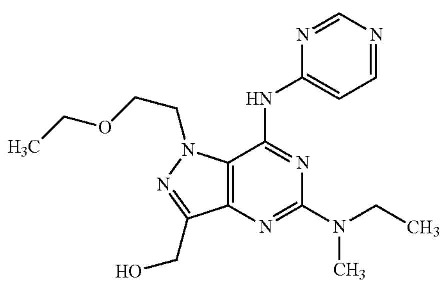 [SMILES: CCOCCn1nc(CO)c2nc(N(C)CC)nc(Nc3ccncn3)c21] | 3.09 |
| 229 | 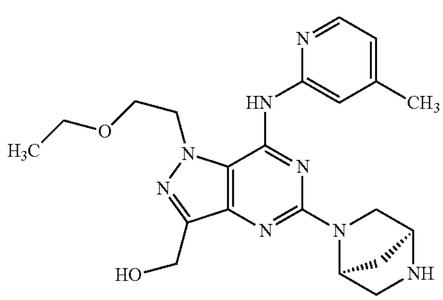 [SMILES: CCOCCn1nc(CO)c2nc(N3C[C@@H]4C[C@H]3CN4)nc(Nc3cc(C)ccn3)c21] | 1.61 |
| 231 | 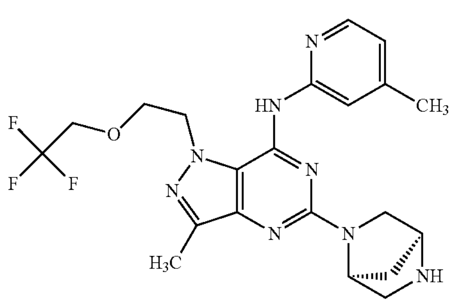 [SMILES: Cc1ccnc(Nc2nc(N3C[C@@H]4C[C@H]3CN4)nc3c(C)nn(CCOCC(F)(F)F)c23)c1] | 10.3 |

TABLE B-continued

| WO2004096810 EXAMPLE NO. | STRUCTURE | METHOD 1: PDE5 IC$_{50}$ (nM) |
|---|---|---|
| 233 | 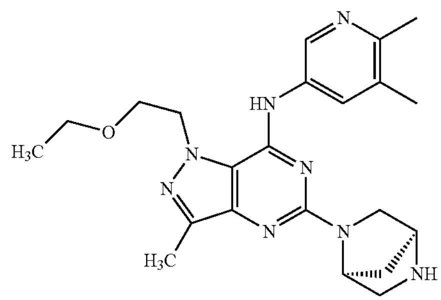 [SMILES: CCOCCn1nc(C)c2nc(N3C[C@@H]4C[C@H]3CN4)nc(Nc3cnc(C)c(C)c3)c21] | 3.85 |
| 234 | 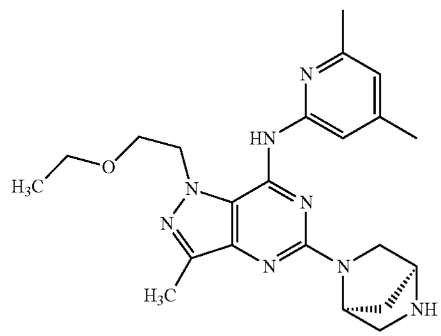 [SMILES: CCOCCn1nc(C)c2nc(N3C[C@@H]4C[C@H]3CN4)nc(Nc3cc(C)cc(C)n3)c21] | 8.79 |
| 235 | 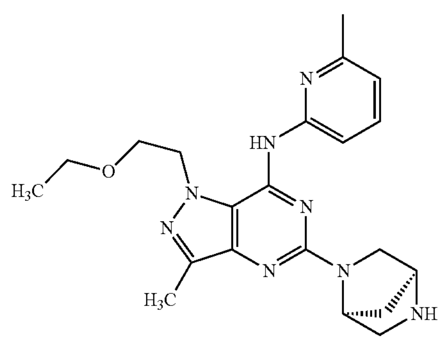 [SMILES: CCOCCn1nc(C)c2nc(N3C[C@@H]4C[C@H]3CN4)nc(Nc3cccc(C)n3)c21] | >100 |
| 236 | 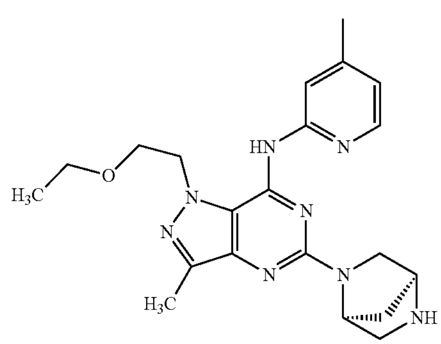 [SMILES: CCOCCn1nc(C)c2nc(N3C[C@@H]4C[C@H]3CN4)nc(Nc3cc(C)ccn3)c21] | 2.51 |

TABLE B-continued

| WO2004096810 EXAMPLE NO. | STRUCTURE | METHOD 1: PDE5 IC$_{50}$ (nM) |
|---|---|---|
| 237 | 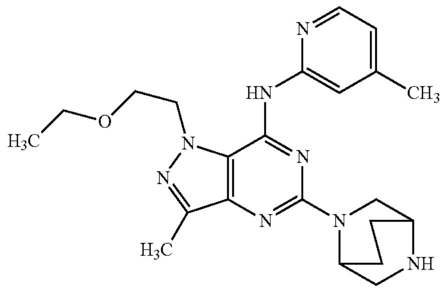 [SMILES: CCOCCn1nc(C)c2nc(N3CC4CCC3CN4)nc(Nc3cc(C)ccn3)c21] | 0.67 |
| 240 | 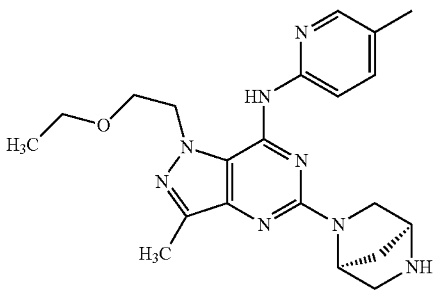 [SMILES: CCOCCn1nc(C)c2nc(N3C[C@@H]4C[C@H]3CN4)nc(Nc3ccc(C)cn3)c21] | >100 |
| 241 | 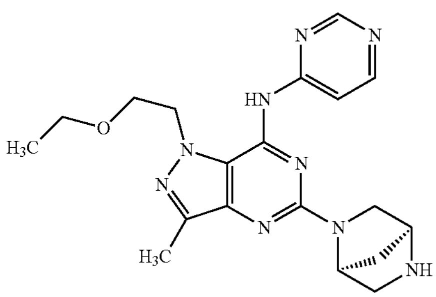 [SMILES: CCOCCn1nc(C)c2nc(N3C[C@@H]4C[C@H]3CN4)nc(Nc3ccncn3)c21] | 48.7 |
| 242 | 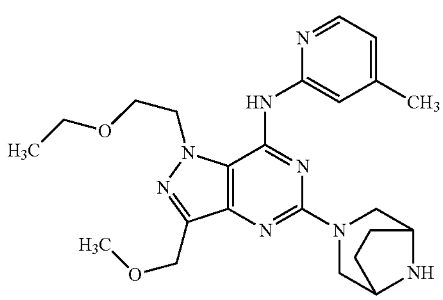 [SMILES: CCOCCn1nc(COC)c2nc(N3CC4CCC(C3)N4)nc(Nc3cc(C)ccn3)c21] | 0.62 |
| 244 | 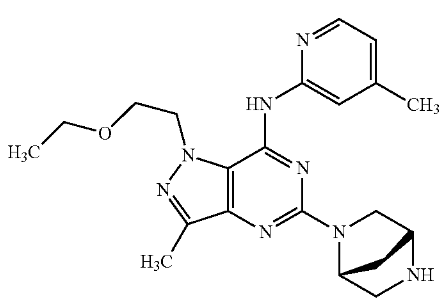 | 2.54 |

TABLE B-continued
| WO2004096810 EXAMPLE NO. | STRUCTURE | METHOD 1: PDE5 IC$_{50}$ (nM) |
|---|---|---|
| 245 | 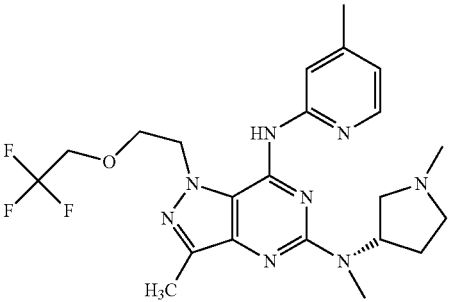 | 1.55 |
| 246 | 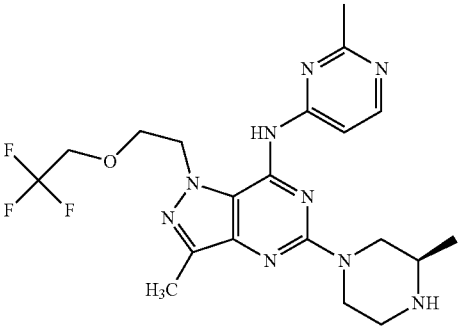 [SMILES: Cc1nccc(Nc2nc(N3CCN[C@H](C)C3)nc3c(C)nn(CCOCC(F)(F)F)c23)n1] | 4.46 |
| 248 | 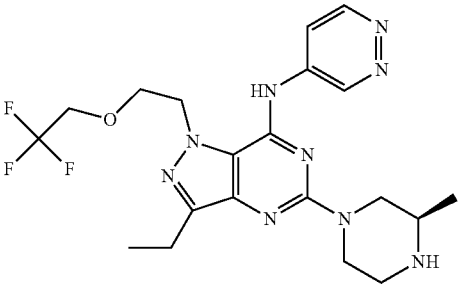 [SMILES: CCc1nn(CCOCC(F)(F)F)c2c(Nc3ccnnc3)nc(N3CCN[C@H](C)C3)nc12] | 0.30 |
| 249 | 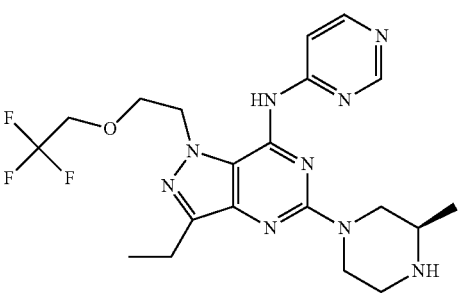 [SMILES: CCc1nn(CCOCC(F)(F)F)c2c(Nc3ccncn3)nc(N3CCN[C@H](C)C3)nc12] | 0.16 |
| 250 | 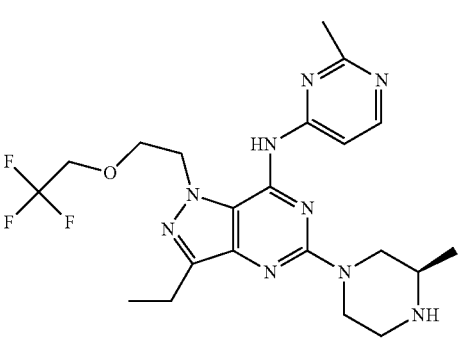 [SMILES: CCc1nn(CCOCC(F)(F)F)c2c(Nc3ccnc(C)n3)nc(N3CCN[C@H](C)C3)nc12] | 2.37 |

TABLE B-continued

| WO2004096810 EXAMPLE NO. | STRUCTURE | METHOD 1: PDE5 IC$_{50}$ (nM) |
|---|---|---|
| 251 | 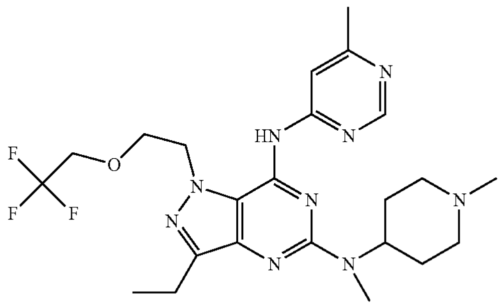 [SMILES: CCc1nn(CCOCC(F)(F)F)c2c(Nc3cc(C)ncn3)nc(N(C)C3CCN(C)CC3)nc12] | 0.25 |
| 252 | 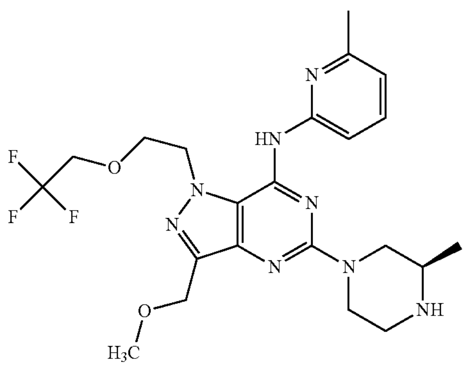 [SMILES: COCc1nn(CCOCC(F)(F)F)c2c(Nc3cccc(C)n3)nc(N3CCN[C@H](C)C3)nc12] | 2.81 |
| 253 | 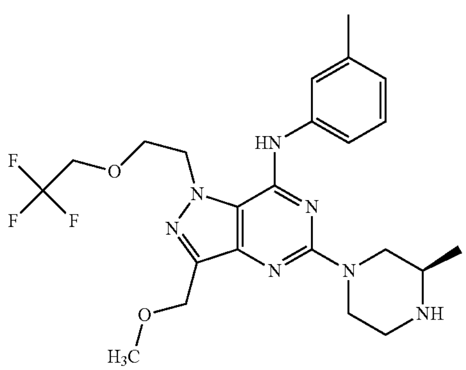 [SMILES: COCc1nn(CCOCC(F)(F)F)c2c(Nc3cccc(C)c3)nc(N3CCN[C@H](C)C3)nc12] | 1.20 |
| 254 | 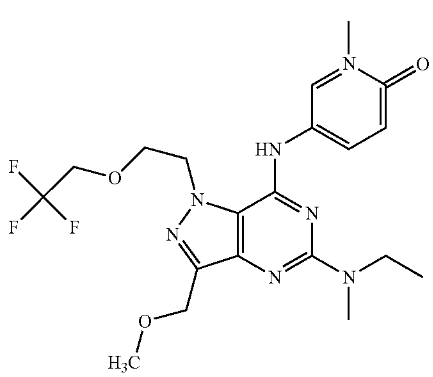 | 0.59 |

TABLE B-continued

| WO2004096810 EXAMPLE NO. | STRUCTURE | METHOD 1: PDE5 IC$_{50}$ (nM) |
|---|---|---|
| 255 | 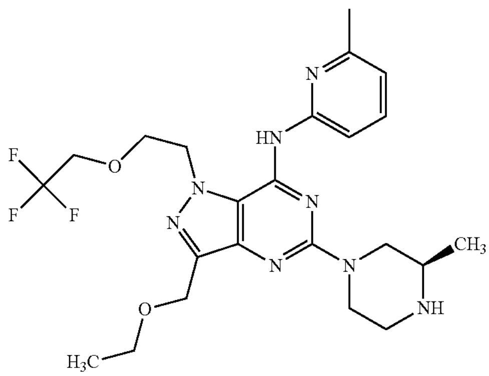 [SMILES: CCOCc1nn(CCOCC(F)(F)F)c2c(Nc3cccc(C)n3)nc(N3CCN[C@H](C)C3)nc12] | 1.43 |
| 256 | 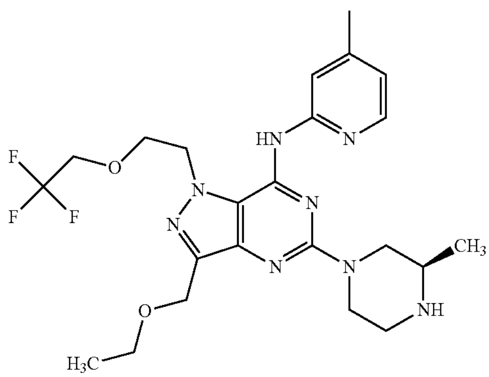 [SMILES: CCOCc1nn(CCOCC(F)(F)F)c2c(Nc3cc(C)ccn3)nc(N3CCN[C@H](C)C3)nc12] | 3.82 |
| 258 | 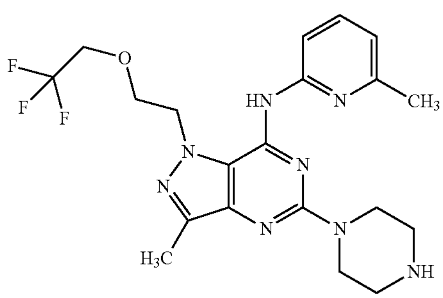 [SMILES: Cc1cccc(Nc2nc(N3CCNCC3)nc3c(C)nn(CCOCC(F)(F)F)c23)n1] | 1.99 |
| 259 | 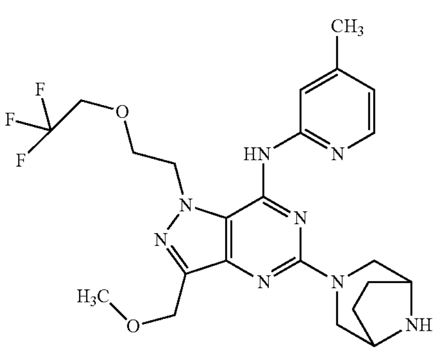 [SMILES: COCc1nn(CCOCC(F)(F)F)c2c(Nc3cc(C)ccn3)nc(N3CC4CCC(C3)N4)nc12] | 3.74 |

TABLE B-continued

| WO2004096810 EXAMPLE NO. | STRUCTURE | METHOD 1: PDE5 IC$_{50}$ (nM) |
|---|---|---|
| 261 | 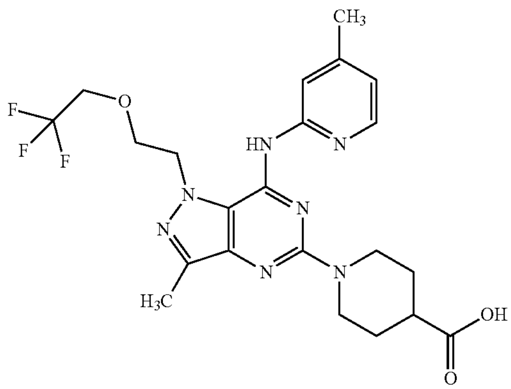 [SMILES: Cc1ccnc(Nc2nc(N3CCC(C(=O)O)CC3)nc3c(C)nn(CCOCC(F)(F)F)c23)c1] | 0.57 |
| 262 | 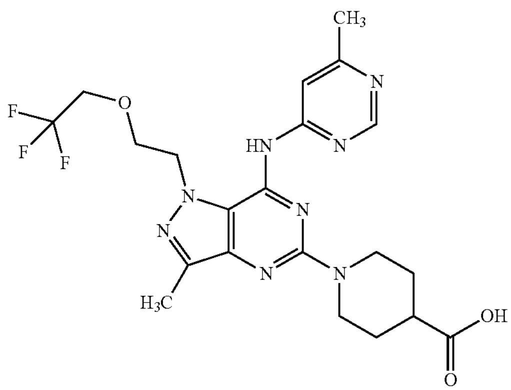 [SMILES: Cc1cc(Nc2nc(N3CCC(C(=O)O)CC3)nc3c(C)nn(CCOCC(F)(F)F)c23)ncn1] | 0.93 |
| 263 | 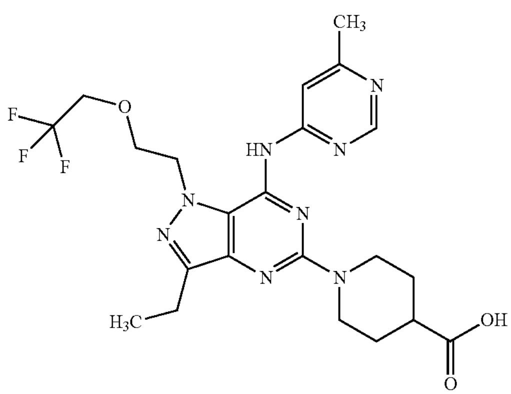 [SMILES: CCc1nn(CCOCC(F)(F)F)c2c(Nc3cc(C)ncn3)nc(N3CCC(C(=O)O)CC3)nc12] | 0.27 |

Method 1A: Alternative Human Platelet PDE5 Enzyme Inhibition Scintillation Proximity Assay The PDE5 IC$_{50}$ of a test compound also can be measured in an alternative in vitro assay that varies from Method 1 as described below:

PDE5 IC$_{50}$ Assay: 96-Well Microtiter Plate Format

Reagents
Buffer A: 20 mM Tris-HCl, 5 mM MgCl$_2$, pH 7.4
Buffer B: 2 mg/ml BSA in Buffer A (enzyme buffer)
cGMP substrate: Final concentration of 50 nM in assay
The amount of $^3$H-labeled substrate added depends upon the specific activity of [$^3$H]cGMP, and it is diluted in Buffer A.

PDE enzyme: Prepared in Buffer B. The dilution factor is determined by enzyme activity.
SPA beads: 4 mg/ml suspension prepared in dH$_2$O.

| Positive Control | Negative Control | Standard/Test compound |
|---|---|---|
| 3 μl 100% DMSO | 3 μl 100% DMSO | 3 μl Standard/Test compound |
| 27 μl Buffer A | 27 μl Buffer A | 27 μl Buffer A |
| 30 μl Enzyme | 30 μl Buffer B | 30 μl Enzyme |
| 30 μl Substrate | 30 μl Substrate | 30 μl Substrate |
| 30 μl SPA to stop | 30 μl SPA to stop | 30 μl SPA to stop |

Stocks of standard and test compound are prepared at 2 mM in 100% DMSO. The test compound is serially diluted in a dilution plate using a 10-point ⅕ log dilution format such that the starting concentration in the assay is 2 μM for an initial $IC_{50}$ screen; confirmatory $IC_{50}$s are done using a 10-point ⅓ log dilution. 27 μl of Buffer A are added to the wells of the assay plates. From the dilution plate, 3 μl of diluted compound is delivered in duplicate or 3 μl of 100% DMSO (for positive and negative controls) are added. 30 μl of enzyme are added. For the negative control wells, Buffer B is substituted in place of the enzyme. 30 μl of labeled substrate are added to all wells.

After incubating for 60 minutes at room temperature, the reaction is stopped with the addition of 30 μl of the yttrium silicate beads. These beads are dense and require constant agitation while being added to the plate. The plates are sealed and shaken on a plate shaker for fifteen minutes to allow the beads to bind the GMP product.

After allowing the beads to settle for 30 minutes, plates are read on a NXT TopCount scintillation counter and the data are analyzed as follows. Percent inhibition values are calculated using the means of the 0% and 100% controls on each plate. The estimates of the 4-parameters of the logistic, sigmoid dose-response model are then calculated using the well-level percent inhibition value for the compound. The formula for the four-parameter logistic model may be expressed as $Y=((a-d)/(1+(X/c)^b))+d$, where Y is the response, X is the concentration, a is the lower asymptote (minimum response), d is the upper asymptote (maximum response), c is the model $IC_{50}$ (in the same units as X), and b is the slope (as described in De Lean, A., P. J. Munson, and D. Rodbard ("Simultaneous analysis of families of sigmoidal curves: application to bioassay, radioligand assay, and physiological dose-response curves." Am. J. Physiol. 235(2): E97-E102, 1978). These estimates are used to calculate the concentration that corresponds to 50% inhibition.

The Carboxypiperidine Compound was tested in accordance with Method 1a. The corresponding PDE5 $IC_{50}$ values measured are reported in Table C.

TABLE C

| RUN NO. | METHOD 1A: PDE5 $IC_{50}$ (nM) |
| --- | --- |
| 1 | 0.051 |
| 2 | 0.051 |
| 3 | 0.039 |
| 4 | 0.045 |
| 5 | 0.023 |
| 6 | 0.026 |
| AVERAGE: | 0.039 |

Compounds previously disclosed in examples from WO2004096810 were tested in accordance with Method 1a. The corresponding PDE5 $IC_{50}$ values measured are reported in Table D.

TABLE D

| WO2004096810 EXAMPLE NO. | METHOD 1a: PDE5 $IC_{50}$ (nM) |
| --- | --- |
| 261 | 0.115 |
| 262 | 0.0755 |
| 263 | 0.0197 |

Method 2: Human Retina PDE6 Enzyme Inhibition Scintillation Proximity Assay (SPA)

The inhibition of PDE6 enzyme activity by a test compound can be measured in accordance with the in vitro assay of Method 1, but instead using semi-purified PDE6 enzyme isolated from human, bovine or canine retina in place of PDE5 enzyme. This assay measures the PDE6 $IC_{50}$ value for the test compound (i.e., the concentration of the test compound required to inhibit by 50% the PDE6 enzyme-catalyzed hydrolysis of [$^3$H]cGMP to the 5' nucleotide [$^3$H]GMP relative to the activity of uninhibited controls). [3H]GMP binds to yttrium silicate SPA beads and is detected by scintillation counting.

PDE6 Purification: PDE6 can be isolated and purified from the following: Soluble rod PDE6/Rod Outer Segment PDE6 from Bovine eyes (Charles River Ltd, France); Cone PDE6 from Canine eyes (LAS); or Soluble rod and Cone PDE6 from Human eyes (I.I.A.M.).

Homogenisation Buffer 20 mM Hepes (Sigma) 2.383 gms
1 mM EDTA (Sigma) 0.186 gms
Dissolve in 300 ml of HPLC (Acros) or double deionised water.
100 mM PMSF (Sigma) 0.174 gms/10 mls ethanol
Add 5 ml of PMSF solution to buffer slowly to avoid precipitation.
Add 250 mM Sucrose (Fisher) 42.78 gms
Adjust volume to 500 ml, stir until dissolved.
Adjust pH to 7.2 using 1M NaOH.
Store at 4° C.
Preparation of the Retina: Allow the eyes to thaw until soft and until the cornea and lens are clear. While supporting the eye with the cornea uppermost, make a small incision through the conjunctiva below the level of the iris. The incision should be sufficient to allow the humor to escape through the cut. Using fine scissors, cut around the cornea to enable it to be lifted off as a flap. Using a small hook, engage the lens and gently pull it out of orbit, taking care not to pull out the retina at the same time. Allow the retina to drop down of its own accord to the base of the orbit.

Lift the retina with care and locate the optic nerve. Cut through the optic nerve and transfer the retina to a small dish containing a few ml of homogenisation buffer. Gently float the retina out on the surface of the buffer and remove any obvious pigmented material from the iris. Place the retina in a second dish with clean buffer to remove last traces of pigment and then transfer to a 50 ml Corning Costar centrifuge tube (Sigma) and keep on ice.

PDE6 Isolation and Purification from Retina: Allow 2 mls of the homogenisation buffer per bovine retina and 1 ml per retina for dog and human. Homogenise using hand-held homogeniser 3×5 second bursts cooling on ice between each burst. Filter homogenate through two layers of surgical gauze. Spin at 100,000 g for 60 minutes at 4° C. Filter cytosol either through a 0.22 μM Steril-D pack if there is sufficient volume or through a 0.22 μM syringe-end filter (e.g., Millex®-GV). Run through FPLC (Pharmacia FPLC LKB/FRAC-100, Pharmacia) or aliquot and store in liquid nitrogen as needed.

Method 2A: Alternative Human Retina PDE6 Enzyme Inhibition Scintillation Proximity Assay (SPA)

The inhibition of PDE6 enzyme activity by a test compound also can be measured in accordance with the in vitro assay of Method 1A, but instead using semi-purified PDE6 enzyme isolated from human, bovine or canine retina in place of PDE5 enzyme. This assay measures the PDE6 $IC_{50}$ value for the test compound (i.e., the concentration of the test compound required to inhibit by 50% the PDE6 enzyme-catalyzed hydrolysis of [$^3$H]cGMP to the 5' nucleotide [$^3$H]GMP relative to the activity of uninhibited controls). [3H]GMP binds to yttrium silicate SPA beads and is detected by scintillation counting.

Method 3: Human Recombinant PDE11 Enzyme Inhibition Scintillation Proximity Assay (SPA)

The inhibition of PDE11 enzyme activity by a test compound can be measured in accordance with the in vitro assay of Method 1, but instead using PDE11 enzyme expressed in Sf9 insect cells in place of PDE5 enzyme. This assay measures the PDE11 $IC_{50}$ value for the test compound (i.e., the concentration of the test compound required to inhibit by 50% the PDE11 enzyme-catalyzed hydrolysis of [$^3$H]cGMP to the 5' nucleotide [$^3$H]GMP relative to the activity of uninhibited controls). [3H]GMP binds to yttrium silicate SPA beads and is detected by scintillation counting.

PDE11 Expression and Purification:

(a) Expression: Infect 200 ml of Sf9 insect cells (Invitrogen, Carlsbad, Calif.) ($1\times10^6$/ml) with a multiplicity of infection of 2 using a baculovirus expression vector containing transposed PDE-11A1 (SEQ ID NO: 1) (pFastBac system, Invitrogen) ($4\times10^7$ pfu/ml). Incubate at 27° C. with 220 rpm shaking for 48 hours. Harvest the infected cells by pelleting at 2000 rpm for 10 minutes at 4° C. Store the infected cell pellet at −80° C. until ready for purification. Resuspend the thawed cell pellets to $1\times10^7$ cells/ml (=20 ml buffer consisting of 20 mM Hepes (pH7.2), 1 mM EDTA, 20 mM sucrose, 150 mM NaCl and protease inhibitor tablets). Mix thoroughly and allow to stand on ice for 10 minutes. Sonicate for 5×5 seconds, on ice. Spin the mixture at 12,000 rpm for 10 minutes at 4° C. in SS34. Store the insoluble pellet at −80° C., and proceed to the purification of the soluble material.

(b) Purification: Prepare the column (1.0 cm diameter, Kontes) by rinsing the empty column twice with TBS. Then mix beads (Anti-FLAG M2 Agarose, Sigma) with TBS and add to the column—allow the beads to settle. Wash the column with 3 column volumes of 0.1M glycine (pH3.5). Then wash the column with 5 column volumes of TBS (do not allow to run dry). Apply the extract to the column and allow the extract to enter by gravity flow. Reapply the flow-through. Wash the column with 15 column volumes of TBS. Elute the protein with 5×1 ml aliquots of FLAG peptide (Sigma) (i.e., 100 ug/ml in TBS). Elute the remaining protein with 1 ml 0.1M glycine, and immediately add 25 ul 1M Tris pH8 to neutralize.

Method 3A: Alternative Human Recombinant PDE11 Enzyme Inhibition Scintillation Proximity Assay (SPA)

The inhibition of PDE11 enzyme activity by a test compound also can be measured in accordance with the in vitro assay of Method 1A, but instead using PDE11 enzyme expressed in Sf9 insect cells in place of PDE5 enzyme. This assay measures the PDE11 $IC_{50}$ value for the test compound (i.e., the concentration of the test compound required to inhibit by 50% the PDE11 enzyme-catalyzed hydrolysis of [$^3$H]cGMP to the 5' nucleotide [$^3$H]GMP relative to the activity of uninhibited controls). [3H]GMP binds to yttrium silicate SPA beads and is detected by scintillation counting.

The Carboxypiperidine Compound was tested in accordance with Method 2, Method 2A, Method 3, and Method 3A. The corresponding PDE6 and PDE11 $IC_{50}$ values measured are reported in Table E.

TABLE E

| RUN NO. | METHOD 2: PDE6 $IC_{50}$ (nM) | METHOD 2A: PDE6 $IC_{50}$ (nM) | METHOD 3: PDE11 $IC_{50}$ (nM) | METHOD 3A: PDE11 $IC_{50}$ (nM) |
|---|---|---|---|---|
| 1 | 4.01 | 5.12 | 19.5 | 14.3 |
| 2 | 3.89 | 2.43 | 20.0 | 16.5 |
| 3 |  | 4.88 |  | 16.8 |
| 4 |  | 2.12 |  | 26.0 |
| 5 |  | 5.74 |  | 28.4 |
| 6 |  | 3.72 |  | 19.6 |
| AVERAGE: | 3.95 | 3.74 | 19.8 | 19.7 |

Compounds previously disclosed in examples from WO2004096810 were tested in accordance with Method 2, Method 2A, Method 3, and Method 3A. The corresponding PDE6 and PDE11 $IC_{50}$ values measured are reported in Table F.

TABLE F

| WO2004096810 EXAMPLE NO. | METHOD 2: PDE6 $IC_{50}$ (nM) | METHOD 2a: PDE6 $IC_{50}$ (nM) | METHOD 3: PDE11 $IC_{50}$ (nM) | METHOD 3a: PDE11 $IC_{50}$ (nM) |
|---|---|---|---|---|
| 245 | 250 |  | 390 |  |
| 246 | 657 |  | 4320 |  |
| 248 | 9.92 |  | 316 |  |
| 249 | 5.10 |  | 1190 |  |
| 250 | 221 |  | 3120 |  |
| 251 | 9.51 |  | 1862 |  |
| 252 | 307 |  | 874 |  |
| 253 | 100 |  | 312 |  |
| 254 | 188 |  | 2880 |  |
| 255 | 207 |  | 937 |  |
| 256 | 275 |  | 913 |  |
| 258 | 198 |  | 215 |  |
| 259 | 204 |  | 199 |  |
| 261 | 58.8 | 110 | 426 | 585 |
| 262 | 47.7 | 66.3 | 471 | 608 |
| 263 | 25.3 | 30.6 | 316 | 384 |

Additional assays that can be used to evaluate the effectiveness of a test compound include Method 4, Method 4A, Method 5 and Method 6 described below:

Method 4: Aortic Rind Assay

An ex vivo assay can be used to measure the direct relaxation of a rat aortic ring exposed to a test compound. As more specifically described below, a test compound that inhibits PDE5 activity elicits a relaxation of the aortic ring by enhancing the cGMP signal (i.e., by inhibiting PDE5 enzyme-catalyzed hydrolysis of cGMP to GMP) evoked when the aortic ring is exposed to a stable exogenous nitric oxide donor, such as diethyltriamine NONOate (diazen-1-ium-1,2-diolate, also known as "DETA-NO"). The assay measures the $EC_{50}$ value for the test compound (i.e., the concentration of the test compound which produces 50% of the maximum possible effective response for the test compound).

Male Sprague-Dawley rats (250-350 g) are asphyxiated using $CO_2$ gas and their thoracic aortas carefully excised and placed in Krebs buffer. The aortas are then carefully dissected free of connective tissue and divided into 8 sections, each 3-4 mm in length.

Aortic rings are suspended between parallel stainless steel wires in a water jacketed (37° C.), 15 mL tissue bath under a resting tension of 1 gram. Tension is measured using isometric tension transducers and recorded using Ponemah tissue platform system. Each preparation is allowed to equilibrate for at least 60 minutes prior to compound testing. During this time, the tissues are also incubated with 200 uM NG-monomethyl L-arginine ("L-NMMA"), and the incubation media changed every 15 to 20 minutes (L-NMMA is added after each wash to maintain the final concentration at 200 uM in each tissue bath).

Following the equilibration period, baseline tensions are recorded for each tissue. The vasoconstrictor response to phenylepherine (1 uM) is assessed and when the response to phenylepherine reaches a maximum, vascular reactivity is subsequently assessed by a challenge of acetylcholine (1 uM). Following another washout period, a second baseline value is recorded after adding the vasoconstrictor noradrenaline (25 nM) to each bath and incubating the tissues for a time period (about 15 minutes) sufficient for the tissues to achieve a stable tone. An exogenous nitric oxide drive is supplied using the stable nitric oxide donor, DETA-NO. The concentration of DETA-NO is titrated (cumulatively in half-log increments) to achieve approximately 5 to 15% relaxation of the noradrenaline-evoked preconstriction. Cumulative concentration-response curves are constructed in a single ring, typically using 5 doses/ring and allowing 15 minutes between each addition.

Method 4A: Alternative Aortic Ring Assay

Method 4 can be modified to provide an alternative protocol for measuring the direct relaxation of rat aortic rings exposed to a test compound. This alternative method varies from Method 4 as described below:

For the alternative method, the endothelium is first removed by gently rubbing the lumen of the vessel together between the fingers prior to preparing the rings (denuded rings). The resting tension is set at 2 grams and the vasoconstrictor response to a maximal concentration of phenylepherine (1 µM) is assessed, followed (after a washout period) by two further exposures to 300 nM of pheylephrine. The concentration-response relationship to noradrenaline is constructed in each tissue over concentration range 0.1 to 300 nM. After another washout period, the tissues are constricted with an $EC_{90}$ concentration of noradrenaline for compound testing.

Method 5: Culex™ Assay

The effect of a test compound on systemic arterial blood pressure can be evaluated in a conscious pre-cannulated spontaneously hypertensive rat ("SHR") model. This assay is conducted using an automated blood sampler ("ABS") system. The Culex™ ABS system (Bioanalytical System, Inc., West Lafayette, Ind.) comprises a laptop computer, four control units and metabolic cages. This ABS system allows for the collection of multiple blood samples from a single rat without causing undue stress to the animal. In addition, the ABS system allows for the collection of urine samples that can be potentially used for biomarker identifications. Through this approach, efficacy and standard pharmacokinetic studies are conducted in the conscious unrestrained SHR rats simultaneously to define the relationship between plasma free drug concentration or potential biomarker(s) and pharmacological effect (reduction of mean arterial blood pressure).

SHR rats at 12 to 16 weeks of age, weighing about 300 g, undergo surgerical cannulation of both jugular veins and the right carotid artery. After surgical recovery, animals are placed in the Culex™ cages and tethered to a movement-responsive arm with a sensor that controls cage movement when the animal moves to prevent the catheters from being twisted. Connections are made between the right jugular catheter and the Culex™ sterile tubing set for blood sampling, and the left jugular catheter for compound administration, and the catheter in the right carotid artery is connected to a pressure transducer for monitoring blood pressure. To keep the patency of the catheters, the right jugular cannula is maintained by the "tend" function of the Culex™ that flushes the catheter with 20 µL heparin saline (10 units/mL) every 12 minutes or between sampling events, and the left jugular cannula is filled with heparin saline (20 units/mL). The patency of the right carotid cannula is maintained by slow infusion of heparin saline either directly into the extend tubing when blood pressure is not recorded or through the pressure transducer during the blood pressure monitoring. Animals are allowed to acclimate for at least two hours before compound evaluation. The test compound may be administered intravenously or by oral gavage. Blood sampling protocols (sampling time and volume) are programmed using the Culex™ software. The total amount of blood withdrawn from each animal will not exceed 750 pU24 hrs and 10 mUkg within two weeks. Heart rate, blood pressure, and drug concentration are monitored. Systemic arterial blood pressure and heart rate are recorded by PONEMAH (Gould Instrument System, Valley View, Ohio), a pressure transducer through a data acquisition system for recording blood pressure and heart rate, for 6 to 24 hours based on experimental protocol. Mean arterial blood pressure (primary endpoint) is analyzed for assessing the efficacy of the compound.

Blood samples are analyzed for measuring plasma drug concentration, using the LC/MS/MS method described below, and for evaluating potential biomarkers.

LC/MS/MS Method

Sample Preparation: Plasma samples (50 µL unknown, control or blank) are mixed with 10 µL acetonitrile:water or a standard solution of the test compound and 150 µL of internal standard solution (100 ng/mL of the test compound in acetonitrile). The mixture is centrifuged at 3000 rpm for 5 min, and 125 µL of the supernatant transferred to a 96 well plate. The solvent is evaporated under a stream of nitrogen and the residue is reconstituted with 80 µL acetonitrile/0.1% aqueous formic acid (20:80 v/v).

A 20 µL volume of each prepared sample is injected onto a Phenomenex Synergi 4 µm MAX-RP 2.0×75 mm column and eluted at 0.4 mL/min using gradient elution from 0.1% aqueous formic acid (mobile phase A) to acetonitrile (mobile phase B). The gradient program consists of initial application of 90% mobile phase A, followed by a linear gradient to 75% mobile phase B from 0.2 to 1.15 min after injection and held at 75% mobile phase B until 2.0 min. The mobile phase was linearly changed back to 90% mobile phase A from 2.00 to 2.10 minutes, and the next injection took place at 3.00 min. Detection was performed by mass spectrometry using positive ion electrospray (ESI) with multiple reaction monitoring of the transitions m/z 454.00 (MH+the test compound)→m/z 408.00, m/z 466.24 (MH+the test compound)→409.33. The ion spray voltagea is set at 5000. A calibration curve is constructed by using peak area ratios of the analyte relative to the internal standard. Subject concentrations are determined by inverse prediction from their peak area ratios against the calibration curve.

Method 6: Implantation of Radio Transmitters and Subsequent Blood Pressure Screening by Telemetry in Spontaneously Hypertensive Rats The effect of a test compound on systemic arterial blood pressure can be evaluated in a spontaneously hypertensive rat ("SHR") model using telemetry. SHR Rats are anesthetized with isoflurane gas via an isoflurane anesthesia machine that is calibrated to deliver isoflurane over a range of percentages as oxygen passes through the machine's inner chambers. The animals are placed in an induction chamber and administered isoflurane at 4-5% to reach a surgical plane of anesthesia. They are then maintained at 1-2% during the surgical procedure via a nose cone, with isoflurane delivered via a smaller isoflurane anesthesia device on the surgical table.

Following administration of anesthesia, the rats are implanted with transmitters using aseptic procedures with commercially available sterile radio-telemetry units (Data Sciences, International, Roseville, Minn. 55113-1136). Prior to surgery the surgical field is shaved, scrubbed with Dial™ brand antimicrobial solution (containing 4% chlorhexidine gluconate and 4% isopropyl alcohol) followed by an application of iodine (10%) spray solution. A 2.5 to 3.0 cm laparotomy is preformed and the radio-telemetry units implanted into the abdomen, with the catheter tip inserted into the abdominal aorta. Baby Weitlaner retractors are used to retain soft tissue. A 1 cm section of the abdominal aorta is partially dissected and that section cross-clamped briefly, punctured with a 21-gauge needle and the transmitter catheter tip introduced into the vessel and secured by a single 4.0 silk suture anchored to the adjacent psoas muscle. The transmitter body is then inserted into the abdominal cavity and simultaneously secured to the abdominal muscle wall while closing with running 4.0 silk suture. The skin layer is closed with subdermal continuous 4.0 absorbable suture. A subcutaneous (s.c.) administration of marcaine followed by a topical application of iodine is administered into and around the suture line, respectively, upon closing. All rats receive a postoperative injection of buprenorphine @ 0.05 mg/kg, s.c. before regaining consciousness. A typical dose volume for a 0.300 kg rat will be 0.050 ml. The rats must be fully recovered from their operative anesthesia before the administration of buprenorphine. They then receive the same dose once daily for 2 consecutive days, unless the animal demonstrates that it is in compromising postoperative pain.

Following surgery, the rats are returned to their cages and housed individually on solid bottom caging with paper bedding. A period of no less than 7 days is allowed for recovery before experimental procedures are initiated. It has been observed that the rats are typically hypertensive for several days following surgery and return to "normotensive" levels by approximately the $7^{th}$ day post-surgery. They are fed standard rat chow and water ad libitum throughout the experimental time line.

Test compounds are administered intragastrically (i.g.) via gavage, using of a stainless steel, 2½ inch, 18 gauge gavage needle with a balled end. For single daily dosing, the target volume is 3.33 ml/kg, i.g. The dose volume for the test compound is approximately 1 mV rat. The vehicles in which the test compound is administered is methylcellulose (0.5%)+ Tween 80 (0.1%) in 50 mM citrate buffer pH=5.0.

Blood pressure data will be obtained using Data Sciences International's data acquisition program (Version 3.0). Blood pressure samples are recorded at 1.5-3 minute intervals for a 5 second duration 24 hours per day for the entire study. This data is processed by Data Science's data analysis software into averages of a desired time inervals. All other data reduction is performed in Microsoft Excel™ spreadsheets.

O. Toxicity Assays
Method 7: Micronucleus Assay

An in vitro micronucleus assay can be used to determine the mutagenic potential of a test compound. This assay detects chromosome abnormalities resulting from exposure to a test compound by measuring the formation of small membrane-bound DNA fragments such as micronuclei in the cytoplasm of interphase cells.

The assay is conducted using Chinese hamster ovary (CHO) cells under different test conditions in the absence and presence of metabolic activation. Concordance in outcomes between this screening assay and in vitro cytogenetics is around 85%. Direct (−S9) testing is conducted using 24 hour or 3 hour continuous treatments, whereas testing with metabolic activation (+S9) involves a 3 hour treatment. Clastogenicity is indicated by an increase in numbers of micronucleated cells in the first interphase after exposure (in cytokinesis-blocked binucleated cells). The results are compared to the level of cytotoxicity (measured by the proportion of binucleated cells) a test compound produces. To demonstrate validity of the test, negative (vehicle-treated) and positive (a known responder) controls are required to respond within established historical ranges.

Negative—A negative result identifies no genotoxic hazard defined by the assays specific endpoint (ex. negative in vitro micronucleus). A test compound displaying a negative response has not fulfilled specific evaluation criteria for the assay which may include one or both of the following: 1) a reproducible concentration dependent increase in the specific assay endpoint when compared to a negative (vehicle) control and/or 2) one or more test concentrations achieving a minimum fold increase in the specific endpoint over controls.

Positive—A positive result identifies a genotoxic hazard defined by the assays specific endpoint (ex. positive in vitro micronucleus). A test compound displaying a positive response has fulfilled specific evaluation criteria for the assay which may include one or both of the following: 1) a reproducible concentration dependent increase in the specific assay endpoint when compared to a negative (vehicle) control and/or 2) one or more test concentrations achieving a minimum fold increase in the specific endpoint over controls.

Equivocal—An equivocal result is reserved for situations where the test compound has been evaluated in a valid assay test or tests (i.e. assay acceptability criteria satisfactory), but fails to display a negative or positive result as defined by established evaluation criteria. This may convey the presence of a weak positive response that requires additional repeat testing or eventual confirmatory testing case-by-case.

Inconclusive—An inconclusive result is reserved for situations where the test compound has been evaluated in an invalid assay test (i.e. assay acceptability criteria unsatisfactory for technical reasons, ex. negative or positive controls fail to respond appropriately). Repeat testing is recommended in order to establish a valid assay test result.

The Carboxypiperidine Compound was tested in accordance with Method 7 and yielded an equivocal result.

Compounds previously disclosed in examples from WO2004096810 that were tested in accordance with Method 7. The corresponding micronucleus assay results are reported in Table G.

TABLE G

| WO2004096810 EXAMPLE NO. | METHOD 7: MICRONUCLEUS ASSAY |
|---|---|
| 261 | Positive |
| 262 | Equivocal |
| 263 | Positive |

Additional assays that can be used to evaluate the toxicity of a test compound (e.g., where the micronucleus assay yields an equivocal result) include Method 8, Method 9, and Method 10 described below:

Method 8: In Vitro Structural Chromosome Aberration in Human Peripheral Lymphocytes An in vitro structural chromosome aberration assay can be used to evaluate a test compound for its ability to induce structural and numerical chromosome aberrations in the presence and absence of mammalian metabolic activation in human peripheral lymphocytes.

Concentration calculations are based on the corresponding moiety factor of 1.000. The test compound is dissolved and diluted in DMSO, which will serve as the vehicle control at a volume equivalent to that used to deliver the test compound (1% final concentration).

Heparinized human peripheral venous blood from a healthy male volunteer are added to culture medium, followed by addition of phytohemagglutinin M (Sigma Chemical Co., St. Louis, Mo.) to stimulate the cellular division of lymphocytes. The primary cultures are incubated for at least 46 hours prior to treatment with the test compound.

The following positive control is utilized:

TABLE 1

Positive Controls

| Positive Control | Metabolic Activation | Test Compound Incubation Time (hours) | Concentration (µg/mL) |
|---|---|---|---|
| Cyclophosphamide (CP) | + | 3 | 10 |
| Mitomycin C (MMC) | − | 3 | 0.4 |
| Mitomycin C (MMC) | − | 24 | 0.1 |

The following treatments are utilized:

TABLE 2

Treatment Conditions

| Treatment | Test Compound Incubation Time (hours) | Metabolic Activation (S9) | Harvest Time (hours) |
|---|---|---|---|
| (1) 3-Hr + S9 | 3 | + | 24 |
| (2) 3-Hr − S9 | 3 | − | 24 |
| (3) 24-Hr − S9 | 24 | − | 24 |

The following dose levels are selected for the assay:

TABLE 3

Dose Levels

| Treatment | Concentrations (µg/mL) |
|---|---|
| (1) 3-Hr + S9 | 100, 200, 250, 300, 400, 500, 600, 700 |
| (2) 3-Hr − S9 | 100, 200, 250, 300, 400, 500, 600, 700 |
| (3) 24-Hr − S9 | 50, 75, 100, 200, 250, 300, 350, 400 |

Single cultures of cells for each concentration and a vehicle control are dosed. Cell cultures are exposed to 0.1 µg/mL Colcemid® (Ciba, Switzerland) for 2 hours prior to harvest. Cells are harvested by centrifugation, swelled in a hypotonic solution and then fixed in a methanol:glacial acetic acid fixative solution. The fixed cell suspension is dropped onto wet microscope slides, dried, and stained with Giemsa. For each concentration of drug tested, at least 2 slides per culture are prepared.

Cytotoxicity is measured by an assessment of chromosome morphology and the inhibition of mitosis (mitotic index). A mitotic index is determined for all treatment conditions by scoring 1000 cells per condition for the proportion of metaphase cells.

The maximum concentration selected for scoring chromosome aberrations is the highest dose at which a sufficient number of analyzable metaphase cells are expected. If possible, the highest dose selected would suppress the mitotic index by approximately 50%, but not greater than 70% reduction.

At least one concentration under each test condition is selected for analysis along with the concurrent vehicle and positive control. The slides arel not analyzed in a blinded fashion. At the discretion of the study director, additional test concentrations may be evaluated after the initial evaluation has been completed to provide further clarification of an effect (i.e., an increase or absence of aberrations).

The highest test concentration selected for analysis should meet 1 of the following criteria: (1) produces approximately a 50% reduction of the mitotic index compared to the vehicle controls, (2) shows evidence of incomplete solubility, or (3) is equivalent to the maximum concentration of 5000 µg/mL or 10 mM (whichever is lower). When possible, 100 acceptable diploid metaphase cells from each culture are evaluated for chromosome damage. An exception to this is an apparent increase in the frequency of abnormal cells during data collection (i.e., >10 aberrant cells are tallied in the first 50 acceptable cells) in which case further analysis is discontinued. Metaphase cells selected for analysis must be intact (i.e., have 46±2 chromosomes), and have a minimum of overlapping chromosomes. In addition, the chromosomes should appear elongated such that the individual arms and centromeric regions can be readily identified. Each metaphase cell is classified as normal or abnormal with the type(s) and number of abnormalities present per cell recorded. For abnormal cells, the stage X and Y vernier co-ordinates of the slide are recorded. Structural chromosome aberrations are classified as chromatid break (Ct brk), chromatid fragments (Ct Frg), chromatid damage including exchanges, rings, dicentrics and translocations (R), chromosome breaks (CsBrk), chromosome fragments (Cs Frg) and multiple breaks (M). In addition, cells with pulverized chromosomes (PV) are collected in the total aberration tally. Cells that contained gaps are recorded but not included in the total aberration tally. Numerical chromosome aberrations are determined for each treatment condition and the concurrent vehicle controls by evaluating the number of polyploid and endoreduplicated cells. The polyploidy indices are obtained by scoring when possible 1000 metaphase cells/culture while tabulating the number of metaphase cells that are polyploid or endoreduplicated.

A Fisher's Exact 1-tailed test on the total number of aberrant cells from each treatment group compared to the total aberrant cells from the negative controls are used as the statistical analysis.[5] A p-value$\leq$0.05 is considered to be statistically significant.

An assay is considered valid if the following criteria are met:
1. Positive control induces a statistically significant increase in the percentage of cells with chromosome aberrations when compared to the concurrent vehicle control and the induced frequencies are comparable to published or historical data.
2. Vehicle control cultures have $\leq$3% of cells with aberrations or a percentage considered comparable to published or historical data.
3. Approximately 50% inhibition of mitotic index is observed at the highest dose level. This requirement is not applicable to test compounds for which no apparent cytotoxicity could be achieved at the maximum soluble concentration or highest allowable dose.

Method 9: Seven Day Oral Gavage Toxicity Study in the Male SD/IGS Rat

The toxicity of a test compound can be evaluated in a rat model. This study determines the potential toxicity of and systemic exposure to test compounds, when administered by oral gavage, once daily, for 7 consecutive days, to 6 to 8 week old male Charles River SD/IGS rats weighing between 175 g and 200 g. This study is conducted using the Xybion Path/Tox System (Xybion Medical Systems Corporation, Cedar Knolls, N.J.).

The test compound is dosed orally once for 7 days by gavage at a volume of 10 mUkg of body weight. The test compound is administered to 3 groups of rats (n=5) getting doses of 30 mg/kg/day, 100 mg/kg/day, and 500 mg/kg/day, respectively. A control group (n=5) receives vehicle (0.5% Methylcellulose (w/v) and 0.1% Polysorbate 80 (v/v) in 50 mM phosphate buffer). The oral route is used because it is the intended route of exposure in humans. The appropriate amount of test compound is suspended in 0.5% methylcellulose (w/v) and 0.1% polysorbate 80 (v/v) in 50 mM citrate buffer. The dosing suspension pH is maintained between 3 and 9.

Every animal is serially bled at 1, 3, 8, and 24 hours post dose on Day 1. Urine is collected approximately 24 hours for metabolic analysis. Survival and moribundity observations are conducted once daily during the pre treatment period. Clinical signs are observed daily, 1-3 hours post dose. Animals are euthanized via exsanguination after 7 days. Animals found dead are refrigerated and necropsied at the earliest possible time (within working hours). Terminal body weights, blood samples and organ weights are not taken from animals found dead. Moribund/unscheduled/scheduled animals that are sacrificed are taken immediately to necropsy, and body weights, blood samples, and all clinical clinical pathology samples except for urine samples are taken.

Various tissues (adrenal, femur bone, brain, cecum, colon, duodenum, epididymis, heart, ileum, jejunum, kidney, liver, pancreas, biceps femoris skeletal muscle, spleen, stomach, testis, thymus, thyroid, lumbar spinal cord, and mesenteric lymph node) will be weighed, flash freezed stained and fixed. After macroscopic examination, tissues collected with gross abnormalities are retained in formalin. All tissues collected with gross abnormalities are processed and examined microscopically by the pathologist. Tissues are trimmed, embedded, sectioned, and stained with hem atoxylin and eosin and examined microscopically by the pathologist at the pathologist's discretion. Bone marrow smears are prepared and stained with Wright's stain. To elucidate the nature of an individual animal's tissue change, additional tissue collection, sectioning, staining, and microscopic examination is conducted as requested by the pathologist.

Clinical observations, body weights, gross necropsy observations, and histopathologic findings are directly entered into the Xybion Path/Tax System.

Method 10: BioLum Ames Gene Mutation Assay

A *Salmonella* mutagenicity test (also known as the Ames test) can be used to determine the mutagenic potential of a test compound. This assay measures the mutation rate of bacteria that are exposed to a test compound. See, for example, Ames, B. N., Durston, W. E., Yamasaki, E. and Lee, F. D. (1973) Carcinogens are mutagens: a simple test system combining liver homogenates for activation and bacteria for detection. Proc. Natl Acad. Sci. USA, 70, 2281-2285). Some carcinogens become activated when they are enzymatically transformed to an electrophilic species capable of covalently binding to DNA. In the Ames assay, S9 (9000 g supernatant) fractions are prepared from the livers of rats pretreated with phenobarbital (PB)/5,6-benzoflavone (BF) or Aroclor 1254 to induce such drug metabolizing enzyme activity.

The BioLum Ames assay is a higher throughput screening version of the standard bacterial (Ames) gene mutation assay. To demonstrate validity of the test, negative (vehicle-treated) and positive (a known responder) controls are required to respond within established historical ranges.

Negative—A negative result identifies no genotoxic hazard defined by the assays specific endpoint (ex. negative in vitro micronucleus). A test compound displaying a negative response has not fulfilled specific evaluation criteria for the assay which may include one or both of the following: 1) a reproducible concentration dependent increase in the specific assay endpoint when compared to a negative (vehicle) control and/or 2) one or more test concentrations achieving a minimum fold increase in the specific endpoint over controls.

Positive—A positive result identifies a genotoxic hazard defined by the assay's specific endpoint (ex. positive in vitro micronucleus). A test compound displaying a positive response has fulfilled specific evaluation criteria for the assay which may include one or both of the following: 1) a reproducible concentration dependent increase in the specific assay endpoint when compared to a negative (vehicle) control and/or 2) one or more test concentrations achieving a minimum fold increase in the specific endpoint over controls.

Equivocal—An equivocal result is reserved for situations where the test compound has been evaluated in a valid assay test or tests (i.e. assay acceptability criteria satisfactory), but fails to display a negative or positive result as defined by established evaluation criteria. This may convey the presence of a weak positive response that requires additional repeat testing or eventual confirmatory testing case-by-case.

Inconclusive—An inconclusive result is reserved for situations where the test compound has been evaluated in an invalid assay test (i.e. assay acceptability criteria unsatisfactory for technical reasons, ex. negative or positive controls fail to respond appropriately). Repeat testing is recommended in order to establish a valid assay test result.

P. Pharmacokinetic/Pharmacodynamic Study

Method 11: Single Dose Pharmacokinetics and Oral Bioavailability in Male Sprague-Dawley Rat Following Intravenous and Oral Administration An in vivo model can be used to evaluate the single dose pharmacokinetic properties and absolute oral bioavailability of a test compound. As described more specifically below, a test compound is administered to Sprague-Dawley (SD) rats either intravenously or orally in a crossover study design and the resulting pharmacokinetic properties and oral bioavailability are measured.

Male rats are administered a 2.0 mg/kg dose orally (n=2) by gavage as a suspension (0.5% methylcellulose/0.1% Tween 80 in distilled water). After a 72 hour wash-out periond, the same rats were administered 2.0 mg/kg dose bolus intravenously (n=2) as a solution (70% PEG 400/20% 0.05 M Citrate Buffer pH 3/10% Ethanol). Serial blood samples (for plasma) are collected from each rat over a 24 hour post dose for each route. Plasma concentrations of test compound are determined using a LC/MS/MS method with a lower limit of quantitation (LLOQ) of 1.2 (for −534) ng/mL. Pharmacokinetic parameters of a test compound are determined from the plasma concentration-time data using non-compartmental methods.

LC/MS/MS: 1) Column: Hyperso; AQUASIL C-18 2.1×20 mm, 3.0 µm; 2) Mobile phase: Aqueous Water with 0.1% Formic Acid, Orgainic: Acetonitrile; Ionization: +ESI (API 4000). MRM: m/z 494.4→m/z 394.0 (Example 261 in WO2004096810), m/z 509.44→m/z 409.80 (Example 263 in WO2004096810), m/z 495.33→m/z 395.20 (Example 262 in WO2004096810). The detection limits are 0.12 ng/mL (Example 261 in WO2004096810), 1.3 ng/mL (Example 263 in WO2004096810) and 0.11 ng/mL (Example 262 in WO2004096810).

Watson (Version 6.4.0.04) is used to calculate mean test compound concentrations, corresponding standard deviations (SD), and percent coefficient of variation (% CV), and to estimate pharmacokinetic parameters (derived by noncompartmental methods) and associated statistics (mean, SD & CV %) if applicable. (Since n=2, no SD or CV calculated ?). Concentrations below the limit of quantitation (BLQ) are reported as zero (0) and are used in the evaluation of mean concentrations and the estimation of AUC. The peak plasma concentration ($C_{max}$) and the time to reach peak concentration (tmax) are recorded directly from individual plasma concentration-time profiles. The terminal log-linear phase of the plasma concentration-time curve is identified by linear regression of data points. The terminal half-life ($t_{1/2}$) is calculated as ln(2) divided by absolute value of the slope of the terminal log-linear phase. The area under the plasma concentration-time curve from time zero to time of the last quantifiable concentration (t) [$AUC_{(0-t)}$] is determined using the linear trapezoidal method. The area under the plasma concentration-time curve from time zero to infinity [$AUC_{(0-\infty)}$] is determined as $AUC_{(0-t)}$ plus the extrapolated area. The extrapolated area is determined by dividing the last observed plasma concentration by the slope of the terminal log-linear phase. Systemic plasma clearance (CL) is calculated as dose/$AUC_{(0-\infty)}$ while the volume of distribution at steady state ($V_{dss}$) is calculated as CL×MRT, where MRT (mean residence time) is defined as $AUMC_{(0-\infty)}/AUC_{(0-\infty)}$. The absolute PO bioavailability (F) is calculated as a ratio of the dose-normalized $AUC_{(0-\infty)}$ of individual animal after PO administration to the dose-normalized $AUC_{(0-\infty)}$ of individual animal after IV administration given the crossover study design. The peak plasma concentration ($C_{max}$), the time to reach peak concentration ($t_{max}$), the terminal half-life ($t_{1/2}$), the area under the plasma concentration-time curve from time zero to infinity [$AUC_{(0-\infty)}$], the volume of distribution at steady state ($V_{dss}$), the systemic plasma clearance (CL), and the absolute PO bioavailability (F) are shown in Table C.

The Carboxypiperidine Compound was tested in accordance with Method 11 and the results are reported in Table H. Compounds previously disclosed in examples from WO2004096810 were tested in accordance with Method 11. Results for these compounds are also are reported in Table H.

sure lowering and whether co-administration of the Carboxypiperidine Compound and the angiotensin converting enzyme inhibitor enalapril could result in further blood pressure lowering. The study consisted of treating spontaneously hypertensive rats (SHR) telemetered as described in Method F with the Carboxypiperidine Compound (1 mg/kg once daily oral) and enalapril (0.007% in drinking water) alone and in combination for 7 days (FIG. 1) (n=12/group). The Carboxypiperidine Compound reduced blood pressure from a pre-dose baseline value in comparison to a vehicle treated group by 11±1 mmHg on day 1. The reduction in blood pressure was sustained for the 7-day period, remaining 9±1 mmHg below the pre-dose baseline on day 7.

Enalapril also reduced blood pressure from a pre-dose baseline value in comparison to a vehicle treated group with a maximal reduction of 22±2 mmHg on day 7. The combination of the Carboxypiperidine Compound plus enalapril reduced blood pressure more than blood pressure was reduced by each agent alone on all days.

Figure 2:
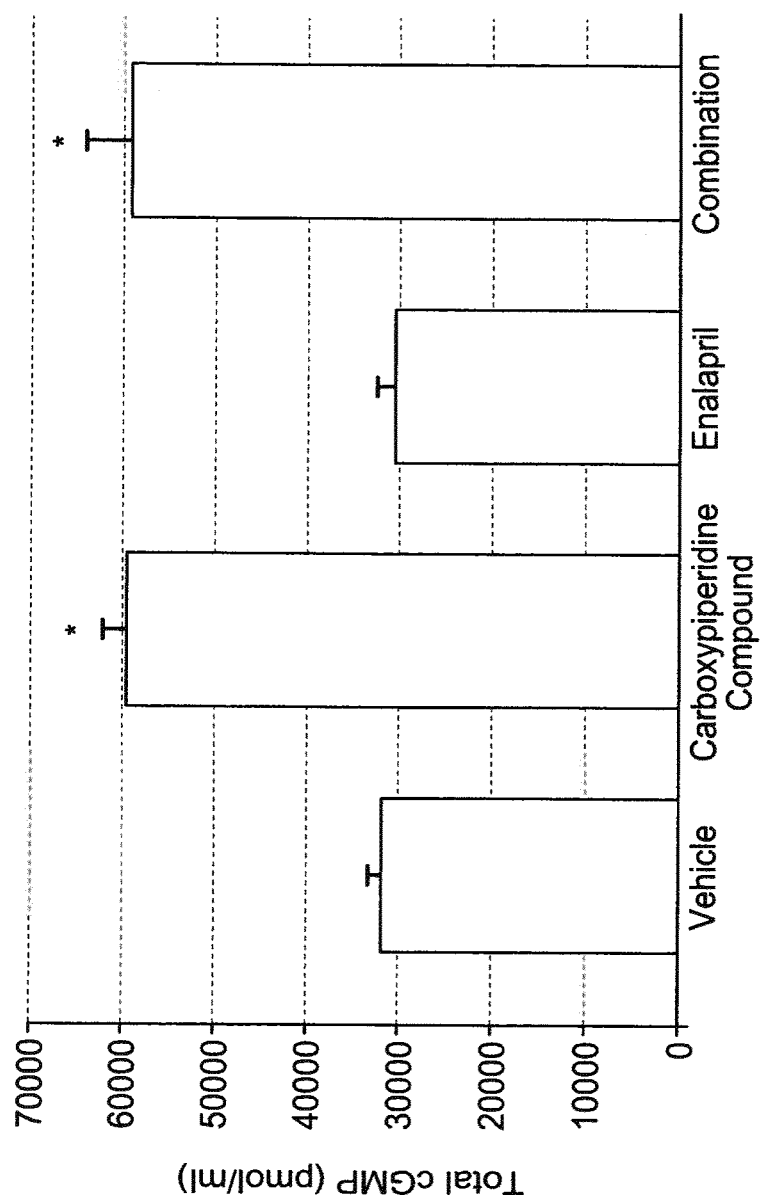
FIG. 2 shows a graph illustrating the effect on 24-hour urinary cGMP of repeated oral administration of 1-(1-(2-ethoxyethyl)-3-ethyl-7-(4-methyl pyridin-2-ylamino)-1H-pyrazolo[4,3-d]pyrimidin-5-yl)piperidine-4-carboxylic acid (1 mg/kg daily oral dose), alone and in combination with enalapril, in a conscious spontaneous hypertensive rat model.

Changes in the urinary cGMP mechanistic biomarker were assessed over the 24-hour period on day 9. cGMP was elevated in a 0-24 hour urine collection in both the Carboxypiperidine Compound and the Carboxypiperidine Compound+enalapril combination groups in comparison to the vehicle treated group (FIG. 2) (n=12/group).

All documents mentioned in this application are expressly incorporated by reference as if fully set forth at length. When introducing elements of the present invention or the preferred

TABLE H

Summary of Mean PK Parameters

| Compound | Route | Dose (mg/kg) | N | $C_{max}$ (ng/mL) | $t_{max}$ (hr) | $t_{1/2}$ (hr) | AUC (0-∞) (ng · hr/mL) | $V_{dss}$ (L/kg) | CL (mL/min/kg) | F (%) |
|---|---|---|---|---|---|---|---|---|---|---|
| Carboxypiperidine | iv | 2 | 2 | | | 6.3 | 17500 | 0.715 | 1.9 | |
| Compound | po | 2 | 3 | 1360 ± 216 | 0.5 ± 0.2 | 5.7 ± 0.2 | 9070 ± 2300 | | | 51.8 ± 13.1 |
| WO2004096810, | iv | 2 | 2 | | | 6.4 | 19017 | 0.564 | 1.75 | |
| Example 261 | po | 2 | 2 | 2351 | 0.67 | 6.7 | 20040 | | | 105 |
| WO2004096810, | iv | 2 | 2 | | | 5.5 | 440 | 6.11 | 76.3 | |
| Example 262 | po | 2 | 2 | 87.1 | 0.67 | 3.4 | 280 | | | 63.9 |
| WO2004096810, | iv | 2 | 2 | | | 4.5 | 555 | 5.07 | 60.1 | |
| Example 263 | po | 2 | 2 | 102 | 0.33 | 3.8 | 329 | | | 60.0 |

Q. Biological Protocols—Coadministration with Angiotensin Converting Enzyme Inhibitor
Method 12: SHR Rat Combination Therapy A study was conducted to assess the effect of repeated oral dosing of the Carboxypiperidine Compound on blood presembodiment(s) thereof, the articles "a", "an", "the" and "said" are intended to mean that there are one or more of the elements. The terms "comprising", "including" and "having" are intended to be inclusive and mean that there may be additional elements other than the listed elements.

I claim:

1. A compound, or a pharmaceutically acceptable salt thereof of structure:

2. The free acid of the compound of claim 1.

3. A pharmaceutically acceptable salt of the compound of claim 1.

4. A pharmaceutical composition comprising a compound, or a pharmaceutically acceptable salt thereof, of structure:

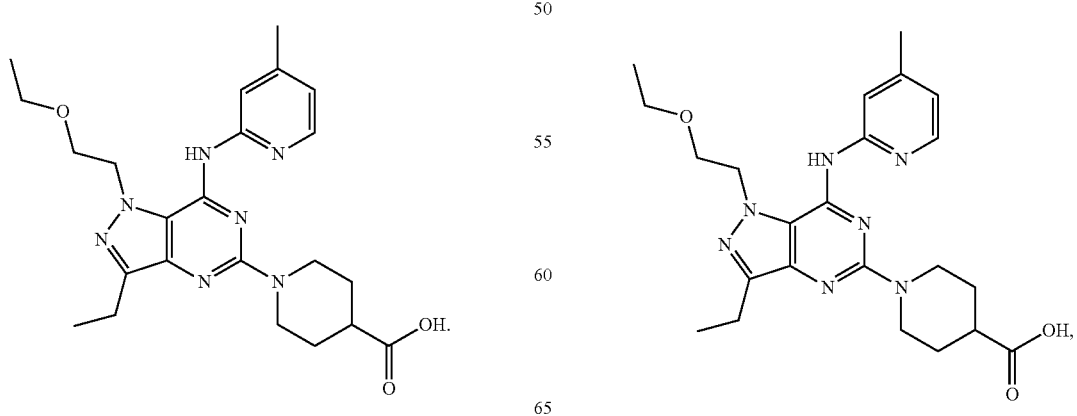

and a pharmaceutically acceptable carrier.

5. The pharmaceutical composition of claim 4 comprising the free acid of the compound.

6. The pharmaceutical composition of claim 4 comprising a pharmaceutically acceptable salt of the compound.

7. The pharmaceutical composition of claim 4 further comprising an angiotensin converting enzyme inhibitor.

8. The pharmaceutical composition of claim 4 further comprising an angiotension II receptor antagonist.

* * * * *

SEQUENCE LISTING

<160> NUMBER OF SEQ ID NOS: 1

<210> SEQ ID NO 1
<211> LENGTH: 1518
<212> TYPE: DNA
<213> ORGANISM: Homo sapiens

<400> SEQUENCE: 1
atggactaca aggacgacga cgacaaggga tcccggtccg agatgtcccc aaagtgcagt      60

```
gctgatgctg agaacagttt caaagaaagc atggagaaat catcatactc cgactggcta    120
ataaataaca gcattgctga gctggttgct tcaacaggcc ttccagtgaa catcagtgat    180
gcctaccagg atccgcgctt tgatgcagag gcagaccaga tatctggttt tcacataaga    240
tctgttcttt gtgtccctat ttggaatagc aaccaccaaa taattggagt ggctcaagtg    300
ttaaacagac ttgatgggaa accttttgat gatgcagatc aacgactttt tgaggctttt    360
gtcatctttt gtggacttgg catcaacaac acaattatgt atgatcaagt gaagaagtcc    420
tgggccaagc agtctgtggc tcttgatgtg ctatcatacc atgcaacatg ttcaaaagct    480
gaagttgaca agtttaaggc agccaacatc cctctggtgt cagaacttgc catcgatgac    540
attcattttg atgactttc tctcgacgtt gatgccatga tcacagctgc tctccggatg    600
ttcatggagc tggggatggt acagaaattt aaaattgact atgagacact gtgtaggtgg    660
cttttgacag tgaggaaaaa ctatcggatg gttctatacc acaactggag acatgccttc    720
aacgtgtgtc agctgatgtt cgcgatgtta accactgctg ggtttcaaga cattctgacc    780
gaggtggaaa ttttagcggt gattgtggga tgcctgtgtc atgacctcga ccacagggga    840
accaacaatg ccttccaagc taagagtggc tctgccctgg cccaactcta tggaacctct    900
gctaccttgg agcatcacca tttcaaccac gccgtgatga tccttcaaag tgagggtcac    960
aatatctttg ctaacctgtc ctccaaggaa tatagtgacc ttatgcagct tttgaagcag   1020
tcaatattgg caacagacct cacgctgtac tttgagagga gaactgaatt ctttgaactt   1080
gtcagtaaag gagaatacga ttggaacatc aaaaaccatc gtgatatatt tcgatcaatg   1140
ttaatgacag cctgtgacct tggagccgtg accaaaccgt gggagatctc cagacaggtg   1200
gcagaacttg taaccagtga gttcttcgaa caaggagatc gggagagatt agagctcaaa   1260
ctcactcctt cagcaatttt tgatcggaac cggaaggatg aactgcctcg gttgcaactg   1320
gagtggattg atagcatctg catgcctttg tatcaggcac tggtgaaggt caacgtgaaa   1380
ctgaagccga tgctagattc agtagctaca aacagaagta agtgggaaga gctacaccaa   1440
aaacgactgc tggcctcaac tgcctcatcc tcctcccctg ccagtgttat ggtagccaag   1500
gaagacagga actaataa                                                 1518
```